US010100028B2

(12) United States Patent
Yiannikouros et al.

(10) Patent No.: US 10,100,028 B2
(45) Date of Patent: Oct. 16, 2018

(54) SYNTHESIS ROUTES FOR PROSTAGLANDINS AND PROSTAGLANDIN INTERMEDIATES USING METATHESIS

(71) Applicant: IRIX PHARMACEUTICALS, INC., Florence, SC (US)

(72) Inventors: George Petros Yiannikouros, Florence, SC (US); Panos Kalaritis, Florence, SC (US); Chaminda Priyapushpa Gamage, Florence, SC (US); Denis Viktorovich Arefyev, Florence, SC (US)

(73) Assignee: Patheon API Services Inc., Florence, SC (US)

( * ) Notice: Subject to any disclaimer, the term of this patent is extended or adjusted under 35 U.S.C. 154(b) by 0 days.

(21) Appl. No.: 15/026,026

(22) PCT Filed: Sep. 30, 2014

(86) PCT No.: PCT/US2014/058298
§ 371 (c)(1),
(2) Date: Mar. 30, 2016

(87) PCT Pub. No.: WO2015/048736
PCT Pub. Date: Apr. 2, 2015

(65) Prior Publication Data
US 2016/0237056 A1    Aug. 18, 2016

Related U.S. Application Data

(60) Provisional application No. 61/884,656, filed on Sep. 30, 2013.

(51) Int. Cl.
| | | |
|---|---|---|
| C07D 313/00 | (2006.01) | |
| C07C 49/753 | (2006.01) | |
| C07C 49/743 | (2006.01) | |
| C07C 41/28 | (2006.01) | |
| C07C 43/196 | (2006.01) | |
| C07C 45/70 | (2006.01) | |
| C07C 67/08 | (2006.01) | |
| C07C 69/604 | (2006.01) | |
| C07D 311/94 | (2006.01) | |

(52) U.S. Cl.
CPC ............ *C07D 313/00* (2013.01); *C07C 41/28* (2013.01); *C07C 43/196* (2013.01); *C07C 45/70* (2013.01); *C07C 49/743* (2013.01); *C07C 49/753* (2013.01); *C07C 67/08* (2013.01); *C07C 69/604* (2013.01); *C07D 311/94* (2013.01)

(58) Field of Classification Search
CPC .................................................. C07D 313/00
See application file for complete search history.

(56) References Cited

U.S. PATENT DOCUMENTS

| | | |
|---|---|---|
| 3,864,387 A | 2/1975 | Nelson |
| 3,935,240 A | 1/1976 | Mallion |
| 4,016,184 A | 4/1977 | Morton, Jr. |
| 4,025,516 A | 5/1977 | Razdan et al. |
| 4,032,543 A | 6/1977 | Bundy |
| 4,032,576 A | 6/1977 | Nelson |
| 4,033,989 A | 7/1977 | Bundy |
| 4,045,449 A | 8/1977 | Bundy |
| 4,049,648 A | 9/1977 | Bundy |
| 4,049,678 A | 9/1977 | Peterson |
| 4,055,602 A | 10/1977 | Nelson |
| 4,079,055 A | 3/1978 | Mallion et al. |
| 4,099,014 A | 7/1978 | Peterson |
| 4,116,979 A | 9/1978 | Razdan et al. |
| 4,122,282 A | 10/1978 | Nelson |
| RE30,053 E | 7/1979 | Bundy |
| 5,164,412 A | 11/1992 | Konishi et al. |
| 5,628,984 A | 5/1997 | Boucher, Jr. |
| 6,262,293 B1 | 7/2001 | Tani et al. |
| 6,586,468 B1 | 7/2003 | Maruyama et al. |
| 6,891,062 B2 | 5/2005 | Oida et al. |
| 6,936,723 B2 | 8/2005 | De Brabander et al. |
| 7,109,371 B2 | 9/2006 | Clissold et al. |
| 8,476,471 B2 | 7/2013 | Yiannikouros et al. |
| 2005/0154220 A1 | 7/2005 | Clissold et al. |
| 2005/0228185 A1 | 10/2005 | Donde |
| 2005/0282898 A1 | 12/2005 | Buchwald et al. |
| 2006/0264353 A1 | 11/2006 | Maxey et al. |
| 2007/0254920 A1 | 11/2007 | De Long et al. |

(Continued)

FOREIGN PATENT DOCUMENTS

| | | |
|---|---|---|
| EP | 0 171 441 | 2/1986 |
| GB | 1 554 023 | 10/1979 |

(Continued)

OTHER PUBLICATIONS

Honn, KV. et al. Prostaglandins and cancer: A review of tumor initiation through tumor metastasis. Prostaglandins. 1981, vol. 21, p. 833.*
"10006692 (+)-15-epi Clo," Cayman Chemical. 1 page <http://www.caymanchem.com/app/template/Product.vm/catalog/10006692> (Accessed on Jun. 17, 2009).
"16768 (+)-Fluprostenol," Cayman Chemical. pp. 1-2 <http://www.caymanchem.com/app/template/Product.vm/catalog/16768> (Accessed on Jun. 17, 2009).
"Carboprost," Wikipedia, the free encyclopedia. 1 page <http://en.wikipedia.org/wiki/Carboprost> (Accessed on Jun. 17, 2009).
"Latanoprost," Wikipedia, the free encyclopedia. 1 page <http://en.wikipedia.org/wiki/Latanoprost> (Accessed on Jun. 17, 2009).
"Limaprost—Compound Summary," PubChem Public Chemical Database. 1 page <http://pubchem.ncbi.nlm.nih.gov/summary/summary.cgi?cid=6438378> (Accessed on Jun. 17, 2009).
"Misoprostol," Wikipedia, the free encyclopedia. pp. 1-6 <http://en.wikipedia.org/wiki/Misoprostol> (Accessed on Jul. 8, 2010).

(Continued)

*Primary Examiner* — David K O'Dell
(74) *Attorney, Agent, or Firm* — Jenkins, Wilson, Taylor & Hunt, P.A.

(57) ABSTRACT

Methods of synthesizing prostaglandins, prostaglandin analogs and their synthetic intermediates are described. The methods can comprise metal-catalyzed metathesis reactions. Also provided are synthetic intermediates that can be used in the synthesis of the prostaglandins and prostaglandin analogs.

23 Claims, No Drawings

(56) References Cited

U.S. PATENT DOCUMENTS

| | | |
|---|---|---|
| 2009/0048203 A1 | 2/2009 | Cavero-Tomas et al. |
| 2009/0259058 A1 | 10/2009 | Henschke et al. |
| 2010/0105771 A1 | 4/2010 | De Long et al. |
| 2012/0165293 A1 | 6/2012 | Yiannikouros et al. |
| 2012/0209011 A1 | 8/2012 | Aswathanarayanappa et al. |
| 2014/0114086 A1* | 4/2014 | Croatt .................. C07F 7/1852 560/119 |

FOREIGN PATENT DOCUMENTS

| | | |
|---|---|---|
| JP | 56-063979 | 5/1981 |
| JP | 61-011231 | 4/1986 |
| JP | 10-259179 | 9/1998 |
| WO | WO 96/028419 | 9/1996 |
| WO | WO2001/057015 | 8/2001 |
| WO | WO2002/090324 | 11/2002 |
| WO | WO2002/096868 | 12/2002 |
| WO | WO 2003/040126 | 5/2003 |
| WO | WO 2004/26224 | 4/2004 |
| WO | WO2004/106356 | 12/2004 |
| WO | WO2005/058812 | 6/2005 |
| WO | WO 2006/063179 | 6/2006 |
| WO | WO2007/111952 | 10/2007 |
| WO | WO 2010/104344 | 9/2010 |
| WO | WO2011/008756 | 1/2011 |
| WO | WO 2012/048447 | 4/2012 |

OTHER PUBLICATIONS

"Prostacyclin," Wikipedia, the free encyclopedia. pp. 1-5 <http://en.wikipedia.org/wiki/Prostacyclin> (Accessed on Jul. 8, 2010).
"Prostaglandin E1," Wikipedia, the free encyclopedia. pp. 1-2 <http://en.wikipedia.org/wiki/Prostaglandin_E1> (Accessed on Jul. 8, 2010).
"Prostaglandin F2alpha," Wikipedia, the free encyclopedia. 1 page <http://en.wikipedia.org/wiki/Prostaglandin_F2alpha> (Accessed on Jul. 8, 2010).
"Sulprostone," Wikipedia, the free encyclopedia. 1 page <http://en.wikipedia.org/wiki/Sulprostone> (Accessed on Jun. 17, 2009).
"Tafluprost," Wikipedia, the free encyclopedia. 1 page <http://en.wikipedia.org/wiki/Tafluprost> (Accessed on Jun. 17, 2009).
"Travoprost," Wikipedia, the free encyclopedia. 1 page <http://en.wikipedia.org/wiki/Travoprost> (Accessed on Jun. 17, 2009).
"Unoprostone," Wikipedia, the free encyclopedia. 1 page <http://en.wikipedia.org/wiki/Unoprostone> (Accessed on Jun. 17, 2009).
Bundy et al., "Synthesis and Biological Activity of Prostaglandin Lactones," Journal of Medicinal Chemistry. vol. 26, No. 8 pp. 1089-1099 (1983).
Collins, P.W., and Djuric, S.W., "Synthesis of Therapeutically Useful Prostaglandin and Prostacyclin Analogs," Chemical Reviews. vol. 93, No. 4 pp. 1533-1564 (1993).
Dörwald, "Side Reactions in Organic Synthesis: A Guide to Successful Synthesis Design," Wiley: VCH, Weinheim. pp. IX of Preface and 1-16 (2005).
Fox et al., "An Enantioconvergent Synthesis of (R)-4-Aryloxy-1-butyne-3-ols for Prostanoid Side Chains," Adv. Synth. Cat., vol. 344, No. 1 pp. 50-56 (2002).
Fürstner et al., "Novel and Flexible Entries into Prostaglandins and Analogues Based on Ring Closing Alkyne Metathesis of Alkyne Cross Metathesis," Journal of the American Chemical Society. vol. 122, No. 48 pp. 11799-11805 (2000).
Ghosh et al., "Factors influencing ring closure through olefin metathesis—A perspective," J. Chem. Sci. vol. 118, No. 3 pp. 223-235 (2006).
Hazato et al., "Synthesis of Thiaprostaglandin E1 Derivatives," Chemical & Pharmaceutical Bulletin. vol. 33, No. 5 pp. 1815-1825 (1985).
Interview Summary corresponding to U.S. Appl. No. 13/383,764 dated Jan. 17, 2013.
Mitsuda et al., "Studies on enantioselective hydrolysis of the acetic ester of a secondary alcohol with Arthrobacter lipase," Applied Microbiology and Biotechnology. vol. 31, No. 4 pp. 334-337 (1989).

Narasaka et al., "A useful method for the synthesis of macrocyclic lactone," Chemistry Letters. vol. 8 pp. 885-888 (1978).
Notice of Allowance corresponding to U.S. Appl. No. 13/383,764 dated Mar. 6, 2013.
Notification Concerning Transmittal of International Preliminary Report on Patentability (Chapter I of the Patent Cooperation Treaty) corresponding to International Patent Application No. PCT/US2010/041825 dated Jan. 26, 2012.
Notification Concerning Transmittal of International Preliminary Report on Patentability (Chapter I of the Patent Cooperation Treaty) corresponding to International Patent Application No. PCT/US2014/058298 dated Apr. 14, 2016.
Notification of Transmittal of the International Search Report and the Written Opinion of the International Searching Authority, or the Declaration corresponding to International Patent Application No. PCT/US2010/041825 dated Sep. 1, 2010.
Notification of Transmittal of the International Search Report and the Written Opinion of the International Searching Authority, or the Declaration corresponding to International Patent Application No. PCT/US2014/058298 dated Feb. 26, 2015.
Official Action corresponding to U.S. Appl. No. 13/383,764 dated Aug. 6, 2012.
Official Action correspondirato U.S. Appl. No. 13/383,764 dated Oct. 15, 2012.
Pandya, B.A., and Snapper, M.L., "A Cross-Metathesis Route to the 5-F2-Isoprostanes," The Journal of Organic Chemistry, vol. 73, No. 10 pp. 3754-3758 (2008).
Shizuka, M., and Snapper, M.L., "Selective Synthesis of ent-15-epi-F2t-Isoprostane and a Deuterated Derivative," Synthesis. vol. 15 pp. 2397-2403 (2007).
Sosnowski et al., "Competitive Bridgehead Substitution in Electrophilic Oxidation Reactions of Protoadamantane. Synthesis of 3-Protoadamantanol. On the Utility of Molecular Mechanics Calculations for Predicting the Bridgehead Reactivity of Hydrocarbons with Electrophiles," The Journal of Organic Chemistry. vol. 50, No. 15 pp. 2759-2763 (1985).
Taylor, "Organocopper Conjugate Addition-Enolate Trapping Reactions," Synthesis. pp. 364-392 (1985).
Wanasundara, U.N., and Shahidi, F., "Concentration of omega 3-polyunsaturated fatty acids of seal blubber oil by urea complexation: optimization of reaction conditions," Food Chemistry. vol. 65 pp. 41-49 (1999).
Official Action corresponding to Canadian Patent Application No. 2,768,154 dated Nov. 24, 2016.
Cai et al., "Synthesis of Aromatic Modified Prostaglandins from PGA2," J. Chem. Soc., Perkin Trans. I, vol. 7, pp. 1573-1578 (1983).
Chen Jianxing et al., "Synthesis of the Antigluucoma Drug Latanoprost and its Effect on Reduction of Intraocular Pressure (IOP)," Chinese J. Med. Chem., vol. 8, No. 1, pp. 213-217 (1998).
Kalish et al., "An Improved Procedure for the Synthesis of Protaglandin Analogues," Synthetic Communications, vol. 20, No. 11, pp. 1641-1645 (1990).
Maruyama et al., "Design and Synthesis of a Selective EP4-Receptor Agonist. Part 1: Discovery of 3,7-DithiaPGE1 Derivatives and Identification of Their (( Chains," Bioorg. & Med. Chem., vol. 10, pp. 974-988 (2002).
Nakai et al., "Synthesis of 5-Fluoro-Prostaglandins," Chem. Lett., pp. 1499-1502 (1979).
Obadalova et al., "Synthesis of Latanoprost Diastereoisomers," Chirality vol. 17, pp. S109-S113 (2005).
Rodriguez et al., "Effective Stereoselective Total Synthesis of 16,16-Dimethyl Prostaglandin E2," Arch. Pharm. Pharm. Med. Chem., vol. 331, No. 9, pp. 279-282 (1998).
Rodriguez et al., "Total synthesis of E1 and E2 isoprostanes by diastereoselective protonation," Tetrahedron Letters, vol. 43, pp. 9249-9253 (2002).
Selliah et al., "Synthesis of [Phenyl-2-3H]-travoprost Isopropyl Ester Prodrug of a Selective Prostaglandin FP Receptor Agonist," J. Lab. Comp. and Radiopharm., vol. 44, pp. 173-183 (2001).
Sih et al., "Synthesis of the Four Isomers of 5-Hydroxy PGI1," Prostaglandins, vol. 15, No. 3, pp. 409-421 (1978).

(56) References Cited

OTHER PUBLICATIONS

Tani et al., Development of a Highly Selective EP2-Receptor Agonist. Part 1: Identification of 16-hydroxy-17,17-trimethylene PGE2 Derivatives Bioorganic & Medicianl Chemistry, vol. 10, No. 4 pp. 1093-1106 (2002).

Zhang et al., Prostaglandin Synthesis via Two~Component Coupling. Highly Efficient Synthesis of Chiral Prostaglandin Intermediates 4-Alkoxy-2-alkyl-2-cyclopenten-1-one and 4-Alkoxy-3-alkeny l-2-methy lenecyclopentan-I-one J. Org. Chem. vol. 53 pp. 5590-5592 (1988).

Notice of Allowance Corresponding to Canadian Patent Application No. 2,768,154 dated Jun. 20, 2017.

"16814 15(R)-17-phenyl trinor Prostaglandin $F_{2\alpha}$," Cayman Chemical. 2 pages <http://www.caymanchem.com/app/template/Product. vm/catalog/16814/tab/data/a/z;jsessio . . . > (Accessed Aug. 13, 2009).

"Bimatoprost," Wikipedia, the free encyclopedia. 1 page <http://en.wikipedia.org/wiki/Bimatoprost> (Accessed on Jun. 17, 2009).

"Lubiprostone," Wikipedia, the free encyclopedia. 3 pages <http://en.wikipedia.org/wiki/Lubiprostone> (Accessed Jan. 14, 2013).

\* cited by examiner

SYNTHESIS ROUTES FOR PROSTAGLANDINS AND PROSTAGLANDIN INTERMEDIATES USING METATHESIS

RELATED APPLICATIONS

The presently disclosed subject matter is based on and claims the benefit of U.S. Provisional Patent Application Ser. No. 61/884,656, filed Sep. 30, 2013; the disclosure of which is incorporated herein by reference in its entirety.

TECHNICAL FIELD

The presently disclosed subject matter relates to the synthesis of prostaglandins and prostaglandin analogues. The presently disclosed subject matter further relates to novel synthetic intermediates that can be used in the synthesis of prostaglandins and prostaglandin analogues.

BACKGROUND

Prostaglandins are naturally occurring 20-carbon fatty acid derivatives produced by the oxidative metabolism of fatty acids (e.g., arachidonic acid). They and their non-naturally occurring analogs (which together can be referred to as prostanoids) have a wide variety of therapeutic uses.

Prostaglandins typically include at least one five-membered ring. For example, $PGF_\alpha$ prostaglandins and prostaglandin analogs can comprise a cyclopentyl ring carrying two hydroxyl groups in a cis configuration and two side chains in a trans configuration. The side chains can contain double bonds and a variety of substituents. They have therapeutic value in several indications including, but not limited to, glaucoma, ocular hypertension, ulcers, and inducing or accelerating labor.

Bimatoprost, an exemplary $PGF_\alpha$ prostaglandin analog, is sold in the U.S., Canada, and Europe by Allergan under the trade name LUMIGAN™ (Allergan, Inc., Irvine, Calif., United States of America) for use topically as eye drops to control the progression of glaucoma and in the management of ocular hypertension. It reduces intraocular pressure by increasing the outflow of aqueous fluid from the eyes. In December 2008, the U.S. Food and Drug Administration approved a cosmetic formulation of bimatoprost, sold under the trade name LATISSE™ (Allergan, Inc., Irvine, Calif., United States of America) for use as a treatment for inadequate eyelash growth. It has further been suggested that bimatoprost has the ability to reduce adipose (fat) tissue.

A variety of methods for synthesizing $PGF_\alpha$ and other prostaglandins and prostaglandin analogs are known. See e.g., International Publication No. WO 2005/058812 to Clissold et al., WO 02/096868, WO 02/090324, Chem. Rev. (1993, vol. 93, pages 1533 1564), Chinese Journal of Medicinal Chemistry (1998, vol. 36, pages 213-217), and the references cited therein. However, there remains a need in the art for additional methods of synthesizing prostanoids, such as but not limited to more versatile and efficient methods.

SUMMARY

In some embodiments, the presently disclosed subject matter provides a compound of Formula (III):

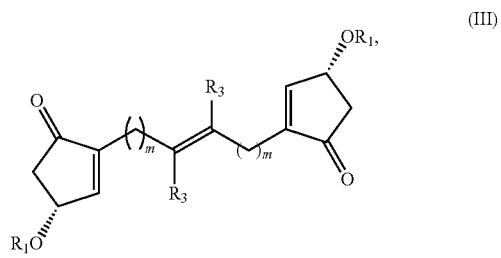

wherein each m is an integer between 0 and 10; each $R_1$ is independently H or a hydroxyl protecting group; and each $R_3$ is independently selected from the group comprising H, alkyl, substituted alkyl, aralkyl, substituted aralkyl, aryl, and substituted aryl.

In some embodiments, the presently disclosed subject matter provides a compound of Formula (IV):

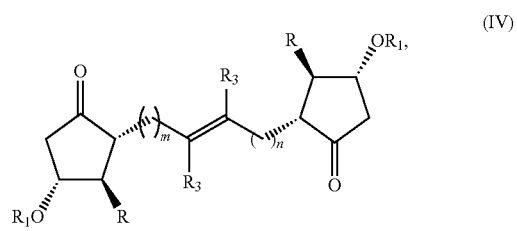

wherein m, $R_1$, and $R_3$ are as defined above for the compound of Formula (III); and each R is selected from the group comprising aldehyde, acyl, nitroalkyl, aminoalkyl, thioalkyl, vinyl, and alkyl or alkenyl of the formula:

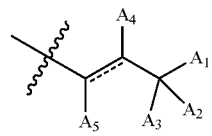

wherein ═══ represents a single or a double bond; $A_1$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino; $A_2$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, with the proviso that $A_2$ is not halogen or amino when $A_1$ or $A_3$ is hydroxyl or amino; $A_3$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, with the proviso that $A_3$ is not halogen or amino when $A_1$ or $A_2$ is hydroxyl or amino; or wherein two of $A_1$, $A_2$, and $A_3$ together form a ring or ═O; and $A_4$ and $A_5$ are independently hydrogen, alkyl, substituted alkyl, cycloalkyl, substituted cycloalkyl, aryl, substituted aryl, aralkyl, substituted aralkyl, acyl, alkoxyl, or aralkoxyl.

In some embodiments, the presently disclosed subject matter provides a compound of Formula (V):

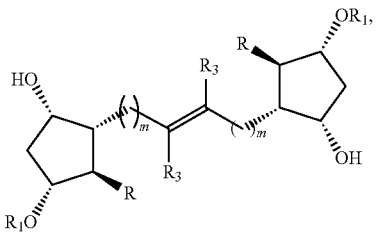

(V)

wherein m, $R_1$, $R_3$, and R are as defined above for the compound of Formula (IV).

In some embodiments, the presently disclosed subject matter provides a compound of Formula (VI):

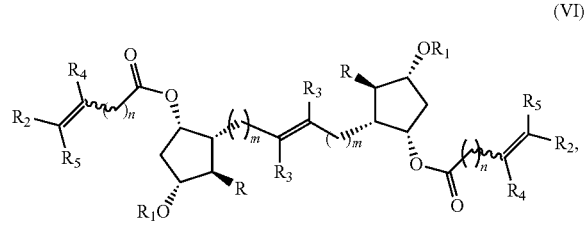

(VI)

wherein m, $R_1$, $R_3$, and R are as defined above for the compound of Formula (IV), n is independently an integer between 0 and 10; and each $R_2$, $R_4$ and $R_5$ is independently selected from the group comprising H, alkyl, substituted alkyl, aralkyl, substituted aralkyl, aryl, and substituted aryl.

In some embodiments, the presently disclosed subject matter provides a method for preparing a prostaglandin, prostaglandin analog, or a synthetic intermediate thereof, the method comprising: providing a compound of Formula (VI) and reacting the compound of Formula (VI) with a transition metal catalyst to perform a ring closing metathesis reaction, thereby forming a lactone, wherein the lactone is a synthetic intermediate of a prostaglandin or prostaglandin analog, optionally further comprising reducing a carbon-carbon double bond in the formed lactone.

In some embodiments, the presently disclosed subject matter provides a method for preparing a compound of Formula (III) as described hereinabove, wherein the method comprises performing a metal-catalyzed intermolecular metathesis reaction with a compound of Formula (I):

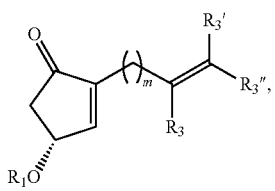

(I)

wherein m, $R_1$ and $R_3$ are as defined for the compound of Formula (III) and wherein $R_3'$ and $R_3''$ are each selected from the group consisting of H, alkyl, substituted alkyl, aralkyl, substituted aralkyl, aryl, substituted aryl, alkoxyl, aralkoxyl, and acyloxyl.

In some embodiments, the presently disclosed subject matter provides a method of preparing a compound of Formula (IV) as described hereinabove, wherein the method comprises: a) preparing or providing a reagent for a 1,4-addition, optionally wherein the reagent is a cuprate reagent prepared from a compound of the Formula (Z):

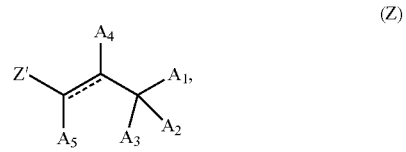

(Z)

wherein $A_1$, $A_2$, $A_3$, $A_4$, and $A_5$ are as described for the compound of Formula (IV) and Z' is selected from halo and alkoxy; and b) performing a 1,4-addition reaction between the reagent from a) and a compound of Formula (III).

In some embodiments, the presently disclosed subject matter provides a method for preparing a compound of Formula (IV) as described hereinabove, wherein the method comprises performing a metal-catalyzed cross-metathesis reaction of a compound of Formula (II):

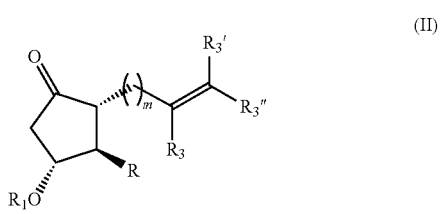

(II)

wherein m, R, $R_1$, and $R_3$ are as described for the compound of Formula (IV) and $R_3'$ and $R_3''$ are each selected from the group consisting of H, alkyl, substituted alkyl, aralkyl, substituted aralkyl, aryl, substituted aryl, alkoxyl, aralkoxyl, and acyloxyl, optionally wherein at least one of $R_3'$ and $R_3''$ is other than H.

In some embodiments, the presently disclosed subject matter provides a method for preparing a compound of Formula (V) as described hereinabove, wherein the method comprises enantioselective reduction of two carbonyl groups of a compound of Formula (IV).

In some embodiments, the presently disclosed subject matter provides a method for preparing a compound of Formula (VI) as described hereinabove, wherein the method comprises esterifying two unprotected hydroxyl groups (e.g., in a compound of Formula (V)) with an alkenoic acid or derivative thereof.

In some embodiments, the presently disclosed subject matter provides a method for preparing a compound of Formula (VII) or Formula (VIII):

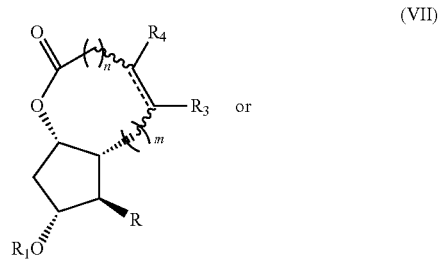

(VII)

or

-continued

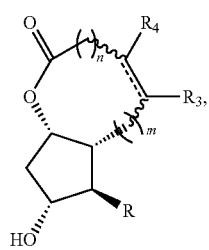
(VIII)

wherein ─── represents a single or a double bond; n, m, $R_1$, $R_3$, $R_4$, and R are as defined for the compound of Formula (VI); wherein the method comprises performing a ring closing metathesis reaction and optionally reducing a carbon-carbon double bond to a carbon-carbon single bond, wherein performing the ring closing metathesis reaction comprises contacting a precursor compound with a transition metal catalyst, wherein said precursor compound comprises a cyclopentane ring substituted by at least four substituent groups, the at least four substituent groups comprising —R, —OR$_1$, and two additional substituent groups, wherein R and $R_1$ are as defined for the compounds of Formula (VII) and Formula (VIII) and the two additional substituent groups each comprise an alkene moiety, further wherein at least one of the two additional substituent groups comprises a non-terminal alkene moiety.

In some embodiments, the presently disclosed subject matter provides a method for preparing a compound of Formula (IX):

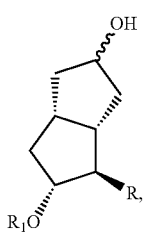

wherein $R_1$ and R are as defined above for the compound of Formula (VI); wherein the method comprises performing a reaction that cleaves the carbon-carbon double bond of a compound of Formula (V).

In some embodiments, the presently disclosed subject matter provides a compound of Formula (VII) or Formula (VIII):

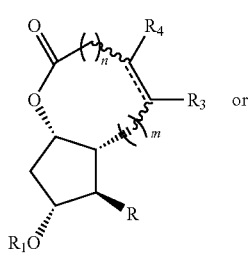
(VII)

or

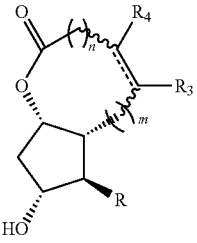
(VIII)

wherein ─── represents a single or a double bond; and n, m, $R_1$, $R_3$, $R_4$, and R are as defined above for the compound of Formula (VI).

In some embodiments, the presently disclosed subject matter provides a compound of Formula (II) or Formula (V-A):

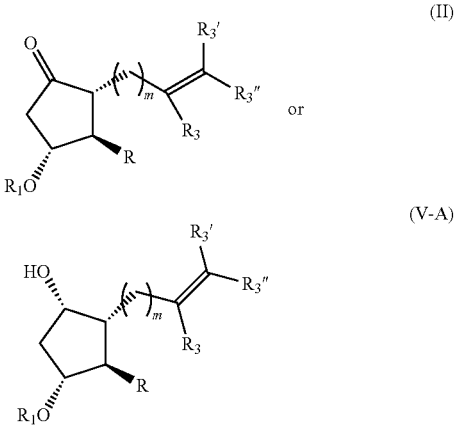

wherein m, $R_1$, $R_3$, and R are as defined above for the compound of Formula (IV), and $R_3'$ and $R_3''$ are selected from the group comprising H, alkyl, substituted alkyl, aralkyl, substituted aralkyl, aryl, substituted aryl, alkoxyl, aralkoxyl, and acyloxyl, further wherein at least one of $R_3'$ and $R_3''$ is other than H.

In some embodiments, the presently disclosed subject matter provides a method of preparing a compound of Formula (VI-A):

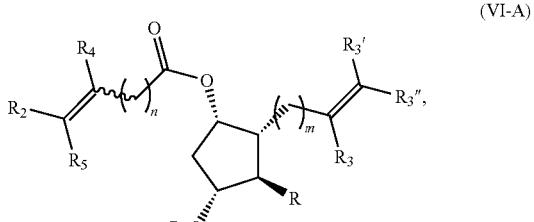
(VI-A)

wherein m, n, $R_1$, $R_2$, $R_3$, $R_4$, $R_5$, and R are as defined for the compound of Formula (VI) and $R_3'$ and $R_3''$ are selected from the group comprising H, alkyl, substituted alkyl, aralkyl, substituted aralkyl, aryl, substituted aryl, alkoxyl, aralkoxyl, and acyloxyl, further wherein at least one of $R_3'$ and $R_3''$ is other than H.

In some embodiments, the presently disclosed subject matter provides a compound of one of Formulae (XI), (XIV), (XV), or (XVI):

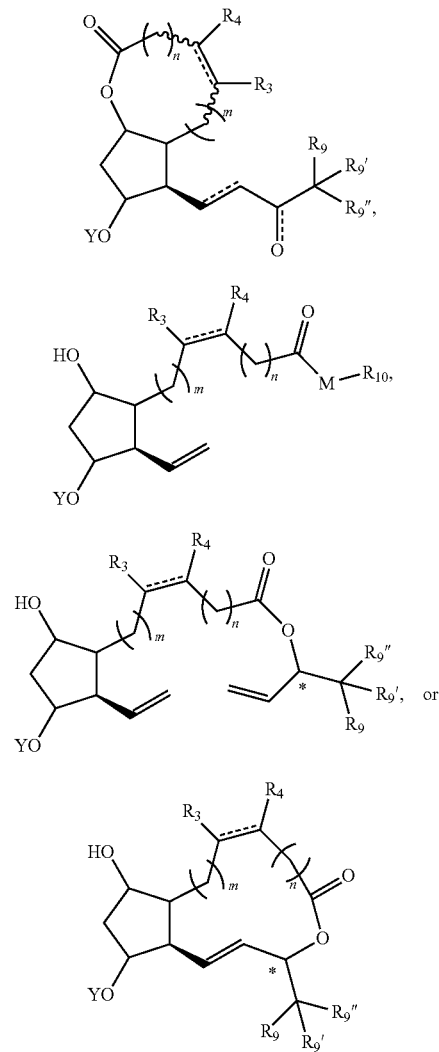

wherein ⚌ represents a single or a double bond; m, n, $R_3$, and $R_4$ are as defined above for the compounds of Formulae (III)-(VI); Y is H or a hydroxyl protecting group; $R_9$ in the compounds of Formulae (XI), (XV), and (XVI) is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, furyl, pyranyl, thioalkyl, thioaralkyl, thioaryl, thiophenyl, benzothiophenyl, halogen, hydroxyl, protected hydroxyl, or amino; $R_9'$ for the compounds of Formulae (XI), (XV), and (XVI) is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, furyl, pyranyl, thioalkyl, thioaralkyl, thioaryl, thiophenyl, benzothiophenyl, halogen, hydroxyl, protected hydroxyl, or amino, provided that $R_9'$ is not halogen or amino when $R_9$ or $R_9''$ is hydroxyl or amino; $R_9''$ for the compounds of Formulae (XI), (XV), and (XVI) is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, furyl, pyranyl, thioalkyl, thioaralkyl, thioaryl, thiophenyl, benzothiophenyl, halogen, hydroxyl, protected hydroxyl, or amino, provided that $R_9''$ is not halogen or amino when $R_9$ or $R_9'$ is hydroxyl or amino; or two or more of $R_9$, $R_9'$, and $R_9''$ together form a ring (e.g., an alkylene group or an aryl or heteroaryl group); M for the compounds of Formula (XIV) is oxygen, nitrogen, or sulfur; $R_{10}$ for the compounds of Formula (XIV) is hydrogen, alkyl, substituted alkyl, cycloalkyl, substituted cycloalkyl, aryl, substituted aryl, aralkyl, substituted aralkyl, alkylacyl, hydroxyacyl, alkoxyacyl, aminoacyl, alkylaminoacyl, or alkylthioacyl; and

* for the compounds of Formulae (XV) and (XVI) represents a chiral center, which can be racemic or enationmerically pure.

In some embodiments, the presently disclosed subject matter provides a compound selected from the group comprising:

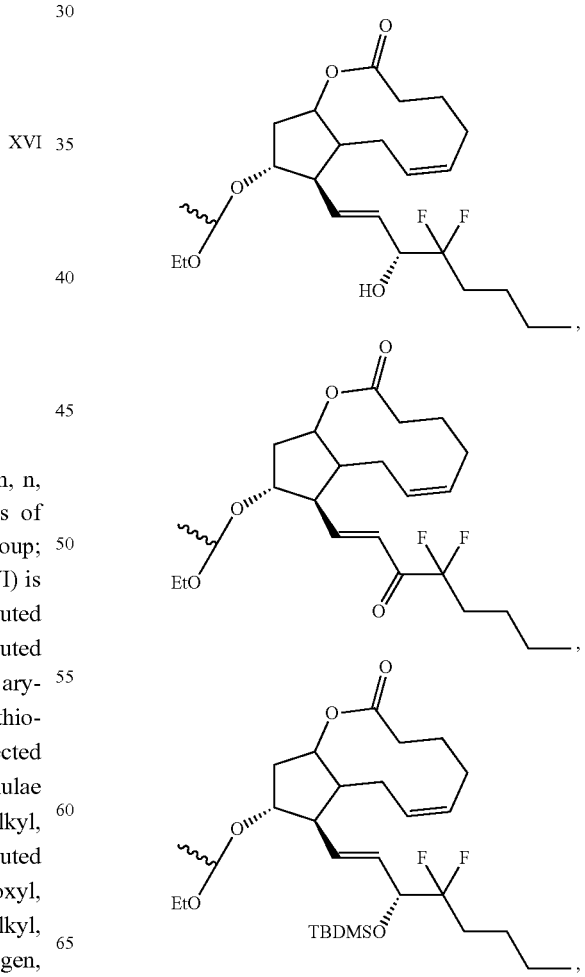

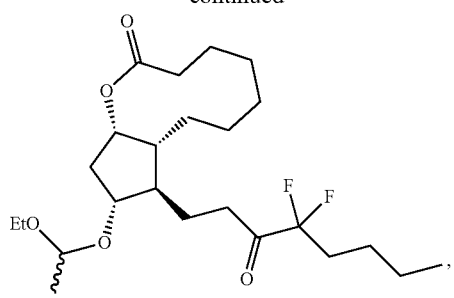
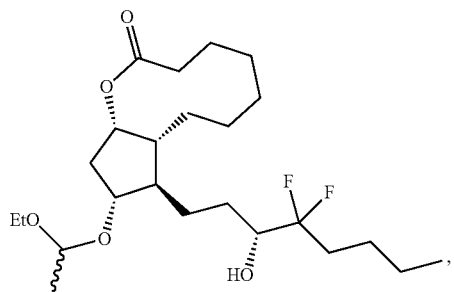
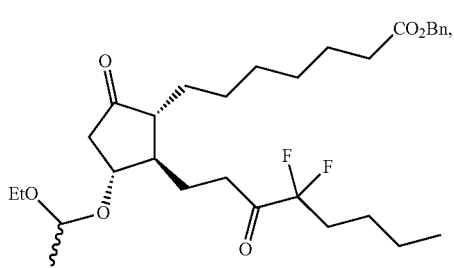
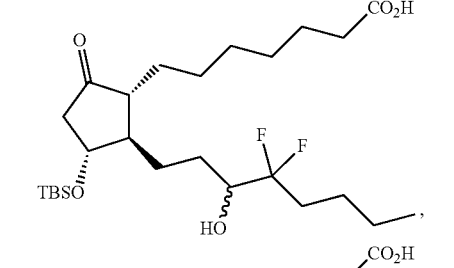
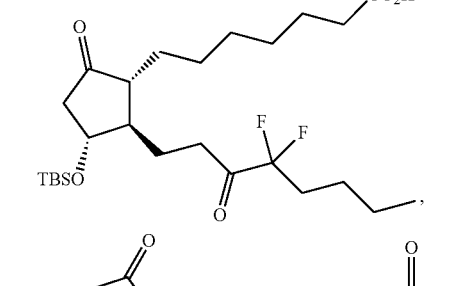
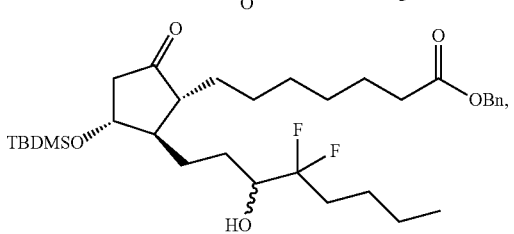
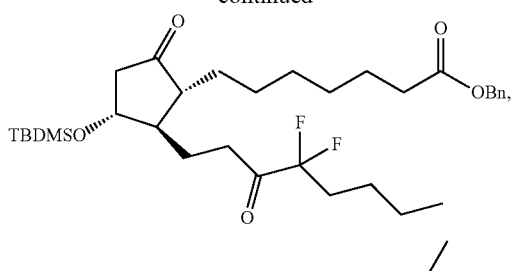
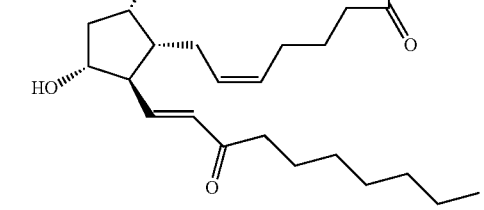
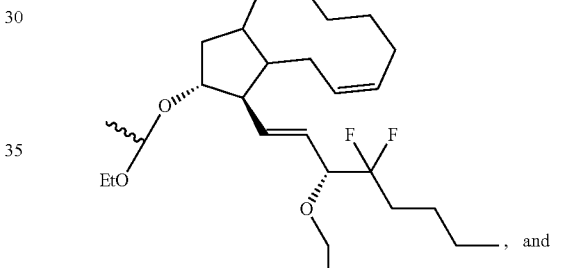
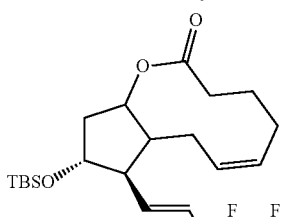
, and
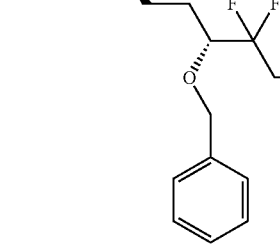
In some embodiments, the presently disclosed subject matter provides a method of preparing a prostaglandin, prostaglandin analog, or a synthetic intermediate thereof, the method comprising: providing a nitro group-containing compound of the formula:

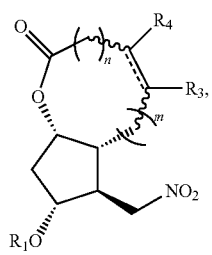

wherein $\equiv\equiv\equiv$ represents a single or a double bond; n and m are each independently an integer between 0 and 10; $R_1$ is H or a hydroxyl protecting group; and $R_3$ and $R_4$ are each independently selected from the group comprising H, alkyl, substituted alkyl, aralkyl, substituted aralkyl, aryl, and substituted aryl; and contacting the nitro group-containing compound with titanium trichloride and sodium acetate to provide an aldehyde of the formula:

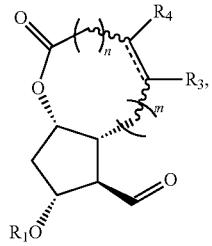

wherein n, m, $R_1$, $R_3$, and $R_4$ are as defined for the nitro group-containing compound.

In some embodiments, the presently disclosed subject matter provides a method of preparing a prostaglandin, prostaglandin analog, or a synthetic intermediate thereof, the method comprising: providing a compound of the Formulae (VII-6) or (VIII-6):

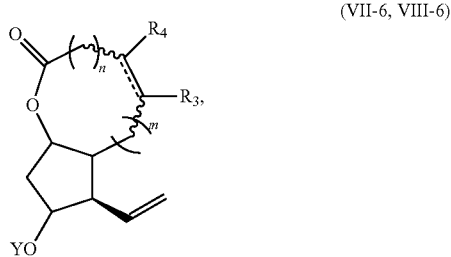

(VII-6, VIII-6)

wherein $\equiv\equiv\equiv$ represents a single or a double bond; n and m are independently integers between 1 and 10 or 0 and 10; Y is a hydroxyl protecting group for the compounds of Formula (VII-6) and H for the compounds of Formula (VIII-6); and $R_3$ and $R_4$ are independently selected from the group comprising H, alkyl, substituted alkyl, aralkyl, substituted aralkyl, aryl, and substituted aryl; and performing one of the following steps: (a) contacting the compound of Formula (VII-6) or (VIII-6) with a metal catalyst and a suitable enone to perform a cross-metathesis reaction, thereby providing a compound of Formula (XI); (b) hydrolyzing the compound of Formula (VII-6) or (VIII-6) to open the lactone and then reacting the resulting carboxylic acid with an alkoxide, thiol, or amine to provide a compound of Formula (XIV); (c) trans-esterifying the compound of Formula (VII-6) or (VIII-6) with a chiral allylic alcohol to provide a compound of Formula (XV); optionally wherein the compound of Formula (XV) can be further reacted with a metal catalyst to undergo an intramolecular metathesis reaction to provide a compound of Formula (XVI).

In some embodiments, the presently disclosed subject matter provides a method of preparing a prostaglandin, prostaglandin analog, or a synthetic intermediate thereof, the method comprising providing a compound of Formula (X):

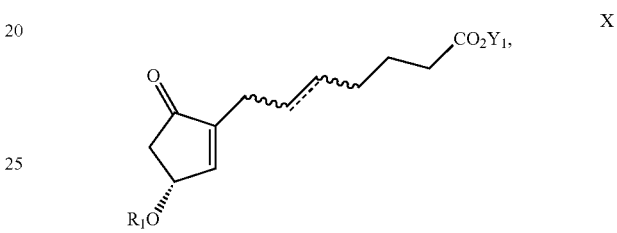

X wherein $R_1$ is H or a hydroxyl protecting group and $Y_1$ is H, alkyl, substituted alkyl, aralkyl, substituted aralkyl, aryl, or substituted aryl, wherein providing the compound of Formula (X) comprises performing a metal-catalyzed metathesis reaction of a compound of Formula (I) and an ester of a hexenoic acid.

In some embodiments, the presently disclosed subject matter provides a method of preparing a prostaglandin, prostaglandin analog, or a synthetic intermediate thereof, the method comprising: providing a compound of Formula (I):

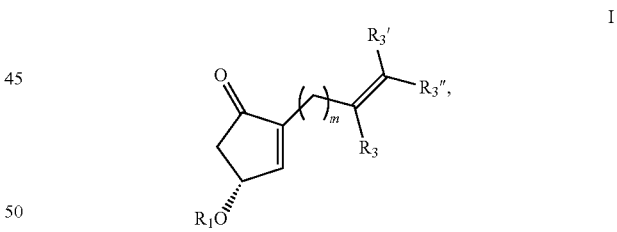

I wherein m is an integer between 0 and 10, optionally wherein m is 1; $R_1$ is independently H or a hydroxyl protecting group; $R_3$ is selected from the group comprising H, alkyl, substituted alkyl, aralkyl, substituted aralkyl, aryl, and substituted aryl; and $R_3'$ and $R_3''$ are selected from the group comprising H, alkyl, substituted alkyl, aralkyl, substituted aralkyl, aryl, substituted aryl, alkoxyl, aralkoxyl, and acyloxyl, and wherein one of $R_3'$ and $R_3''$ is other than H, optionally wherein one of $R_3'$ and $R_3''$ is alkyl; and reacting the compound of Formula (I) with a nucleophile to perform an 1,4-addition, thereby providing a compound of Formula (II):

II

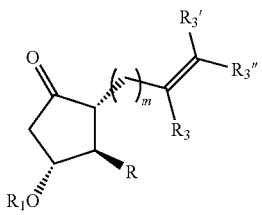

wherein m, $R_1$, and $R_3$ are as defined for the compound of Formula (I); and R is selected from the group comprising aldehyde, acyl, nitroalkyl, aminoalkyl, thioalkyl, vinyl, and alkyl or alkenyl of the formula:

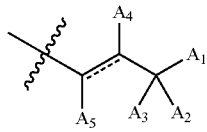

wherein ═══ represents a single or a double bond; $A_1$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino; $A_2$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, with the proviso that $A_2$ is not halogen or amino when $A_1$ or $A_3$ is hydroxyl or amino; $A_3$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, with the proviso that $A_3$ is not halogen or amino when $A_1$ or $A_2$ is hydroxyl or amino; or wherein two of $A_1$, $A_2$, and $A_3$ together form a ring or ═O; and $A_4$ and $A_5$ are independently hydrogen, alkyl, substituted alkyl, cycloalkyl, substituted cycloalkyl, aryl, substituted aryl, aralkyl, substituted aralkyl, acyl, alkoxyl, or aralkoxyl.

In some embodiments, the presently disclosed subject matter provides a compound of Formula (XII) or Formula (XIII):

XII

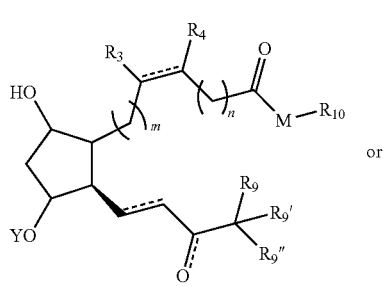

or

XIII

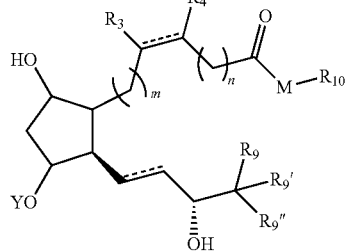

wherein ═══, m, n, Y, $R_3$, $R_4$, $R_9$, $R_9'$, and $R_9''$ as described for the compound of Formula (XI), and M and $R_{10}$ are as described for the compound of Formula (XIV).

It is an object of the presently disclosed subject matter to provide synthetic intermediates and/or prodrugs for prostaglandins, for example, compounds of Formulae (I), (II), (III), (IV), (V), (V-A), (VI), (VI-A), (VII), (VII-5), (VII-5A), (VII-6), (VIII), (VIII-5), (VIII-5A), (VIII-6), (IX), (X), (XI), (XII), (XIII), (XIV), (XV), and/or (XVI), and to provide methods of synthesizing prostaglandins and their synthetic intermediates.

Certain objects of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist, unless as otherwise specifically indicated.

I. Definitions

Following long-standing patent law convention, the terms "a", "an", and "the" refer to "one or more" when used in this application, including the claims. Thus, for example, reference to "a solvent" includes mixtures of one or more solvents, two or more solvents, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, molar equivalents, time, temperature, etc. is meant to encompass in one example variations of ±20% or ±10%, in another example ±5%, in another example ±1%, and in yet another example ±0.1% from the specified amount, as such variations are appropriate to perform the disclosed methods.

The term "and/or" when used to describe two or more activities, conditions, or outcomes refers to situations wherein both of the listed conditions are included or wherein only one of the two listed conditions are included.

The term "comprising", which is synonymous with "including," "containing," or "characterized by" is inclusive or open-ended and does not exclude additional, unrecited elements or method steps. "Comprising" is a term of art used in claim language, which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl (saturated or unsaturated), substituted alkyl (e.g., halo-substituted and perhalo-substituted alkyl, such as but not limited to, —$CF_3$), cycloalkyl, halo, nitro, hydroxyl, carbonyl, carboxyl, acyl, alkoxyl, aryloxyl, aralkoxyl, thioalkyl, thioaryl, thioaralkyl, amino (e.g., aminoalkyl, aminodialkyl, aminoaryl, etc.), sulfonyl, and sulfinyl.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Thus, examples of aryl include, but are not limited to, phenyl, naphthyl, biphenyl, and diphenylether, among others. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, and thiophenyl.

The aryl group can be optionally substituted (a "substituted aryl") with one or more aryl group substituents, which can be the same or different, wherein "aryl group substituent" includes alkyl (saturated or unsaturated), substituted alkyl (e.g., haloalkyl and perhaloalkyl, such as but not limited to —$CF_3$), cycloalkyl, aryl, substituted aryl, aralkyl, halo, nitro, hydroxyl, acyl, carboxyl, alkoxyl, aryloxyl, aralkyloxyl, thioalkyl, thioaryl, thioaralkyl, amino (e.g., aminoalkyl, aminodialkyl, aminoaryl, etc.), sulfonyl, and sulfinyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$-, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group.

As used herein, the term "acyl" refers to an organic carboxylic acid group wherein the —OH of the carboxylic acid group has been replaced with another substituent. Thus, an acyl group can be represented by RC(=O)—, wherein R is an alkyl, substituted alkyl, aralkyl, substituted aralkyl, aryl or substituted aryl group as defined herein. As such, the term "acyl" specifically includes arylacyl groups, such as a phenacyl group. Specific examples of acyl groups include acetyl and benzoyl.

"Cyclic" and "cycloalkyl" refer to a non-aromatic mono- or multi-cyclic ring system of about 3 to about 10 carbon atoms, e.g., 3, 4, 5, 6, 7, 8, 9, or 10 carbon atoms. The cycloalkyl group can be saturated or partially unsaturated. The cycloalkyl group also can be optionally substituted with an alkyl group substituent as defined herein. There can be optionally inserted along the cyclic alkyl chain one or more oxygen. Representative monocyclic cycloalkyl rings include cyclopentyl, cyclohexyl, and cycloheptyl. Multicyclic cycloalkyl rings include adamantyl, octahydronaphthyl, decalin, camphane, and noradamantyl.

"Alkoxyl" refers to an alkyl-O— group wherein alkyl is as previously described, including substituted alkyl. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" refers to an aryl-O— group wherein the aryl group is as previously described, including a substituted aryl. The term "aryloxyl" as used herein can refer to phenyloxyl or hexyloxyl, and to alkyl, substituted alkyl, or alkoxyl substituted phenyloxyl or hexyloxyl.

"Aralkyl" refers to an aryl-alkyl- or an -alkyl-aryl group wherein aryl and alkyl are as previously described, and can include substituted aryl and substituted alkyl. Thus, "substituted aralkyl" can refer to an aralkyl group comprising one or more alkyl or aryl group substituents. Exemplary aralkyl groups include benzyl, phenylethyl, and naphthylmethyl.

"Aralkyloxyl" or "aralkoxyl" refer to an aralkyl-O— group wherein the aralkyl group is as previously described. An exemplary aralkyloxyl group is benzyloxyl. "Substituted aralkyoxyl" can refer to an aralkoxyl group wherein the alkyl and/or aryl portion of the aralkyl are substituted by one or more alkyl or aryl group substituents.

The term "carbonyl" refers to the group —C(=O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group.

The term "carboxyl" refers to the —C(=O)OH or —C(=O)O⁻ group.

The term "aldehyde" can refer to the —C(=O)H group.

The term "ketone" can refer to the —R'—C(=O)—R group or the —C(=O)R group (i.e., when the —C(=O)R group is directly substituted on a carbon atom), wherein R is alkyl, substituted alkyl, aralkyl, substituted aralkyl, aryl, or substituted aryl and R' is optionally substituted alkylene or arylene.

The term "vinyl" can refer to the group —CH=CH$_2$, optionally wherein one or more of the hydrogen atoms is replaced by an alkyl group substituent. Thus, vinyl can refer to substituted or unsubstituted vinyl.

The terms "halo", "halide", or "halogen" as used herein refer to fluoro, chloro, bromo, and iodo groups.

The term "sulfonyl" refers to the —S(=O)$_2$R group, wherein R is alkyl, substituted alkyl, aralkyl, substituted aralkyl, aryl, or substituted aryl.

The term "sulfinyl" refers to the —S(=O)R group, wherein R is alkyl, substituted alkyl, aralkyl, substituted aralkyl, aryl, or substituted aryl.

The term "ester" refers to a compound that comprises the group R'—O—C(=O)—R, wherein R and R' are independently alkyl, cycloalkyl, aralkyl, or aryl, wherein the alkyl, cycloalkyl, aralkyl, or aryl are optionally substituted. The term "esterifying" can refer to forming an ester by contacting a compound containing a carboxylic acid or derivative thereof (e.g., an acid chloride) and a compound containing a hydroxyl group (e.g., an alcohol or a phenol).

The term "lactone" refers to a cyclic ester, wherein an oxygen atom and the carbonyl carbon atom of the ester form part of the backbone of a heterocyclic group.

A dashed line crossed by a wavy line, e.g., in the structure:

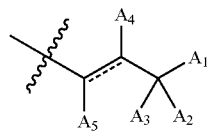

indicates the site where a substituent can bond to another group.

A dashed line representing a bond in a chemical formula indicates that the bond can be either present or absent. For example, the chemical structure:

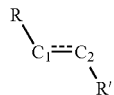

refers to compounds wherein C$_1$ and C$_2$ can be joined by either a single or double bond. The group:

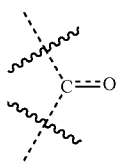

refers to a compound that can include a carbonyl (i.e., C(=O)) or a hydroxyl group. Thus, in the group above, when carbon and oxygen atoms are bonded by a single bond, the oxygen can be protonated.

A wavy line representing a bond in a chemical structure, such as in the structure:

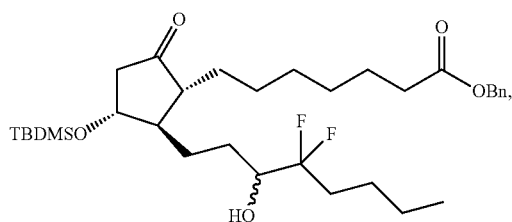 [SMILES: CCCCC(F)(F)C(O)CC[C@H]1[C@H](O[Si](C)(C)C(C)(C)C)CC(=O)[C@@H]1CCCCCCC(=O)OCc1ccccc1]

wherein a wavy line represents the bond between the OH group and the carbon on the di-fluoro-substituted alkyl chain, represents unspecified stereochemistry of the bond, wherein the compound can be a single stereoisomer or a mixture of the two possible stereoisomers. Alternatively, a chiral center having unspecified stereochemistry can be denoted by "*".

The term "nucleophile" refers to a molecule or ion that can form a bond with an electron deficient group (e.g., a carbonyl carbon) by donating one or two electrons. Nucleophiles include, but are not limited to, carbon, oxygen, and sulfur nucleophiles. Exemplary nucleophiles include, water, hydroxide, alcohols (i.e., aromatic and aliphatic alcohols), alkoxides, aryloxides (e.g., phenoxides), thiols (e.g, HS-alkyl, HS-aryl), thiolates (e.g., ⁻S-alkyl and ⁻S-aryl) and amines (e.g., ammonia, primary amines, and secondary amines). Nucleophiles can also be provided as salts, such as, but not limited to, alkali metal salts (i.e., salts comprising an anionic nucleophile, such as an alkoxide, aryloxide, or thiolate, and an alkali metal cation, such as but not limited to a sodium (Na), potassium (K), lithium (Li), calcium (Ca), or cesium (Cs) cation.

The term "amine" refers to a molecule having the formula N(R)$_3$, or a protonated form thereof, wherein each R is independently H, alkyl, substituted alkyl, aryl, substituted aryl, aralkyl, substituted aralkyl, or wherein two R groups together form an alkylene or arylene group. The term "primary amine" refers to an amine wherein at least two R groups are H. The term "secondary amine" refers to an amine wherein only one R group is H. The term "alkylamine" can refer to an amine wherein two R groups are H and the other R group is alkyl or substituted alkyl. "Dialkylamine" can refer to an amine where two R groups are alkyl. "Arylamine" can refer to an amine wherein one R group is aryl. Amines can also be protonated, i.e., have the formula $[NH(R)_3]^+$.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl.

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

The term "hydroxyl protecting group" refers to groups that are known in the art of organic synthesis for masking hydroxyl groups during chemical group transformations elsewhere in the molecule. Accordingly, hydroxyl protecting groups are groups that can replace the hydrogen atom of a hydroxy group on a molecule and that are stable and non-reactive to reaction conditions to which the protected molecule is to be exposed. Suitable hydroxyl protecting groups are described, for example, in Greene and Wuts, Protective Groups in Organic Synthesis, 3$^{rd}$ Edition; New York, John Wiley & Sons, Inc., 1999. Hydroxyl protecting groups include, but are not limited to, groups that can be reacted with hydroxyl groups to form ethers, such as silyl ethers (e.g., trimethylsilyl (TMS), triethylsilyl (TES), tert-butyldimethylsilyl (TBDMS, sometimes also referred to as TBS), t-butyldiphenylsilyl (TBDPS), or phenyldimethylsilyl ethers) substituted methyl ethers (e.g., methoxymethyl (MOM), benzyloxymethyl (BOM), tetrahydropyranyl (THP)), substituted ethyl ethers, benzyl ethers and substituted benzyl ethers; esters (e.g., acetate, formate, chloroacetate); and carbonates. The term "protected hydroxyl" can refer to the group —OR, wherein R is a hydroxyl protecting group.

The term "silyl" refers to groups comprising silicon atoms (Si). In some embodiments, the term silyl refers to the group —$Si(R)_3$, wherein each R is independently alkyl, substituted alkyl, aralkyl, aryl, and substituted aryl. In some embodiments, the term silyl refers to a trialkylsilyl group.

As used herein, the terms "siloxy" and "silyl ether" refer to groups or compounds including a silicon-oxygen (Si—OR) bond and wherein R is an organic group, such as an alkyl or aryl group (i.e., methyl, ethyl, phenyl, etc.).

The term "aprotic solvent" refers to a solvent molecule which can neither accept nor donate a proton. Examples of aprotic solvents include, but are not limited to, ethyl acetate; carbon disulphide; ethers, such as, diethyl ether, tetrahydrofuran (THF), ethylene glycol dimethyl ether, dibutyl ether, diphenyl ether, MTBE, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. Additional aprotic solvents include, for example, acetone, acetonitrile, butanone, butyronitrile, chlorobenzene, chloroform, 1,2-dichloroethane, dimethylacetamide, N,N-dimethylformamide (DMF), dimethylsulfoxide (DMSO), and 1,4-dioxane.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

II. Compounds

The term "prostaglandin" can refer to naturally occurring 20-carbon fatty acid derivatives produced biosynthetically by the oxidative metabolism of fatty acids (e.g., arachidonic acid). In some embodiments, "prostaglandin" can also refer to analogs of the naturally occurring compounds, such as those synthetic analogs that have similar biological effects to the naturally occurring compounds and/or have been used in the pharmaceutical industry. As used herein, the term "analog" is meant to refer to a biologically active, modified version of a natural product, wherein one or more atoms, such as but not limited to carbon, hydrogen, oxygen, nitrogen, sulfur or a halide, have been added or subtracted from the parent structure. The term "prostanoid" refers to naturally occurring prostaglandins and prostaglandin analogs. Thus, "prostanoid" and "prostaglandin" can be used interchangeably herein.

The structures of various known classes of prostaglandins are shown, for example, in U.S. Pat. No. 4,049,648, incorporated herein by reference. For instance, $PGF_\alpha$ prostaglandins and prostaglandin analogs can comprise a cyclopentyl ring carrying two hydroxyl groups in a cis configuration and two side chains in a trans configuration. The side chains can contain carbon-carbon double bonds (i.e., alkene groups) and a variety of substituents. However, the side chains can also be free of alkene groups.

In some embodiments, the term prostaglandin analog refers to an analog of prostaglandin $F_{1\alpha}$ or prostaglandin $F_{2\alpha}$ ($PGF_{2\alpha}$, also referred to by the international nonproprietary name (INN) dinoprost). $PGF_{2\alpha}$ has the following structure:

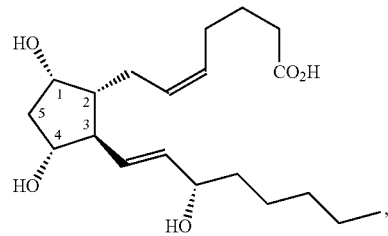 [SMILES: CCCCC[C@H](O)/C=C/[C@@H]1[C@@H](C/C=C\CCCC(=O)O)[C@@H](O)C[C@H]1O]

while prostaglandin $F_{1\alpha}$ has the same structure except lacking the alkene in the side chain attached to carbon 2 of the cyclopentane ring.

In some embodiments, the prostaglandin analog can be a compound including one or more of the following structure changes to the structure of $PGF_{2\alpha}$: one or more hydroxyl group is protected by a protecting group or is replaced by H or =O; one or more methylene units is added to or subtracted from the side chains attached to carbon 2 and/or carbon 3 of the cyclopentane ring; one or more carbon-carbon double bonds are added, subtracted, or relocated; the carboxylic acid group is replaced by a carboxylic acid derivative (e.g., an acid chloride, ester, thioester, amide or anhydride) or by aldehyde, —$CH_2OH$, or methyl; and one or more alkyl group substituents (e.g., halo, amino, alkylamino, arylamino, nitro, thio, thioalkyl, sulfonyl, sulfinyl, alkyl, alkoxy, aryl, aryloxy, aralkyl, or aralkoxy) are added to the side chain at carbon 2 and/or carbon 3 of the cyclopentane ring.

In some embodiments, the prostaglandin or prostaglandin analog can be a compound having the formula:

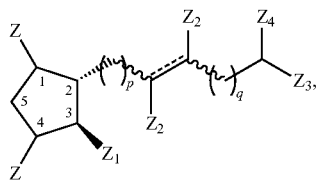

wherein each Z is independently carbonyl or hydroxyl or protected hydroxyl (e.g., wherein the hydroxyl or protected hydroxyl is cis to the side chain at carbon 2); p and q are independently integers between 0 and 10 (i.e., 0, 1, 2, 3, 4, 5, 6, 7, 8, 9, or 10); $Z_1$ is aldehyde, ketone, nitroalkyl, aminoalkyl, thioalkyl, vinyl, or a substituted or unsubstituted alkyl (e.g., a saturated alkyl) or alkenyl; each $Z_2$ is independently selected from H and substituted or unsubstituted alkyl, aralkyl or aryl; $Z_3$ is selected from H, halo, OH, SH, $NH_2$, alkoxy, aryloxy, aralkyloxy, thioalkyl, thioaralkyl, thioaryl, —O-acyl, —NH-alkyl, —NH-aryl, —NH—aralkyl, —NH-sulfonyl-alkyl, —NH-sulfonyl-aryl, —N(alkyl)$_2$, —N(aryl)$_2$, and —N(alkyl)(aryl); and $Z_4$ is =O, OH, or hydrogen. In some embodiments, p and q are each independently integers between 0 and 4. In some embodiments, p is 1 and q is 3.

The presently disclosed subject matter provides, in one aspect, a novel process to produce key compounds that can be used, for example, as prodrugs for prostaglandins or prostaglandin analogs and/or as synthetic intermediates in the synthesis of a wide variety of prostaglandins and prostaglandin analogs, such as, but not limited to, the commercial products bimatoprost, latanoprost, travoprost, sulprostone, tafluprost, unoprostone, prostaglandin $F_{2\alpha}$ ($PGF_{2\alpha}$; also known as dinoprost), carboprost, limaprost, fluprostenol, 13,14-dihydro-15-(2-benzothienyl)-15-pentanor, misoprostol, and cloprostenol. Other prostaglandin analogs that could be provided by the presently disclosed subject matter include, but are not limited to arbaprostil, enisoprost, mexiprostil, dimoxaprost, tiprostanide, and remiprostol as well as other prostaglandin analogues in clinical development.

In some embodiments, the presently disclosed subject matter provides a process (exemplary embodiment outlined in Scheme 1A, below) for the preparation of synthetic intermediates for prostaglandins and prostaglandin analogs, such as compounds having the formula (VIII),

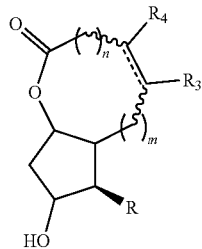

VIII wherein:
  $\text{- - -}$ represents a single or a double bond;
  n and m are independently integers between 1 and 10 or between 0 and 10 (e.g., 0, 1, 2, 3, 4, 5, 6, 7, 8, 9, or 10);

$R_3$ and $R_4$ are independently selected from the group including, but not limited to, H, alkyl, substituted alkyl, aralkyl, substituted aralkyl, aryl, and substituted aryl (which when substituted can include any alkyl or aryl group substituents (e.g., carbonyl or carboxyl)); and R is aldehyde (i.e., —C(=O)H), acyl (e.g., —C(=O)-alkyl), nitroalkyl, aminoalkyl, thioalkyl, vinyl (i.e., —CH=CH$_2$, which can optionally be substituted), or an alkyl or alkenyl of the formula:

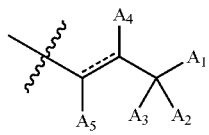

wherein
  $\text{- - -}$ represents a single or a double bond;
  $A_1$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino;
  $A_2$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, provided that $A_2$ is not halogen or amino when $A_1$ or $A_3$ is hydroxyl or amino;
  $A_3$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, provided that $A_3$ is not halogen or amino when $A_1$ or $A_2$ is hydroxyl or amino;
  or two of $A_1$, $A_2$, and $A_3$ together form a ring (e.g., an alkylene group) or =O; and
  $A_4$ and $A_5$ are independently hydrogen, alkyl, cycloalkyl, aryl, aralkyl, acyl, alkoxyl, or aralkoxyl.

In some embodiments, R is alkyl or alkenyl of the formula:

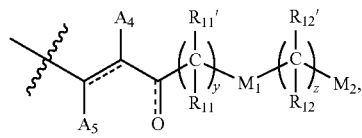

wherein:
  $\text{- - -}$ represents a single or a double bond;
  $A_4$ and $A_5$ are as defined above;
  y and z are independently integers between 0 and 4;
  $R_{11}$ and $R_{11}'$ if present, are each independently selected from H and alkyl;
  $R_{12}$ and $R_{12}'$, if present, are each independently selected from H and alkyl;
  $M_1$ is selected from —O—, —S—, —S(=O)—, —S(=O)$_2$—, —C($R_{13}$)$_2$—, and —C$R_{13}$=C$R_{13}$—, wherein each $R_{13}$, if present, is independently selected from H, alkyl, alkoxyl, or hydroxyl; and $M_2$ is selected from H, cycloalkyl, aryl, and heteroaryl.

When the oxygen atom in the formula for R directly above is bonded to the carbon atom with a single bond, the oxygen atom can be protonated (i.e., one of ordinary skill in the art would understand that there can be an implied H attached to the singly bonded O).

In some embodiments, R is alkyl or alkenyl of the formula:

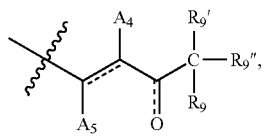

wherein:

--- represents a single or a double bond;

$A_4$ and $A_5$ are as defined above;

$R_9$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino;

$R_9'$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9'$ is not halogen or amino when $R_9$ or $R_9''$ is hydroxyl or amino;

$R_9''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9''$ is not halogen or amino when $R_9$ or $R_9'$ is hydroxyl or amino;

or two or more of $R_9$, $R_9'$, and $R_9''$ together form a ring (e.g., an alkylene group or an aryl or heteroaryl group).

When the oxygen atom in the formula for R directly above is bonded to the carbon atom with a single bond, the oxygen atom can be protonated (i.e., one of ordinary skill in the art would understand that there can be an implied H attached to the singly bonded O).

In some embodiments, one of $R_9$, $R_9'$ and $R_9''$ can have the formula:

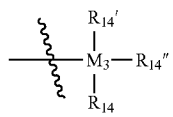

wherein:

$M_3$ is carbon, nitrogen, oxygen or sulfur, and each of $R_{14}$, $R_{14}'$, and $R_{14}''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino, and wherein $R_{14}'$ and/or $R_{14}''$ can be present or absent (e.g., such that when $M_3$ is carbon, the carbon can be mono-, di-, or tri-substituted; when $M_3$ is nitrogen, the nitrogen can be mono- or di-substituted; and when $M_3$ is oxygen or sulfur, the oxygen or sulfur is mono-substituted), and further wherein when one of $R_{14}$, $R_{14}'$, and $R_{14}''$ is hydroxyl or amino, the other two of $R_{14}$, $R_{14}'$ and $R_{14}''$ is not halogen or amino.

In some embodiments, the other two of $R_9$, $R_9'$, and $R_9''$ can be H or alkyl.

In some embodiments, two or three of $R_{14}$, $R_{14}'$ and $R_{14}''$ can be the same or different.

The compound of Formula (VIII) can be transformed into the prostaglandin or prostaglandin analog by opening the lactone ring with a nucleophile to form a ring-opened product and optional additional steps (e.g., reduction of a carbon-carbon double bond, transformation of one carboxylic acid derivative (e.g., an carboxylic acid, ester or amide) into another carboxylic acid derivative; reduction of a carboxylic acid derivative, removal of a protecting group, etc.). The compounds of Formula (VIII) can also be used as prodrugs for prostaglandins or prostaglandin analogs (e.g., wherein the lactone ring opens in vivo).

In some other embodiments, the presently disclosed subject matter provides a process (exemplary embodiment outlined in Scheme 1B, below) for the preparation of synthetic intermediates for prostaglandins and prostaglandin analogs, such as compounds having the formula (XI),

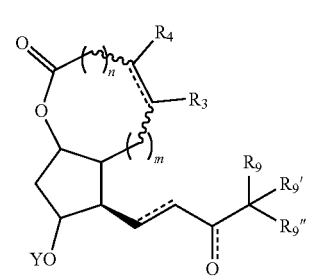

XI wherein:

--- represents a single or a double bond;

Y is H or a hydroxyl protecting group;

n and m are independently integers between 1 and 10 or between 0 and 10;

$R_3$ and $R_4$ are independently selected from the group including, but not limited to, H, alkyl, substituted alkyl (e.g., carbonyl- or carboxyl-substituted alkyl), aralkyl, substituted aralkyl, aryl, and substituted aryl;

$R_9$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino;

$R_9'$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9'$ is not halogen or amino when $R_9$ or $R_9''$ is hydroxyl or amino;

$R_9''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9''$ is not halogen or amino when $R_9$ or $R_9'$ is hydroxyl or amino;

or two or more of $R_9$, $R_9'$, and $R_9''$ together form a ring (e.g., an alkylene group or an aryl or heteroaryl group).

If the singly or doubly bonded oxygen in Formula (XI) is singly bonded, it can be protonated.

In some embodiments, the singly or doubly bounded oxygen is doubly bonded, such that the side chain on the lower right-hand side of Formula (XI) contains a ketone.

In some embodiments, one of $R_9$, $R_9'$ and $R_9''$ can have the formula:

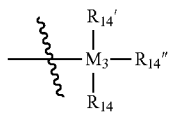

wherein:

$M_3$ is carbon, nitrogen, oxygen or sulfur, and each of $R_{14}$, $R_{14}'$, and $R_{14}''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino, and wherein $R_{14}'$ and/or $R_{14}''$ can be present or absent, further wherein when one of $R_{14}$, $R_{14}'$, and $R_{14}''$ is hydroxyl or amino, the other two of $R_{14}$, $R_{14}'$ and $R_{14}''$ is not halogen or amino. In some embodiments, two or three of $R_{14}$, $R_{14}$, and $R_{14}''$ can be the same or different. In some embodiments, the other two of $R_9$, $R_9'$, and $R_9''$ can be H or alkyl.

The compound of Formula (XI) can be transformed into the prostaglandin or prostaglandin analog by enantioselectively reducing a carbonyl group (e.g., if there is a ketone group present on the side chain on the lower right-hand side of the formula structure), and/or deprotecting hydroxy group(s), and/or opening the lactone ring with a nucleophile to form a ring-opened product, and optional additional steps (e.g., reduction of a carbon-carbon double bond, transformation of one carboxylic acid derivative (e.g., an carboxylic acid, ester or amide) into another carboxylic acid derivative; reduction of a carboxylic acid derivative, removal of a protecting group, etc.). The compounds of Formula (XI) can also be used as prodrugs for prostaglandins or prostaglandin analogs (e.g., wherein the lactone ring opens in vivo).

In some other embodiments, the presently disclosed subject matter provides a process (exemplary embodiment outlined in Scheme 1B, below) for the preparation of synthetic intermediates for prostaglandins and prostaglandin analogs, such as compounds having the formula (XII):

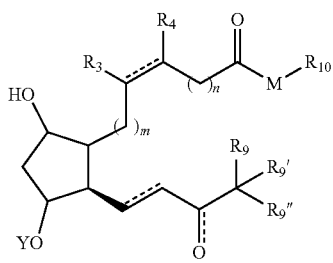

wherein:

--- represents a single or a double bond;

Y, n, m, $R_3$, $R_4$, $R_9$, $R_9'$, and $R_9''$ are as defined for Formula (XI);

M is oxygen, nitrogen, or sulfur; and $R_{10}$ is hydrogen, alkyl, substituted alkyl, cycloalkyl, substituted cycloalkyl, aryl, substituted aryl, aralkyl, substituted aralkyl, alkylacyl, hydroxyacyl, alkoxyacyl, aminoacyl, alkylaminoacyl, or alkylthioacyl.

If the singly or doubly bonded oxygen atom of Formula (XII) is singly bonded, the oxygen atom can be protonated. In some embodiments, the singly or doubly bonded oxygen of Formula (XII) is doubly bonded.

In some embodiments, one of $R_9$, $R_9'$ and $R_9''$ can have the formula:

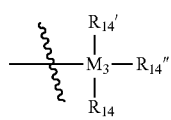

wherein:

$M_3$ is carbon, nitrogen, oxygen or sulfur, and each of $R_{14}$, $R_{14}'$, and $R_{14}''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino, and wherein $R_{14}'$ and/or $R_{14}''$ can be present or absent, further wherein when one of $R_{14}$, $R_{14}'$, and $R_{14}''$ is hydroxyl or amino, the other two of $R_{14}$, $R_{14}'$ and $R_{14}''$ is not halogen or amino.

In some embodiments, the other two of $R_9$, $R_9'$, and $R_9''$ can be H or alkyl.

The compound of Formula (XII) can be transformed into the prostaglandin or prostaglandin analog by enantioselectively reducing the carbonyl group of the side chain ketone, if present and where needed, and/or deprotecting hydroxyl group(s), and optional additional steps (e.g., reduction of a carbon-carbon double bond, transformation of one carboxylic acid derivative (e.g., an carboxylic acid, ester or amide) into another carboxylic acid derivative; reduction of a carboxylic acid derivative, removal of a protecting group, etc.).

In some embodiments, the presently disclosed subject matter provides compounds of Formulae (II), (III), (IV), (V), (V-A), (VI), (VI-A), (VII), (IX), and (X) also depicted in Scheme 1A below.

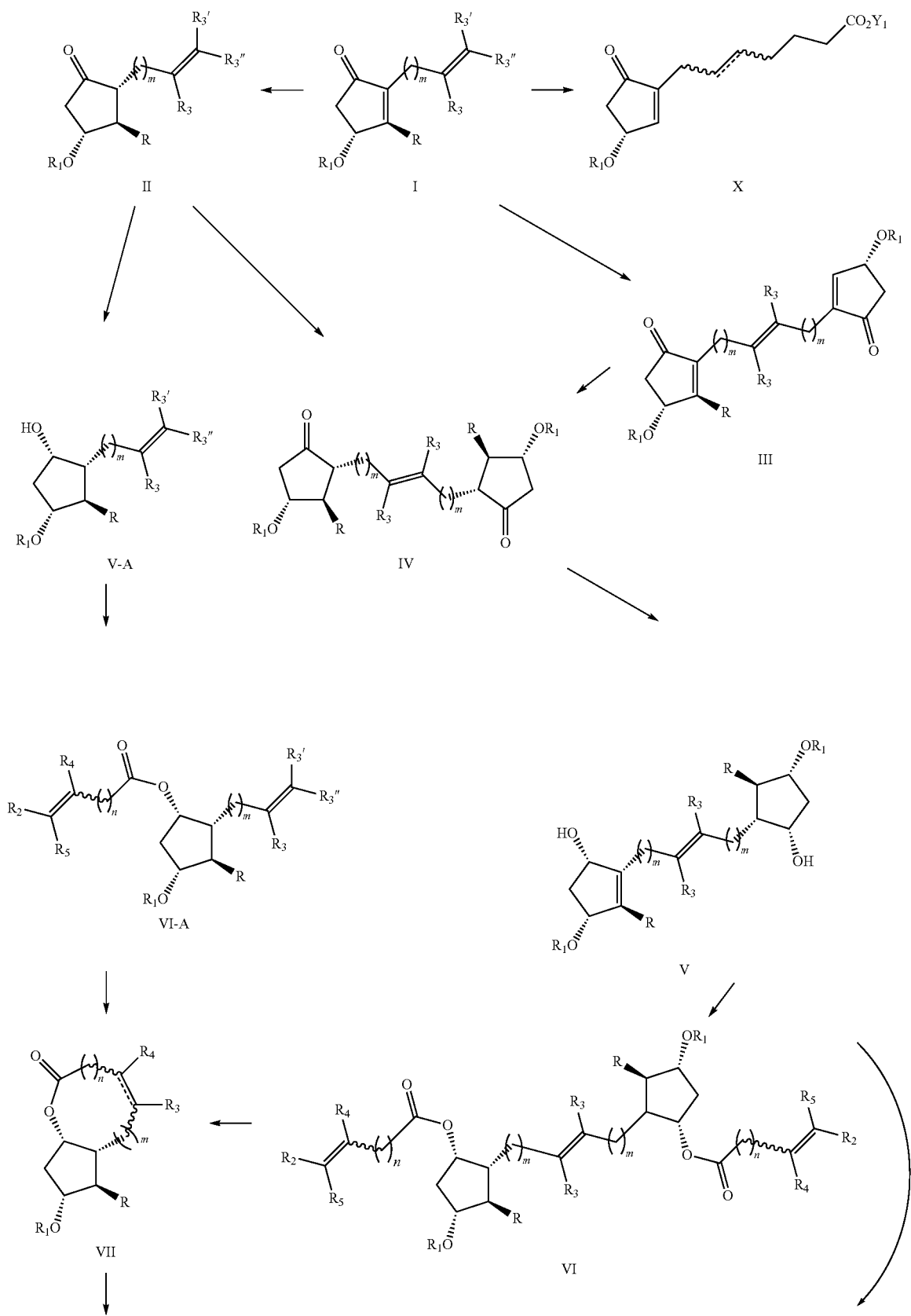
Scheme 1A. Synthesis of Prostaglandin intermediates via metathesis strategy.

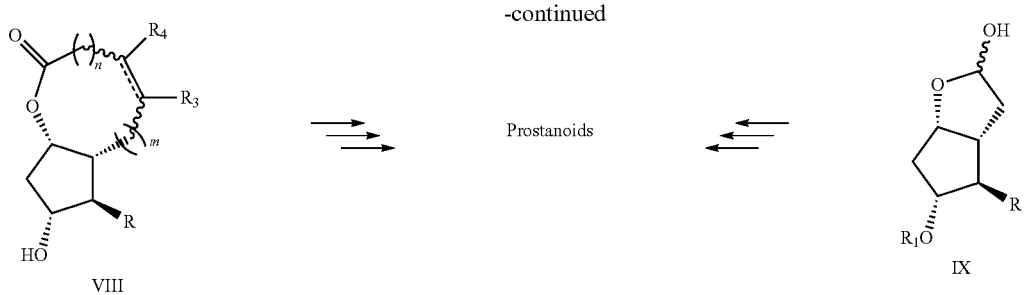
In some embodiments, the presently disclosed subject matter provides compounds of Formulae (XI), (XII), (XIII), (XIV), (XV), and (XVI) also depicted in Scheme 1B below.
Scheme 1B. Synthesis of Prostaglandin intermediates and prostaglandins from lactones (VIII-5A) & (VIII-6) via metathesis strategy.
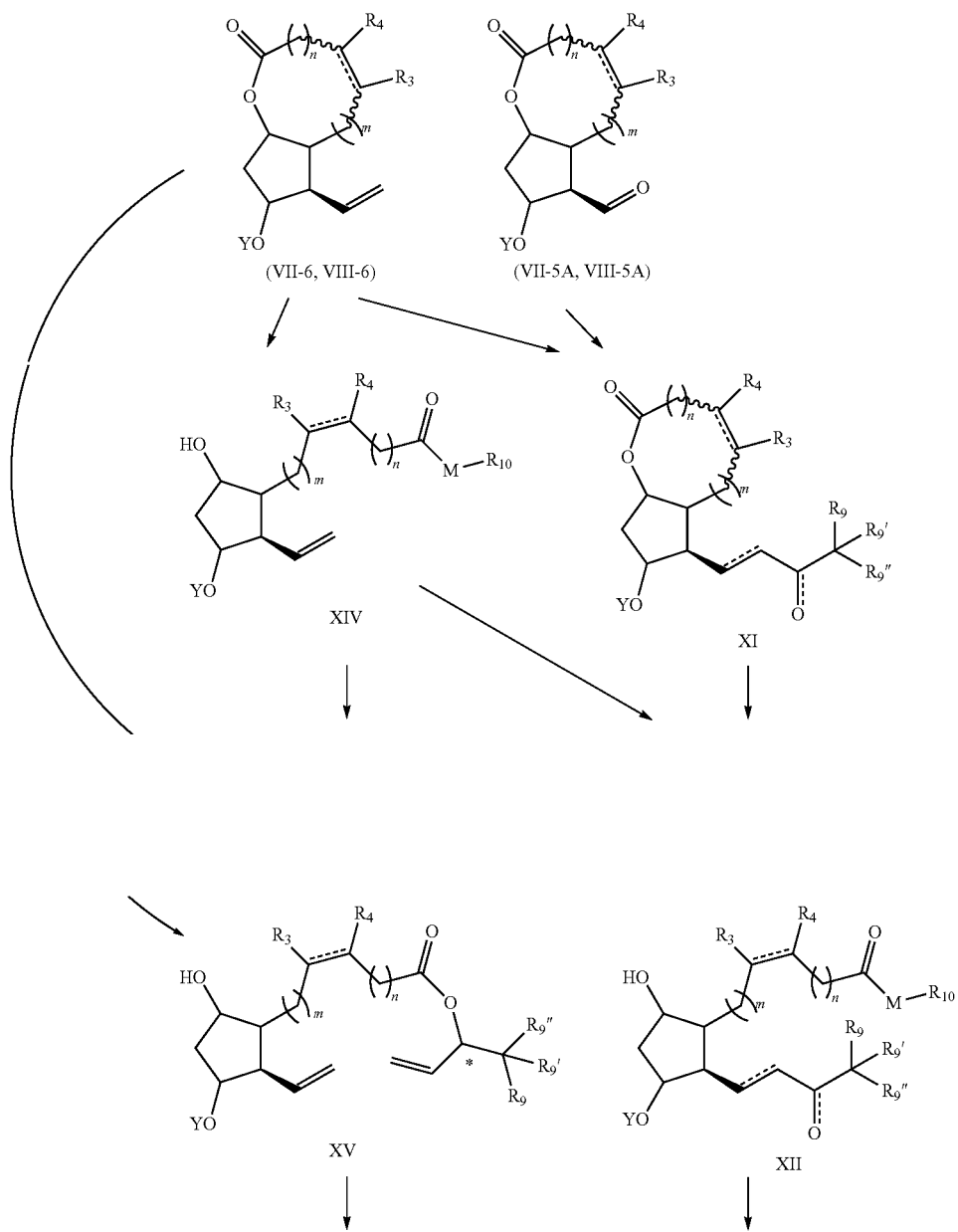

-continued

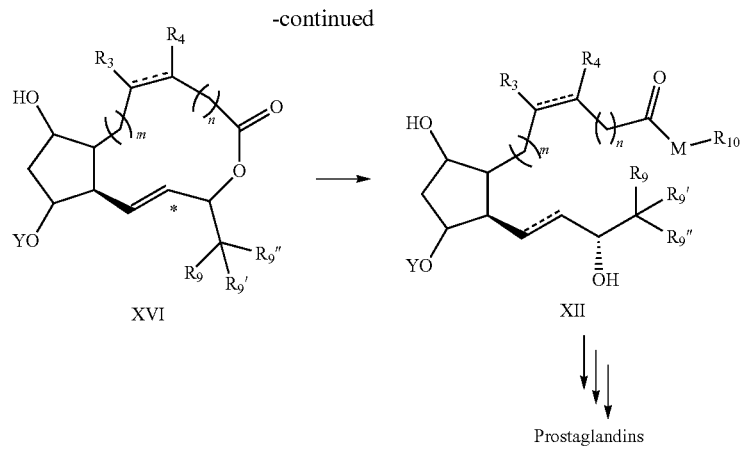

XVI → XII

Prostaglandins

In Scheme 1B, above, Y can generally be a hydroxyl protecting group or H, with the exception that for Formulae (VII-6) and (VII-5A), Y is a hydroxyl protecting group and for Formulae (VIII-6) and (VIII-5A), Y is H. The "*" indicates a chiral center, which can be racemic or enantiomerically pure. The compounds of Formulae (VII-6) and (VIII-6) can be compounds of Formulae (VII) and (VIII) of Scheme 1A wherein R is unsubstituted vinyl. The compounds of Formulae (VII-5A) and (VIII-5A) can be compounds of Formulae (VII) and (VIII) of Scheme 1A wherein R is aldehyde.

The aforementioned compounds have commercial utility in the synthesis of pharmaceuticals, particularly in the prostaglandin field. Several of these intermediates are crystalline in nature and, therefore, provide purification opportunities via conventional crystallization as compared to the commonly practiced chromatographic purifications of prior, generally oily, prostaglandin intermediates.

II.A. Compounds of Formula (II)

In some embodiments, the presently disclosed subject matter provides a compound of Formula (II):

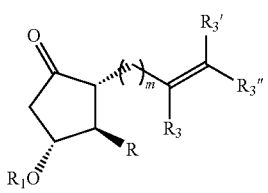

II wherein m is an integer between 0 and 10;

R is as defined hereinabove with regard to the compounds of Formula (VIII) or as below for the compounds of Formula (IV);

$R_1$ is independently H or a hydroxyl protecting group and $R_3$, $R_3'$, and $R_3''$ are independently selected from the group comprising, but not limited to, H, alkyl, substituted alkyl, aralkyl, substituted aralkyl, aryl, substituted aryl, alkoxyl, aralkoxyl, and acyloxyl. The alkyl and/or aryl group substituents, if present, can be, for example, but are not limited to, carbonyl and carboxyl.

In some embodiments, $R_3$ is selected from the group comprising, but not limited to, H, alkyl, substituted alkyl, aralkyl, substituted aralkyl, aryl, and substituted aryl; and at least one of $R_3'$ and $R_3''$ is selected from the group including, but not limited to, alkyl, substituted alkyl, aralkyl, substituted aralkyl, aryl, substituted aryl, alkoxyl, aralkoxyl, and acyloxyl. Exemplary substituted alkyl and/or substituted aryl include, but are not limited to, carbonyl- and carboxyl-substituted alkyl and/or aryl.

In some embodiments, at least one of $R_3'$ and $R_3''$ is other than H. In some embodiments, one, two or all three of $R_3$, $R_3'$, and $R_3''$ are H or alkyl, so long as not all three are H at the same time.

In some embodiments, m is an integer between 0 and 4. In some embodiments, each m is the same. In some embodiments, m is 1.

In some embodiments, $R_1$ is a hydroxyl protecting group. $R_1$ can be any suitable hydroxyl protecting group. For example, suitable hydroxyl protecting groups include, but are not limited to silyl protecting groups (e.g., TMS, TES, TBDMS, TBDPS, and phenyldimethylsilyl); substituted methyl ethers (e.g., MOM, BOM, and THP); substituted ethyl ethers; benzyl ethers and substituted benzyl ethers; esters (e.g., acetate, formate, chloroacetate); and carbonates. In some embodiments, $R_1$ is a silyl group (e.g., TMS, TES, TBDMS, TBDPS and the like), such that the molecule of Formula (II) includes a silyl ether. In some embodiments, $R_1$ is TBDMS. In some embodiments, $R_1$ is ethoxyethyl. In some embodiments, $R_1$ is other than dinitrobenzoyl or TMS.

II.B. Compounds of Formula (III)

In some embodiments, the presently disclosed subject matter provides a compound of Formula (III):

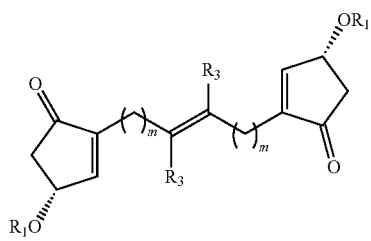

III wherein each m is an integer between 0 and 10; each $R_1$ is independently H or a hydroxyl protecting group; and each $R_3$ is independently as described for the compounds of Formula (II) and/or is selected from the group comprising, but not limited to, H, alkyl, substituted alkyl, aralkyl, substituted aralkyl, aryl, and substituted aryl. Exemplary alkyl and/or aryl group substituents, if present, include, but are not limited to, carbonyl and carboxyl.

In some embodiments, one or both $R_3$ is H or alkyl. In some embodiments, both $R_1$ groups are the same. In some embodiments, both $R_3$ groups are the same. In some embodiments, the compound of Formula (III) can be prepared by an intermolecular metathesis reaction of two molecules of the same chiral allylcyclopentenone. However, in some embodiments, the compound of Formula (III) can be prepared by an intermolecular metathesis reaction of two different chiral allylcyclopentenones. In some embodiments, the compound of Formula (III) is crystalline.

In some embodiments, m is an integer between 0 and 4. In some embodiments, each m is the same. In some embodiments, m is 1.

In some embodiments, $R_1$ is a hydroxyl protecting group. $R_1$ can be any suitable hydroxyl protecting group. For example, suitable hydroxyl protecting groups include, but are not limited to silyl protecting groups (e.g., TMS, TES, TBDMS, TBDPS, and phenyldimethylsilyl); substituted methyl ethers (e.g., MOM, BOM, and THP); substituted ethyl ethers; benzyl ethers and substituted benzyl ethers; esters (e.g., acetate, formate, chloroacetate); and carbonates. In some embodiments, $R_1$ is a silyl group (e.g., TMS, TES, TBDMS, TBDPS and the like), such that the molecule of Formula (III) includes a silyl ether. In some embodiments, $R_1$ is TBDMS or ethoxyethyl. In some embodiments, $R_1$ is other than dinitrobenzoyl or TMS.

II.C. Compounds of Formula (IV)

In some embodiments, the presently disclosed subject matter provides a compound of Formula (IV):

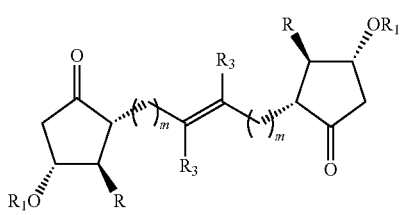

IV wherein m, $R_1$, and $R_3$ are as defined above for the compounds of Formula (III); and each R is independently selected from the group comprising aldehyde, ketone, acyl, nitroalkyl, aminoalkyl, thioalkyl, vinyl, and alkyl or alkenyl of the formula:

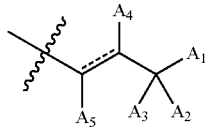

wherein

═══ represents a single or a double bond;

$A_1$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino;

$A_2$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, provided that $A_2$ is not halogen or amino when $A_1$ or $A_3$ is hydroxyl or amino;

$A_3$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, provided that $A_3$ is not halogen or amino when $A_1$ or $A_2$ is hydroxyl or amino;

or wherein two of $A_1$, $A_2$, and $A_3$ together form a ring (e.g., an alkylene group) or ═O; and $A_4$ and $A_5$ are independently hydrogen, alkyl, substituted alkyl, cycloalkyl, substituted cycloalkyl, aryl, substituted aryl, aralkyl, substituted aralkyl, acyl, alkoxyl, or aralkoxyl. The alkyl or alkenyl R group can be attached to the cyclopentanone ring via a bond between the ring and the carbon directly attached to $A_5$ (as indicated by the dotted line crossed by the wavy line).

In some embodiments, each m is 1. In some embodiments, both $R_1$ and/or both $R_3$ are the same. In some embodiments, the compound of Formula (IV) is crystalline.

In some embodiments, both R groups are the same. In some embodiments, R is alkyl or alkenyl of the formula:

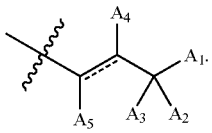

In some embodiments, one or both of $A_4$ and $A_5$ are H. In some embodiments, $A_1$, $A_2$, and $A_3$ are independently selected from H, hydroxyl, protected hydroxyl, alkyl, substituted alkyl (e.g., aryloxyl-substituted methyl or substituted aryloxyl-substituted methyl), aralkyl, substituted aralkyl, aryl (e.g., heteroaryl), substituted aryl, thiophenyl, benzothiophenyl, and halo; or wherein two of $A_1$, $A_2$, and $A_3$ together from a ring or ═O.

In some embodiments, R is selected from the group comprising those shown in Table 1, below, and/or an R group of another alkyl or alkenyl formula as described herein. In some embodiments, R can be another side chain of a commercial prostaglandin analog, optionally including one or more protecting groups (e.g., one or more hydroxyl protecting groups) or another side chain of a prostaglandin analog previously described in the art. For example, R can be a side chain as described for Formula (II) of U.S. Patent Application Publication No. 2010/0105771 or as described in U.S. Patent Application Publication 2007/0254920, both of which are encorporated herein by reference their entirety.

TABLE 1

Exemplary Stuctures for Side Chain R.

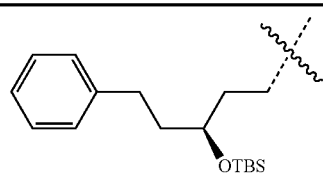

1

TABLE 1-continued

Exemplary Structures for Side Chain R.

| | |
|---|---|
| 2 | 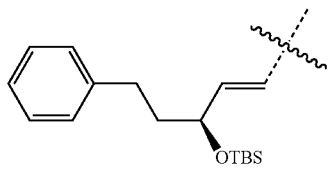 |
| 3 | 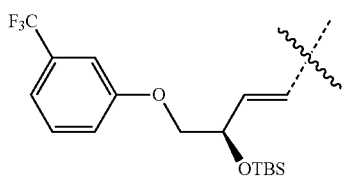 |
| 4 | 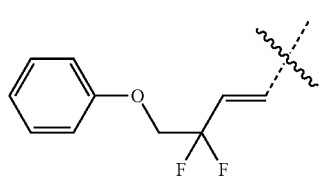 |
| 5 |  |
| 6 | 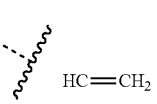 |
| 7 | 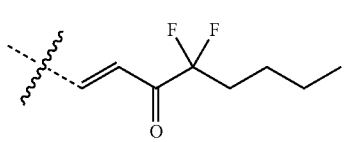 |
| 8 | 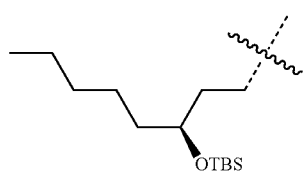 |
| 9 | 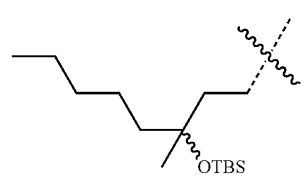 |
| 10 | 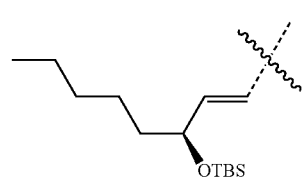 |
| 11 | 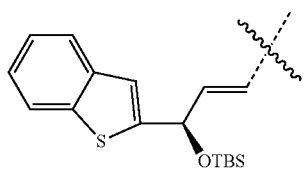 |
| 12 | 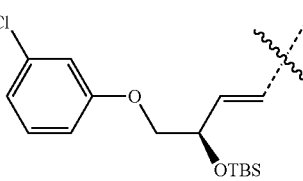 |
| 13 | 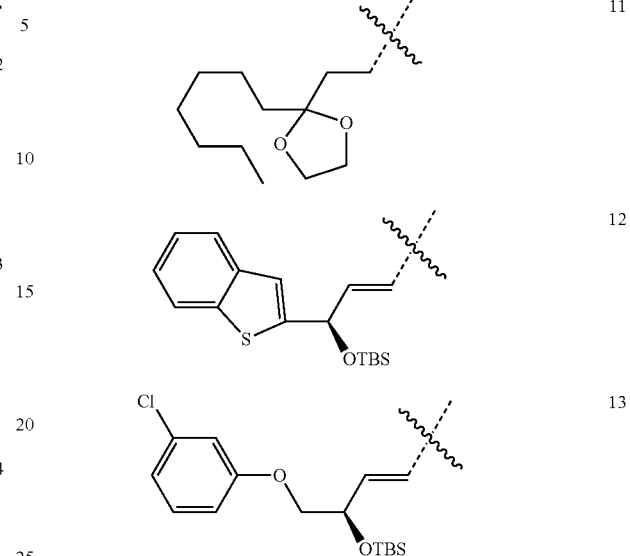 |

II.D. Compounds of Formula (V)

In some embodiments, the presently disclosed subject matter provides a compound of Formula (V):

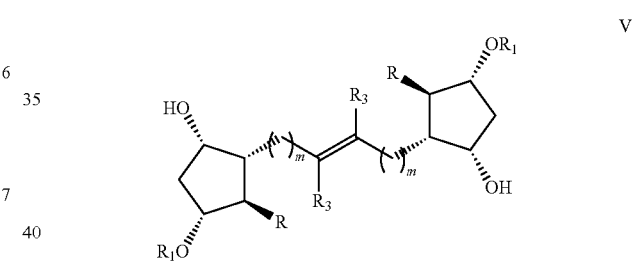

wherein m, R, $R_1$, and $R_3$ are as defined above for the compounds of Formulae (III) and (IV). In some embodiments, the compound of Formula (V) is crystalline.

II.E. Compounds of Formula (V-A)

In some embodiments, the presently disclosed subject matter provides a compound of Formula (V-A):

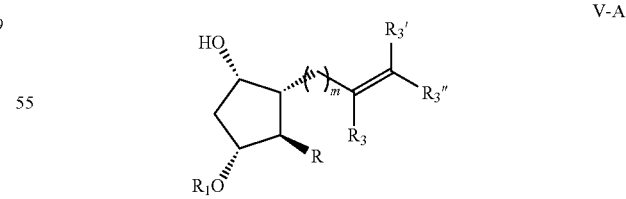

wherein m, R, and $R_1$ are as defined above for the compounds of Formulae (III) and (IV), and $R_3$, $R_3'$, and $R_3''$ are independently selected from the group comprising, but not limited to, H, alkyl, substituted alkyl, aralkyl, substituted aralkyl, aryl, substituted aryl, alkoxyl, aralkoxyl, and acyloxyl. Exemplary alkyl and/or aryl group substituents, if present, include, but are not limited to, carbonyl and carboxyl.

In some embodiments, $R_3$ is selected from the group comprising, but not limited to, H, alkyl, substituted alkyl, aralkyl, substituted aralkyl, aryl, and substituted aryl. In some embodiments, at least one of $R_3'$ and $R_3''$ is other than H. Thus, optionally at least one of $R_3'$, and $R_3''$ are selected from the group including, but not limited to, alkyl, substituted alkyl, aralkyl, substituted aralkyl, aryl, substituted aryl, alkoxyl, aralkoxyl, and acyloxyl.

II.F. Compounds of Formula (VI)

In some embodiments, the presently disclosed subject matter provides a compound of Formula (VI):

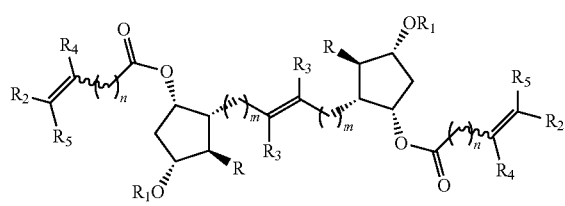

VI wherein m, R, $R_1$, and $R_3$ are as defined above for the compounds of Formulae (III)-(V); each n is an integer between 0 and 10; and each $R_2$, $R_4$, and $R_5$ is independently selected from the group including, but not limited to, H, alkyl, substituted alkyl, aralkyl, substituted aralkyl, aryl, and substituted aryl. Exemplary alkyl and/or aryl group substituents, if present, include, but are not limited to, carbonyl and carboxyl.

In some embodiments, each n is an integer between 0 and 4. In some embodiments, each n is 2 or 3. In some embodiments, each n is the same. In some embodiments, each n is 3.

In some embodiments, each m is 1. In some embodiments, both $R_1$ and/or both $R_3$ are the same. In some embodiments, both R groups are the same and/or are alkyl or alkenyl of the formula:

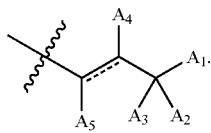

In some embodiments, each $R_2$ and/or each $R_4$ and/or each $R_5$ are the same. In some embodiments, $R_2$, $R_4$, and $R_5$ are H or alkyl. In some embodiments, $R_2$, $R_4$, and $R_5$ are H. In other embodiments, at least one of $R_2$, $R_4$, and $R_5$ is other than H. In some embodiments, the compound of Formula (VI) is crystalline.

II.G. Compounds of Formula (VI-A)

In some embodiments, the presently disclosed subject matter provides a compound of Formula (VI-A):

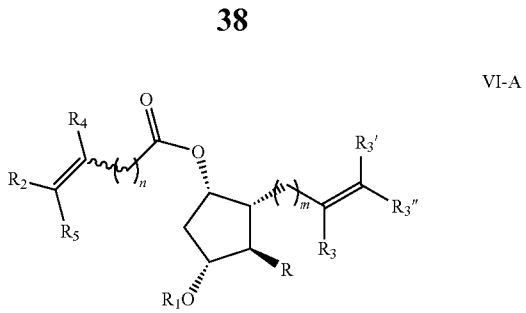

VI-A wherein
m, R, and $R_1$, are as defined above for the compounds of Formulae (III)-(V);
each n is an integer between 0 and 10;
each $R_2$, $R_4$, and $R_5$ are independently selected from the group including, but not limited to, H, alkyl, substituted alkyl, aralkyl, substituted aralkyl, aryl, and substituted aryl; and
$R_3$, $R_3'$, and $R_3''$ are independently selected from the group comprising, but not limited to, H, alkyl, substituted alkyl, aralkyl, substituted aralkyl, aryl, substituted aryl, alkoxyl, aralkoxyl, and acyloxyl.

In some embodiments, $R_3$ is selected from the group comprising, but not limited to, H, alkyl, substituted alkyl, aralkyl, substituted aralkyl, aryl, and substituted aryl. In some embodiments, at least one of $R_3'$ and $R_3''$ is other than H. Thus, optionally at least one of $R_3'$, and $R_3''$ is selected from the group including, but not limited to, alkyl, substituted alkyl, aralkyl, substituted aralkyl, aryl, substituted aryl, alkoxyl, aralkoxyl, and acyloxyl. In some embodiments, one of $R_3'$ and $R_3''$ is alkyl.

In some embodiments, each n is an integer between 0 and 4. In some embodiments, each n is 2 or 3. In some embodiments, each n is the same. In some embodiments, each n is 3.

In some embodiments, each $R_2$ and/or each $R_4$ and/or each $R_5$ are the same. In some embodiments, $R_2$, $R_4$, and $R_5$ are H or alkyl. In some embodiments, $R_2$, $R_4$, and $R_5$ are H. In other embodiments, at least one of $R_2$, $R_4$, and $R_5$ is other than H. In some embodiments, $R_2$ is other than H.

II.H. Compounds of Formula (VII) and Formula (VIII)

In some embodiments, the presently disclosed subject matter provides a compound of Formula (VII) and/or Formula (VIII). Compounds of Formula (VII) can have a structure:

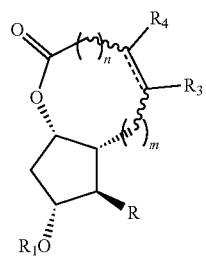

VII wherein
═══ represents a single or a double bond; and
n, m, R, $R_1$, $R_3$, and $R_4$ are as defined above for the compounds of Formulae (III)-(VI).

In some embodiments, the sum of m and n is 3 or 4, such that the compound of Formula (VII) is a ten- or nine-membered lactone.

In some embodiments, $R_1$ is a hydroxyl protecting group. In some embodiments, i.e., when $R_1$ is H, the compound of Formula (VII) can also be a compound of Formula (VIII):

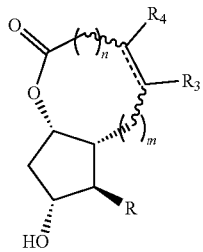

VIII wherein

╍╍╍ represents a single or a double bond; and m, n, R, $R_3$, and $R_4$ are as defined above for the compounds of Formulae (III)-(VI).

In some embodiments, the sum of m and n is 3 or 4, such that the compound of Formula (VIII) is a ten- or nine-membered lactone.

In some embodiments, R for the compounds of Formulae (VII) and (VIII) can be aldehyde, nitroalkyl, —$CH_2NO_2$, or —CH═$CH_2$. In some embodiments, R can comprise a ketone. In some embodiments, R can comprise a benzothiophenyl group, optionally wherein R comprises an alkyl or alkenyl group of the formula:

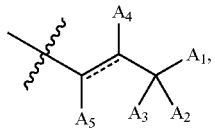

wherein one of $A_1$, $A_2$, and $A_3$ is benzothiophenyl. In some embodiments, R is alkyl or alkenyl and two of $A_1$, $A_2$, and $A_3$ are ═O and the remaining $A_1$, $A_2$, and $A_3$ group is other than a phenoxyalkyl or a substituted phenoxyalkyl group.

In some embodiments, $R_1$ is H, ethoxyethyl, or TBDMS and/or is other than dinitrobenzoyl or TMS.

II.I. Compounds of Formula (XI)

In some embodiments, the presently disclosed subject matter provides a novel compound of formula (XI):

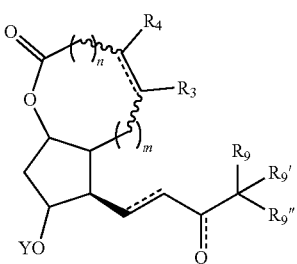

XI wherein

╍╍╍ represents a single or a double bond;

m, n, $R_3$, and $R_4$ are as defined above for the compounds of Formulae (III)-(VI);

$R_9$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, furyl, pyranyl, thioalkyl, thioaralkyl, thioaryl, thiophenyl, benzothiophenyl, halogen, hydroxyl, protected hydroxyl, or amino;

$R_9'$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, furyl, pyranyl, thioalkyl, thioaralkyl, thioaryl, thiophenyl, benzothiophenyl, halogen, hydroxyl, protected hydroxyl, or amino, provided that $R_9'$ is not halogen or amino when $R_9$ or $R_9''$ is hydroxyl or amino;

$R_9''$ is hydrogen, alkyl, substituted alkyl, cycloalkyl, substituted cycloalkyl vinyl, aryl, substituted aryl, aralkyl, substituted aralkyl, acyl, alkoxyl, aralkoxyl, substituted aralkoxyl, aryloxyl, furyl, pyranyl, thioalkyl, thioaralkyl, thioaryl, thiophenyl, benzothiophenyl, halogen, hydroxyl, protected hydroxyl, or amino, provided that $R_9''$ is not halogen or amino when $R_9$ or $R_9'$ is hydroxyl or amino;

or two or more of $R_9$, $R_9'$, and $R_9''$ together form a ring (e.g., an alkylene group or an aryl or heteroaryl group); and Y is hydrogen or a hydroxyl protecting group.

In some embodiments, one of $R_9$, $R_9'$ and $R_9''$ can have the formula:

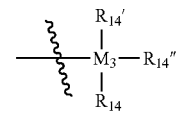

wherein:

$M_3$ is carbon, nitrogen, oxygen or sulfur, and each of $R_{14}$, $R_{14}'$, and $R_{14}''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino, and wherein $R_{14}'$ and/or $R_{14}''$ can be present or absent, further wherein when one of $R_{14}$, $R_{14}'$, and $R_{14}''$ is hydroxyl or amino, the other two of $R_{14}$, $R_{14}'$ and $R_{14}''$ is not halogen or amino. In some embodiments, two or three of $R_{14}$, $R_{14}'$, and $R_{14}''$ can be the same or different.

In some embodiments, the singly or doubly bonded oxygen atom of Formula (XI) is doubly bonded. However, when the singly or doubly bonded oxygen atom is singly bonded, it can be protonated.

In some embodiments, the sum of m and n is 3 or 4, such that the compound of Formula (XI) is a ten- or nine-membered lactone.

In some embodiments, the —C($R_9$)($R_9'$)($R_9''$) group of the compound of Formula (XI) (or of the compound of Formula (XII), (XIII), (XV), and/or (XVI)) can be replaced by the group:

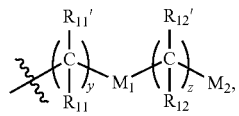

wherein:

y and z are independently integers between 0 and 4 (i.e., 0, 1, 2, 3, or 4);

$R_{11}$ and $R_{11}'$ if present, are each independently selected from H and alkyl;

$R_{12}$ and $R_{12}'$, if present, are each independently selected from H and alkyl;

$M_1$ is selected from —O—, —S—, —S(=O)—, —S(=O)$_2$—, —C($R_{13}$)$_2$—, and —C$R_{13}$=C$R_{13}$—, wherein each $R_{13}$, if present, is independently selected from H, alkyl, alkoxyl, or hydroxyl; and $M_2$ is selected from H, cycloalkyl, aryl, and heteroaryl.

II.J. Compounds of Formula (XII)

In some embodiments, the presently disclosed subject matter provides a compound of Formula (XII):

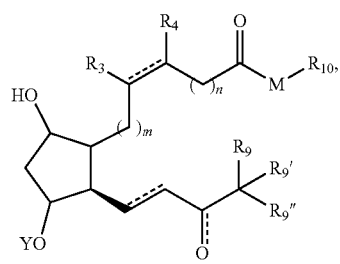

XII wherein $==$, m, n, Y, $R_3$, $R_4$, $R_9$, $R_9'$ and $R_9''$ are as described above for the compound of Formula (XI); M is oxygen, sulfur or nitrogen; and $R_{10}$ is selected from the group comprising hydrogen, alkyl, substituted alkyl, cycloalkyl, substituted cycloalkyl, aryl, substituted aryl, aralkyl, substituted aralkyl, alkylacyl, hydroxyacyl, alkoxyacyl, aminoacyl, alkylaminoacyl, or alkylthioacyl. Optionally, one of $R_9$, $R_9'$ and $R_9''$ is -$M_3(R_{14})(R_{14}')(R_{14}'')$, wherein $M_3$ is carbon, nitrogen, oxygen or sulfur; and each of $R_{14}$, $R_{14}'$, and $R_{14}''$ is independently hydrogen, alkyl, substituted alkyl, cycloalkyl, substituted alkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino; wherein $R_{14}'$ and/or $R_{14}''$ can be present or absent and/or further wherein when one of $R_{14}$, $R_{14}'$, and $R_{14}''$ is hydroxyl or amino, the other two of $R_{14}$, $R_{14}'$ and $R_{14}''$ is not halogen or amino.

II.K. Compounds of Formula (XIII)

In some embodiments, the presently disclosed subject matter provides a compound of Formula (XIII):

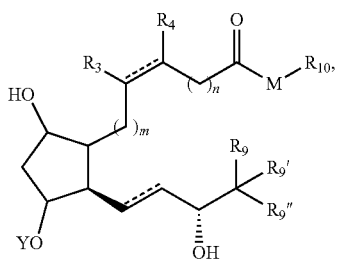

XIII wherein $==$, m, n, Y, $R_3$, $R_4$, $R_9$, $R_9'$ and $R_9''$ are as described above for the compound of Formula (XI); and M and $R_{10}$ are as described above for the compound of Formula (XII). Optionally, one of $R_9$, $R_9'$ and $R_9''$ is -$M_3(R_{14})(R_{14}')(R_{14}'')$, wherein $M_3$ is carbon, nitrogen, oxygen or sulfur; and each of $R_{14}$, $R_{14}'$, and $R_{14}''$ is independently hydrogen, alkyl, substituted alkyl, cycloalkyl, substituted alkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino; wherein $R_{14}'$ and/or $R_{14}''$ can be present or absent and/or further wherein when one of $R_{14}$, $R_{14}'$, and $R_{14}''$ is hydroxyl or amino, the other two of $R_{14}$, $R_{14}'$ and $R_{14}''$ is not halogen or amino.

II.L. Compounds of Formula (XIV)

In some embodiments, the presently disclosed subject matter provides a compound of Formula (XIV):

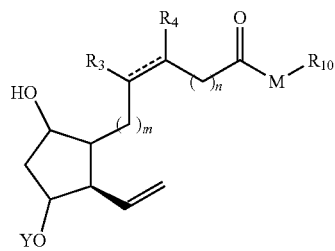

XIV wherein:

$==$ represents a single or a double bond;

m, n, $R_3$, and $R_4$ are as defined above for the compounds of Formulae (III)-(VI);

Y is hydrogen or a hydroxyl protecting group;

M is oxygen, nitrogen, or sulfur; and $R_{10}$ is hydrogen, alkyl, substituted alkyl, cycloalkyl, substituted cycloalkyl, aryl, substituted aryl, aralkyl, substituted aralkyl, alkylacyl, hydroxyacyl, alkoxyacyl, aminoacyl, alkylaminoacyl, or alkylthioacyl.

In some embodiments, the sum of m and n is 3 or 4.

II.M. Compounds of Formula (XV)

In some embodiments, the presently disclosed subject matter provides a compound of formula (XV):

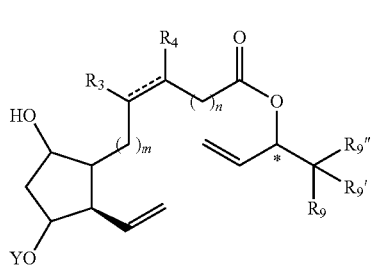

XV wherein

* represents a chiral center, which can be racemic or enationmerically pure;

$==$ represents a single or a double bond;

m, n, $R_3$, and $R_4$ are as defined above for the compounds of Formulae (III)-(VI);

Y is H or a hydroxyl protecting group;

$R_9$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino;

$R_9'$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9'$ is not halogen or amino when $R_9$ or $R_9''$ is hydroxyl or amino;

$R_9''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9''$ is not halogen or amino when $R_9$ or $R_9'$ is hydroxyl or amino;

or two or more of $R_9$, $R_9'$, and $R_9''$ together form a ring (e.g., an alkylene group or an aryl or heteroaryl group).

In some embodiments, the sum of m and n is 3 or 4.

Optionally, one of $R_9$, $R_9'$ and $R_9''$ is -$M_3(R_{14})(R_{14}')$ $(R_{14}'')$, wherein $M_3$ is carbon, nitrogen, oxygen or sulfur; and each of $R_{14}$, $R_{14}'$, and $R_{14}''$ is independently hydrogen, alkyl, substituted alkyl, cycloalkyl, substituted alkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino; wherein $R_{14}'$ and/or $R_{14}''$ can be present or absent and/or further wherein when one of $R_{14}$, $R_{14}'$, and $R_{14}''$ is hydroxyl or amino, the other two of $R_{14}$, $R_{14}'$ and $R_{14}''$ is not halogen or amino.

II.N. Compounds of Formula (XVI)

In some embodiments, the presently disclosed subject matter provides a compound of formula (XVI):

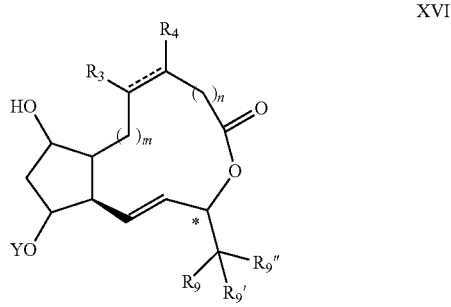

XVI wherein

* represents a chiral center, which can be racemic or enatiomerically pure;

≕ represents a single or a double bond;

m, n, $R_3$, and $R_4$ are as defined above for the compounds of Formulae (III)-(VI);

Y is H or a hydroxyl protecting group;

$R_9$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino;

$R_9'$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9'$ is not halogen or amino when $R_9$ or $R_9''$ is hydroxyl or amino;

$R_9''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9''$ is not halogen or amino when $R_9$ or $R_9'$ is hydroxyl or amino;

or two or more of $R_9$, $R_9'$, and $R_9''$ together form a ring (e.g., an alkylene group or an aryl or heteroaryl group).

In some embodiments, the sum of m and n is 3 or 4.

Optionally, one of $R_9$, $R_9'$ and $R_9''$ is -$M_3(R_{14})(R_{14}')$ $(R_{14}'')$, wherein $M_3$ is carbon, nitrogen, oxygen or sulfur; and each of $R_{14}$, $R_{14}'$, and $R_{14}''$ is independently hydrogen, alkyl, substituted alkyl, cycloalkyl, substituted alkyl, vinyl, aryl, substituted aryl, aralkyl, substituted aralkyl, acyl, alkoxyl, aralkoxyl, substituted aralkoxyl, furyl, pyranyl, thiophenyl, benzothiophenyl, halogen, hydroxyl, protected hydroxyl, or amino; wherein $R_{14}'$ and/or $R_{14}''$ can be present or absent and/or further wherein when one of $R_{14}$, $R_{14}'$, and $R_{14}''$ is hydroxyl or amino, the other two of $R_{14}$, $R_{14}'$ and $R_{14}''$ is not halogen or amino.

III. Methods of Preparing Prostanoids and Compounds of Formulae (II), (III), (IV), (V), (V-A), (VI), (VI-A), (VII), (VIII), (IX), (X), (XI), (XIV), (XV), and (XVI)

The presently disclosed processes can include an intramolecular ring closing metathesis reaction of a compound including two cyclopentane rings attached to one another via an alkylene group that comprises an alkene. This alkene is one of the alkenes involved in the intramolecular metathesis reaction. Thus, one of the alkene groups involved in the present intramolecular ring closing metathesis reactions is a group wherein both of the carbon atoms of the alkene group are substituted with at least one group other than hydrogen. The presently disclosed processes can also include an intermolecular metathesis reaction involving a chiral allylcyclopentenone and/or provide a prostanoid precursor or precursors that are generally crystalline and can be purified by conventional crystallization. Purification of prostaglandin intermediates, which are typically oils, has been accomplished historically via laborious chromatographic purifications.

Scheme 1A above shows an embodiment of the synthesis of a prostanoid intermediate of Formula (VIII) starting from a chiral allylcyclopentenone (compound I of Scheme 1A) that can comprise six synthesis steps: (1) an intermolecular metathesis reaction (i.e., of compound I of Scheme 1A to form compound III or of compound II of Scheme 1A to form compound IV), (2) an enantioselective 1,4-addition reaction (i.e., of compound I of Scheme 1A to form compound II or of compound III of Scheme 1A to form compound IV), (3) an asymmetric carbonyl reduction (i.e., of compound IV of Scheme 1A to form compound V), (4) an esterification (i.e., of compound V of Scheme 1A to form compound VI), (5) an intramolecular metathesis reaction (i.e., of compound VI of Scheme 1A to form compound VII), and (6) removal (e.g., a hydrolysis) of a protecting group (i.e., of compound VII of Scheme 1A to form compound VIII). In some embodiments, compounds VII and VIII (e.g., embodiments of compounds VII and VIII that do not include a carbon-carbon double bond in the lactone ring) can be provided by an additional reduction reaction (i.e., of the carbon-carbon double bond formed during the intramolecular metathesis reaction). The synthesis of prostaglandins from intermediate (VIII) entails the opening of the lactone and formation of a carboxylic acid or an ester or amide or other carboxylic acid derivative, which is typically accomplished in one step. Alternatively, the lactone of compound VII of Scheme 1A can be opened and the ring-opened product can be deprotected later (e.g., after oxidation of the new hydroxyl group of the ring-opened product to provide a cyclopentanone-containing prostanoid analog). In some embodiments, the process includes the providing the compound IV via a stereoselective 1,4 double addition of a suitable reagent to compound III.

III.A. Methods of Preparing Compounds of Formula (IA)

Chiral allylcyclopentonones of the Formula (I) have been prepared previously by different methods and used in the synthesis of prostaglandins. A number of examples are documented in the scientific and patent literature. See, Trampota, Miroslav and Zak, Bohumil PCT Int. Appl., 9628419, 19 Sep. 1996; Donde, Yariv and Nguyen, Jeremiah H. PCT Int. Appl., 2006063179, 15 Jun. 2006; Rodriguez, Ana et al, Archiv der Pharmazie (Weinheim, Germany), 331(9), 279-282; 1998 Kalish, Vincent J. et al Synthetic Communications, 20(11), 1641-5; 1990; Okamoto, Sentaro et al Journal of Organic Chemistry, 53(23), 5590-2; 1988; Rodriguez, Ana R. and Spur, Bernd W. Tetrahedron Letters, 43(50), 9249-9253; 2002; Oh, Changyoung et al PCT Int. Appl., 2010104344, 16 Sep. 2010; Ham, Won-Hun et al PCT Int. Appl., 2002090324, 14 Nov. 2002; Obadalova, Iva et al Chirality, 17(Suppl.), S109-S113; 2005; Tani, Kousuke et at Bioorganic & Medicinal Chemistry, 10(4), 1093-1106; 2002; Henschke, Julian P. et at U.S. Pat. Appl. Publ., 20090259058, 15 Oct. 2009; Burk, Robert M. et at PCT Int. Appl., 2003040126, 15 May 2003; Henschke, Julian P. et at PCT Int. Appl., 2012048447, 19 Apr. 2012; Donde, Yariv U.S. Pat. Appl. Publ., 0050228185, 13 Oct. 2005; Kim, Yong Hyun and Lee, Yiu Suk PCT Int. Appl., 2004026224, 1 Apr. 2004.

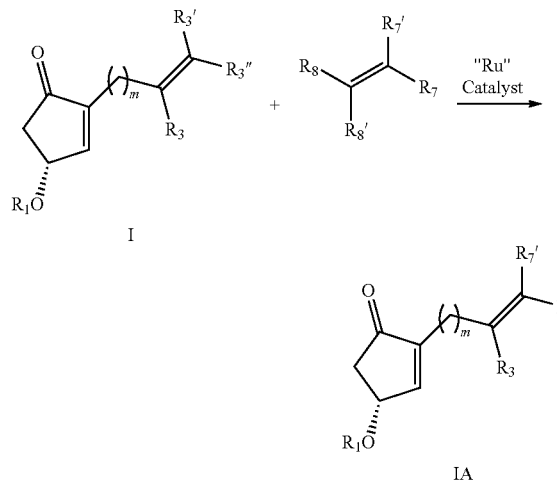

Scheme 2. Synthesis of Compounds of Formula (IA).

In some embodiments, the presently disclosed subject matter provides a method for converting chiral allylcyclopentenones of Formula (I) to other chiral allylcyclopentenones (e.g., compounds of Formula (IA)) via a cross-metathesis reaction with another suitable alkene catalyzed by a transition metal catalyst, such as, but not limited to a ruthenium-based catalyst. See Scheme 2, above. In the alkene shown in Scheme 2, $R_3$ can be any group (e.g., H, alkyl, aralkyl, or aryl, or substituted versions thereof) with the proviso that $R_3$ is not electron-donating and/or does not comprise a heteroatom attached directly to the carbon of the alkene. In some embodiments, the $R_3'$ and $R_3''$ groups can be as defined above for the compounds of Formula (II). In some embodiments, one of $R_3'$ and $R_3''$ can be alkyl, but not both are alkyl. In some embodiments, one of $R_3'$ and $R_3''$ is alkyl and the other is H. In some embodiments, $R_8$ and $R_8'$ can be the same groups as defined for $R_3'$ and $R_3''$. In some embodiments, one of $R_8$ and $R_8'$ is alkyl and one is H. In some embodiments, both $R_3$ and $R_3'$ are H. $R_7$ and $R_7'$ can independently be any group (e.g., alkyl, acyl, halogen, etc.). To drive the reaction to completion, ethylene or alkylene formed as a side product during the reaction can be removed from the reaction system.

In some embodiments, the catalyst comprises a transition metal such as, but not limited to, Ni, W, Ru, Rh, or Mo. In some embodiments, the transition metal is Ru. In some embodiments, the catalyst is a transition metal carbene complex, such as, but not limited to a transition metal benzylidene (e.g., a ruthenium benzylidene). In some embodiments, the catalyst is a Schrock, Grubb's, or Hoveyda-Grubb's catalyst. In some embodiments, the catalyst is benzylidene-bis(tricyclohexylphosphine) dichlororuthenium.

In some embodiments, reacting the compound of Formula (I) with a catalyst to perform a metathesis reaction is performed in a non-polar, aprotic solvent, such as, but not limited to, dichloromethane, toluene, heptane, or MTBE.

The compounds of Formula (IA) can be used in place of the compounds of Formula (I) in the synthesis of additional compounds of the presently disclosed subject matter, e.g., in the synthesis of compounds of Formulae (II), (III), etc., via routes analogous to that shown in Scheme 1A.

III.B. Methods of Preparing Compounds of Formula (III)

As described hereinabove, chiral allylcyclopentenones of Formula (I) can be produced by a variety methods documented in the scientific literature. See e.g., Mitsuda et al., *Applied Microbiology and Biotechnology*, 31(4), 334-337 (1989); Hazato et al., *Chem. Pharm. Bull.*, 33(5), 1815-1825 (1985); and U.S. Pat. No. 7,109,371.

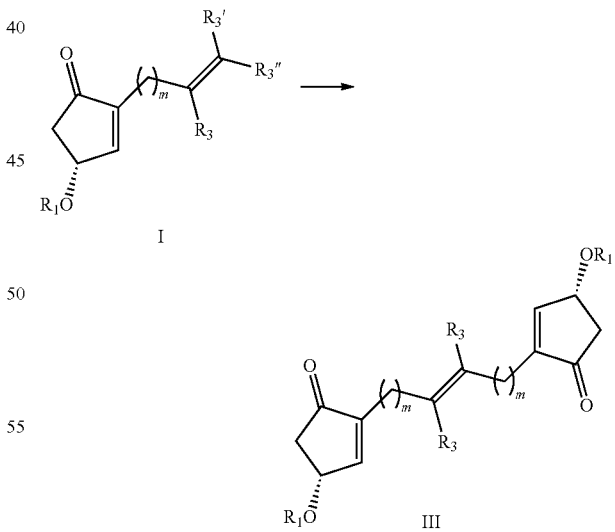

Scheme 3. Synthesis of Compounds of Formula (III).

In some embodiments, the presently disclosed subject matter provides a method for converting chiral allylcyclopentenones of Formula (I) to compounds of Formula (III) via a metathesis reaction catalyzed by a transition metal catalyst, such as, but not limited to a ruthenium-based catalyst. See Scheme 3, above. The metathesis reaction can be between two compounds of Formula (I), which can be the same or different. In some embodiments, the two compounds of Formula (I) are the same. To drive the reaction to completion, ethylene or alkylene formed as a side product during the reaction can be removed from the reaction system.

In some embodiments, the catalyst comprises a transition metal such as, but not limited to, Ni, W, Ru, Rh, or Mo. In some embodiments, the transition metal is Ru. In some embodiments, the catalyst is a transition metal carbene complex, such as, but not limited to a transition metal benzylidene (e.g., a ruthenium benzylidene). In some embodiments, the catalyst is a Schrock, Grubb's, or Hoveyda-Grubb's catalyst. In some embodiments, the catalyst is benzylidene-bis(tricyclohexylphosphine) dichlororuthenium.

In some embodiments, reacting the compound of Formula (I) with a catalyst to perform a metathesis reaction is performed in a non-polar, aprotic solvent, such as, but not limited to, dichloromethane, toluene, heptane, or MTBE.

III.C. Methods of Preparing Compounds of Formula (IV)

In some embodiments, the presently disclosed subject matter provides a method for producing compounds of Formula (IV) by sequentially performing: (a) a stereoselective 1,4-addition reaction of a suitable reagent to a chiral allylcyclopentenone, and (b) a metathesis reaction. See Scheme 1A, above. The metathesis reaction can be performed prior to the 1,4-addition reaction, e.g., the compound of Formula (IV) can be prepared by metal-catalyzed cross-metathesis reaction of a compound of Formula (I) (e.g., to a second compound of Formula (I), which can be the same or different) to provide a compound of Formula (III), followed by a 1,4 double addition reaction of a suitable reagent or reagents to provide the compound of Formula (IV). Alternative, the 1,4-addition can be performed prior to the metathesis reaction, e.g., the compound of Formula (IV) can be prepared by 1,4-addition of a suitable reagent to a compound of Formula (I) to provide a compound of Formula (II), followed by a metal-catalyzed cross-metathesis reaction of a compound of Formula (II) (e.g., to a second compound of Formula (II), which can be the same or different) to provide the compound of Formula (IV). The catalyst for the metathesis reaction can be a transition metal catalyst as described for the methods of preparing the compounds of Formula (III).

In some embodiments, the presently disclosed subject matter comprises a stereoselective 1,4-double addition of a suitable reagent or reagents to a compound of the Formula (III). See Scheme 4, below. In some embodiments, the 1,4-addition reaction is a 1,4-double addition of two of the same reagents (i.e., addition of two of the same reagents, one at each of the cyclopentenone carbon-carbon double bonds).

Scheme 4. Synthesis of Compounds of Formula (IV) via 1,4-Double Addition.

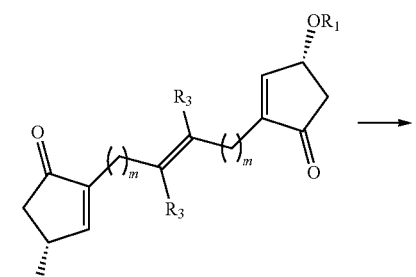

III

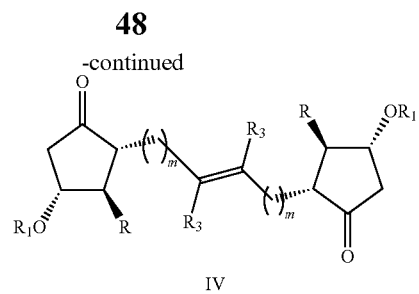

IV

Stereoselective conjugate addition of suitable reagents to α,β-unsaturated ketones has been previously reported. See, e.g., Taylor, *Synthesis*, 364-392, (1985). Suitable reagents for the stereoselective 1,4-addition reaction include, but are not limited to, certain nucleophiles (e.g. nitroalkyl anions, alkyl sulphone anions, acyl anion equivalents, and organocuprates produced from alkyl halides, vinyl halides, or vinyl ethers, and alkynes).

Organocuprate precursor compounds of Formula (Z) below and methods for their preparation are well known to those skilled in the art. Formula (Z) has the structure:

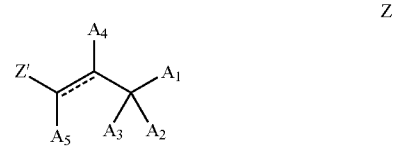

Z $A_1$, $A_2$, $A_3$, $A_4$, and $A_5$ of the compound of Formula (Z) can be as described above for the compounds of Formula (IV), while Z' can be, for example, halo (i.e., I, Br, Cl, or F) or alkoxy.

Techniques for forming suitable organocuprate reagents from compounds of Formula (Z) are also well known to the person skilled in the art. For example, compounds of Formula (Z) can be reacted with an alkyllithium reagent (e.g. n-BuLi) and copper cyanide in a suitable solvent such as THF or MTBE at low temperatures (e.g., at −78° C. to 0° C.). The organocuprate reagent formed in the reaction can be reacted with a compound of Formula (III), also at low temperatures, to undergo 1,4-addition reaction and produce compound of Formula (IV).

III.D. Methods of Preparing Compounds of Formula (V)

In some embodiments, the presently disclosed subject matter provides a method for converting a compound of Formula (IV) to a compound of Formula (V) via reduction (e.g., enantioselective reduction) of the carbonyl groups of the cyclopentane rings. See Scheme 5, below.

Scheme 5. Synthesis of Compounds of Formula (V).

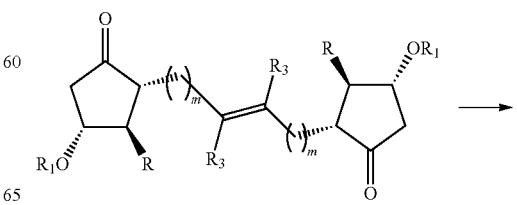

IV

-continued

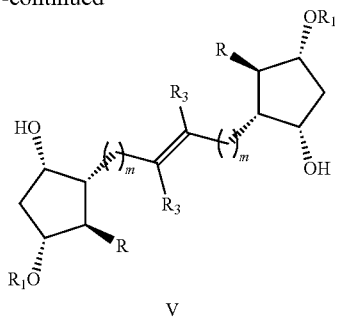

V

Typical reducing reagents are a boron or aluminum hydride donor, such as, but not limited to sodium borohydride (NaBH$_4$), lithium aluminum hydride (LAlH$_4$), and diisobutylaluminum hydride (DIBALH). Reduction of a compound of Formula (IV) can be non-stereoselective, leading to a mixture of isomeric alcohols, or stereoseletive, leading to the formation of a single isomer of an alcohol, depending upon the reducing agent and/or conditions used. In some embodiments, the reducing agent can be a stereoselective reducing agent (e.g. SELECTRIDE™) used at low temperatures (e.g. −78° C.). In some embodiments, the reduction is performed using a reducing agent and a chiral ligand. In some embodiments, the reducing reagent is borane with CBS oxazaborolidine catalyst (known as the Corey-Bakshi-Shibata (CBS) reduction).

Any suitable solvent can be used for these reactions. In some embodiments, suitable solvents for these reactions include aprotic solvents, such as, but not limited to, ethers (e.g., tetrahydrofuran (THF) or methyl tert-butyl ether (MTBE)) or halogenated alkanes (e.g., dichloromethane (DCM)).

III.E. Methods of Preparing Compounds of Formula (VI)

In some embodiments, the presently disclosed subject matter provides a method for esterifying a compound of Formula (V) (i.e., at the two cyclopentane hydroxyl groups) with a carboxylic acid (e.g., an alkenoic acid) or an acid chloride or anhydride. See Scheme 6, below.

In some embodiments, a suitable carbodiimide (e.g., N,N'-dicyclohexylcarbodiimide (DCC)) and a non-nucleophilic base are used with an alkenoic acid for the esterification.

In some embodiments, the alkenoic acid can be selected from the group comprising, but not limited to, 2-propenoic acid (i.e., acrylic acid), 2-methyl-2-propenoic acid (i.e., methacrylic acid), 2-butenoic acid (i.e., crotonic acid), 3-butenoic acid, 4-pentenoic acid, 5-hexenoic acid, 5-heptenoic acid, 6-methyl-5-heptenoic acid, 6-heptenoic acid, 7-octenoic acid, 8-nonenoic acid, 9-decenoic acid, 10-undecenoic acid, 11-dodecenoic acid, and 12-tridecenoic acid or derivatives thereof. The alkenoic acid can also be a derivative of an unsubstituted alkenoic acid, and can, for example, comprise one or more alkyl group substituents (e.g., attached to one of the carbons of the carbon-carbon double bond).

III.F. Methods of Preparing Compounds of Formula (VII)

In some embodiments, the presently disclosed subject matter provides a process for preparing prostaglandin key intermediates using an approach based upon ring-closing metathesis (RCM) of a precursor compound, wherein the precursor compound comprises at least one cyclopentane ring, wherein the at least one cyclopentane ring is substituted by at least four substituents: —OR$_1$, R, and two additional substitutents, wherein R$_1$ and R are as defined for the compounds of Formula (VII) and Formula (VIII) above, and the two additional substituents each comprise an alkene moiety, further wherein at least one of the two additional substituent groups comprises a non-terminal alkene. In some embodiments, a compound of Formula (VI) to used to form prostaglanin-1,9-lactones (e.g., of Formula (VII)) via a RCM reaction catalyzed by a transition metal catalyst, such as, but not limited to a ruthenium-based catalyst. See Scheme 7, below. Thus, in some embodiments, the precursor compound is a compound of Formula (VI). In some embodiments, the precursor compound is a compound of Formula (VI-A), described hereinabove.

Scheme 6. Synthesis of Compounds of Formula (VI).

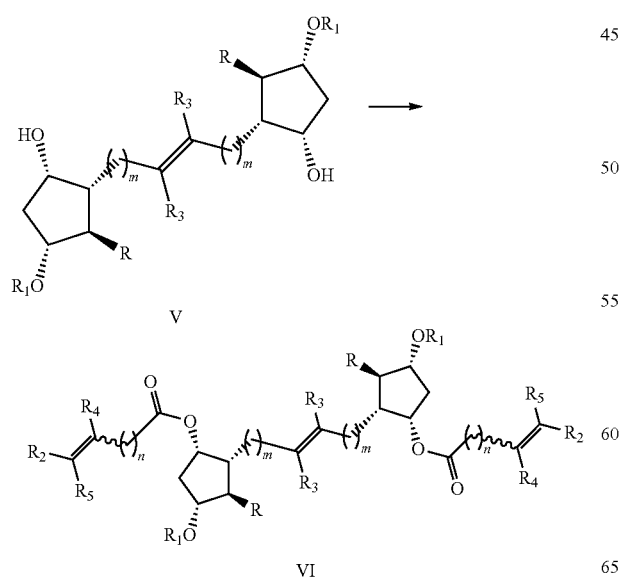

Scheme 7. Synthesis of Compounds of Formula (VII).

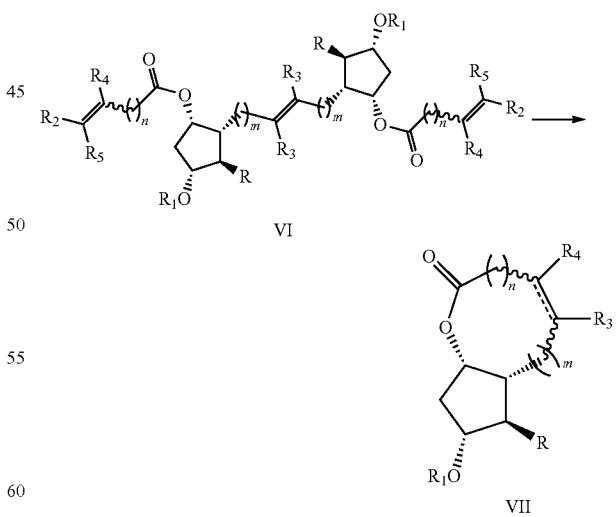

In some embodiments, the catalyst comprises a transition metal such as, but not limited to, Ni, W, Ru, Rh, or Mo. In some embodiments, the transition metal is Ru. In some embodiments, the catalyst is a transition metal carbene complex, such as, but not limited to a transition metal benzylidene (e.g., a ruthenium benzylidene). In some embodiments, the catalyst is a Schrock, Grubb's, or Hoveyda-Grubb's catalyst. In some embodiments, the catalyst is benzylidene-bis(tricyclohexylphosphine) dichlororuthenium.

In some embodiments, reacting the precursor compound (e.g., of Formula (VI)) with a catalyst to perform a ring closing metathesis reaction is performed in a non-polar, aprotic solvent, such as, but not limited to, dichloromethane, toluene, heptane, or MTBE.

In some embodiments, the lactone is a nine-membered or ten-membered ring and n+m is 3 or 4. In some embodiments, the lactone is a ten-membered ring and n+m is 4. In some embodiments, n is 2 or 3 and m is 1. In some embodiments, n is 3 and m is 1. In some embodiments, n is 1 and m is 4. In some embodiments, $R_2$ in the compound of Formula (VI) or (VI-A) is alkyl.

In some embodiments (e.g., to provide compounds of Formula (VII) wherein the lactone ring carbon-carbon double bond is absent), the ring-closing metathesis reaction can be followed by a reduction reaction (e.g., a palladium catalyzed hydrogenation reaction) to reduce the carbon-carbon double bond formed during the metathesis reaction to a carbon-carbon single bond.

III.G. Methods of Preparing Compounds of Formula (VIII)

In some embodiments, the presently disclosed subject matter provides a process for preparing prostaglandin intermediates of the Formula (VIII) via removal of a hydroxyl protecting group (i.e., $R_1$) from a compound of Formula (VII). See Scheme 8, below. For example, the process can comprise hydrolysis (e.g., acid- or base-catalyzed hydrolysis) of the protected hydroxyl group.

Scheme 8. Synthesis of Compounds of Formula (VIII).

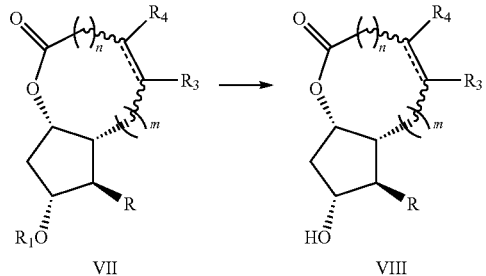

In some embodiments (e.g., to provide compounds of Formula (VIII) wherein the lactone ring carbon-carbon double bond is absent), the synthesis can also include a reduction reaction (e.g., a palladium catalyzed hydrogenation reaction) to reduce the lactone ring carbon-carbon double bond (e.g., if still remaining in the compound of Formula (VII)) to a carbon-carbon single bond.

In some embodiments (e.g., when $R_1$ is H in the compounds of Formula (VI) or (VI-A)), the compound of Formula (VIII) can be prepared by a RCM reaction as described for the compounds of Formula (VII).

The presently disclosed synthetic route to provide a compound of Formula (VIII), which is an intermediate in the synthesis of prostanoids, is both highly versatile and scalable and uses readily available or easily prepared starting materials. Each of the individual steps in the synthesis can be performed in high yield. More importantly, the process disclosed herein generally provides crystalline intermediates, an important factor in the synthesis of prostaglandins and prostaglandin analogues, as their intermediates and actual products are generally oils. As such they require extensive chromatographic purifications that are generally laborious. The process disclosed herein allows purification of intermediates via conventional crystallization methods and, as a result offers a significant advantage over the commercial processes currently in practice.

III.H. Methods of Preparing Compounds of Formula (IX)

In some embodiments, the presently disclosed subject matter provides a process for preparing prostaglandin intermediates of the Formula (IX) via cleavage of the double bond in compound of Formula (V). See Scheme 9, below. For example, the process can comprise ozonolysis of the double bond or other chemical double bond cleavage. Compounds of the Formula (IX) are well documented in the literature and have been used in the past to produce prostanoids via traditional routes as disclosed in Classics in Total Synthesis, Weinheim, Chapter 5, The Logic of Chemical Synthesis, Wiley, 1995, Chemical Reviews 93, 1993, 1533-1564, Prostaglandin Synthesis, Academic Press, 1977, and Chinese Journal of Medicinal Chemistry, 36, 1998, 213-217, among many others.

Scheme 9. Synthesis of Compounds of Formula (IX).

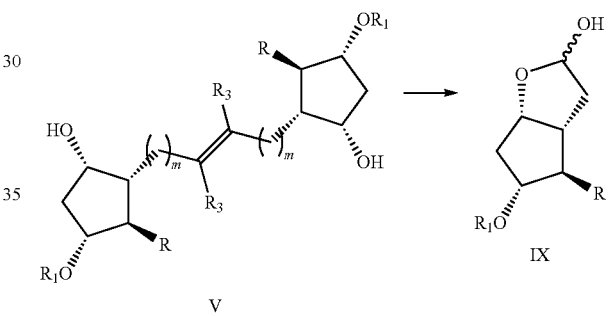

III.I. Methods of Preparing Compounds of Formula (X)

In some embodiments, the presently disclosed subject matter provides a process for preparing prostaglandin intermediates of the Formula (X) via a metal-catalyzed cross-metathesis reaction between compounds of the Formula (I) and an alkenoic acid of suitable length, such as 5-hexenoic acid or 5-heptenoic acid, as shown in Scheme 10, below. Compounds of the Formula (X) are well documented in the literature and have been used in the past to produce prostanoids. See, Trampota, Miroslav and Zak, Bohumil PCT Int. Appl., 9628419, 19 Sep. 1996; Donde, Yariv and Nguyen, Jeremiah H. PCT Int. Appl., 2006063179, 15 Jun. 2006; Rodriguez, Ana et al; Archiv der Pharmazie (Weinheim, Germany), 331(9), 279-282; 1998 Kalish, Vincent J. et al Synthetic Communications, 20(11), 1641-5; 1990; Okamoto, Sentaro et at Journal of Organic Chemistry, 53(23), 5590-2; 1988; Rodriguez, Ana R. and Spur, Bernd W. Tetrahedron Letters, 43(50), 9249-9253; 2002; Oh, Changyoung et al PCT Int. Appl., 2010104344, 16 Sep. 2010; Ham, Won-Hun et at PCT Int. Appl., 2002090324, 14 Nov. 2002; Obadalova, Iva et at Chirality, 17(Suppl.), S109-S113; 2005; Tani, Kousuke et at Bioorganic & Medicinal Chemistry, 10(4), 1093-1106; 2002; Henschke, Julian P. et at U.S. Pat. Appl. Publ., 20090259058, 15 Oct. 2009; Burk, Robert M. et al PCT Int. Appl., 2003040126, 15 May 2003; Henschke, Julian P. et at PCT Int. Appl., 2012048447, 19 Apr. 2012;

Donde, Yariv U.S. Pat. Appl. Publ., 0050228185, 13 Oct. 2005; Kim, Yong Hyun and Lee, Yiu Suk PCT Int. Appl., 2004026224, 1 Apr. 2004.

Scheme 10. Synthesis of Compounds of Formula (X).

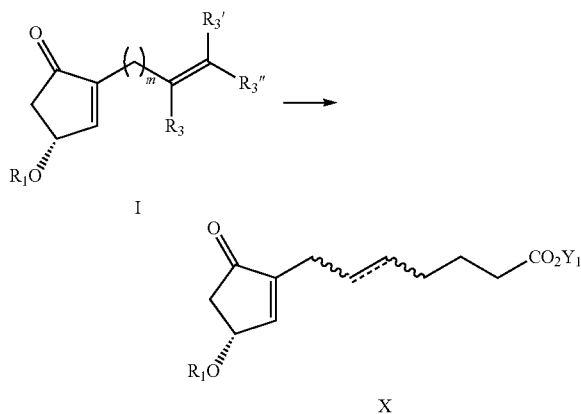

$Y_1$ in Formula (X) can be, for example, H, alkyl, substituted alkyl, aralkyl, substituted aralkyl, aryl, or substituted aryl, such that the compound of Formula (X) is a carboxylic acid or an ester.

III.J. Methods of Preparing Compounds of Formula (XI)

In some embodiments, the presently disclosed subject matter provides a process for preparing prostaglandin intermediates of the Formula (XI) via two potential routes: (a) from compounds of the Formula (VII-5A) or (VIII-5A) via a Horner-Emmons reaction with a suitable phosphonate, and (b) via a metal-catalyzed cross-metathesis reaction between compounds of the Formula (VII-6) or (VIII-6) and a suitable enone, as shown in Scheme 11 below.

Scheme 11. Synthesis of Compounds of Formula (XI).

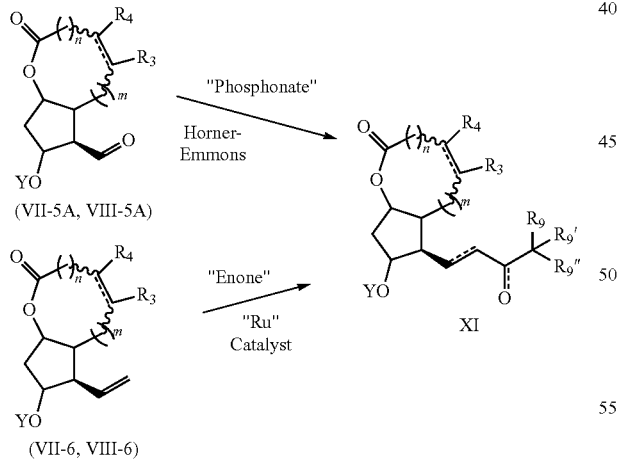

In some embodiments, the compounds of Formula (VII-5A) and Formula (VIII-5A) can be prepared from a nitro group-containing compound (e.g., a compound of Formula (VII) or Formula (VIII) wherein R is —$CH_2NO_2$). In some embodiments, the nitro group-containing compound can be contacted with titanium trichloride and an acetate (e.g., ammonium or sodium acetate) to provide the aldehyde-containing compound of Formula (VII-5A) or Formula (VIII-5A).

In some embodiments, for the compounds of Formulae (VII-5A), (VIII-5A), (VII-6) and/or (VIII-6), n is 3 and m is 1. In some embodiments, $R_3$ and $R_4$ are each H.

III.K. Methods of Preparing Compounds of Formula (XIV)

In some embodiments, the presently disclosed subject matter provides a process for preparing prostaglandin intermediates of the Formula (XIV) via (a) hydrolysis of a lactone of the Formula (VII-6) or (VIII-6) followed by esterification or amide bond formation, or (b) via direct opening of the same lactones with a suitable alkoxide, thiol, or amine. See Scheme 12 below.

Scheme 12. Synthesis of Compounds of Formula (XIV).

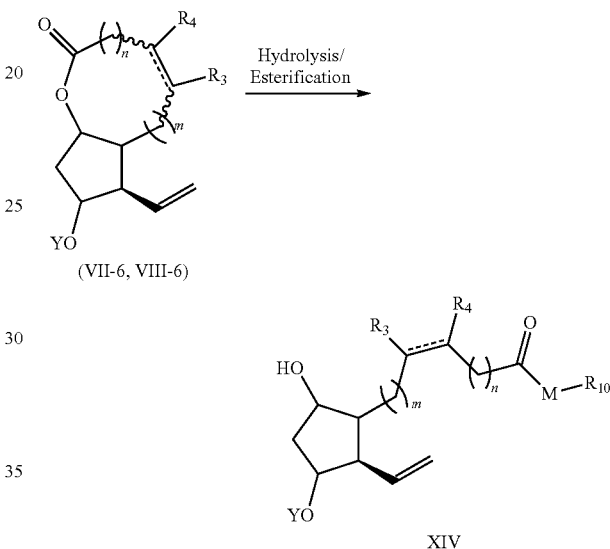

III.L. Methods of Preparing Compounds of Formula (XV)

In some embodiments, the presently disclosed subject matter provides a process for preparing prostaglandin intermediates of the Formula (XV) via (a) a hydrolysis of lactones of the Formula (VII-6) or (VIII-6) followed by esterification with a suitable chiral allylic alcohol, or (b) via direct opening of the same lactone with the alkoxide of a suitable chiral allylic alcohol. See Scheme 13 below.

Scheme 13. Synthesis of Compounds of Formula (XV).

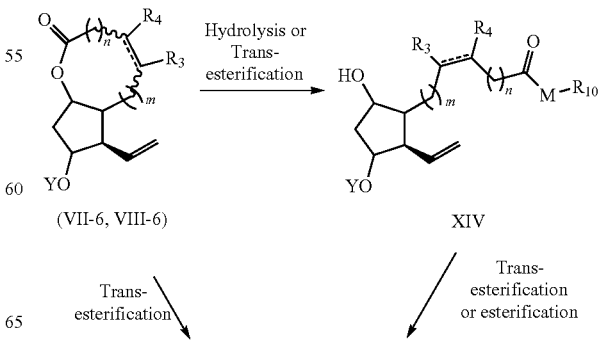

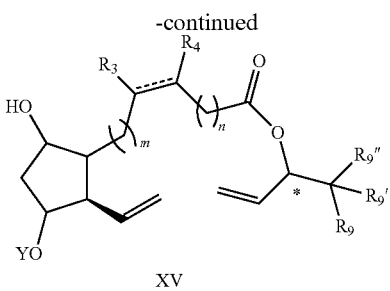

XV

III.M. Methods of Preparing Compounds of Formula (XVI)

In some embodiments, the presently disclosed subject matter provides a process for preparing prostaglandin intermediates of the Formula (XVI) via a metal-catalyzed (e.g., a ruthenium-catalyzed) intramolecular metathesis reaction. See Scheme 14 below.

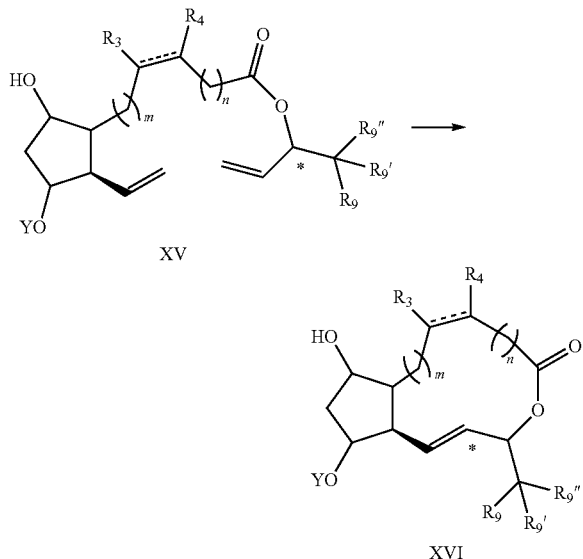

Scheme 14. Synthesis of Compounds of Formula (XVI).

III.N. Methods of Preparing Prostaglandins

In some embodiments of the presently disclosed subject matter, prostaglandins can be prepared by opening the lactone ring of the compounds of Formulae (VII) or (VIII) with a suitable nucleophile to provide a ring-opened product. In some embodiments, the nucleophile is selected from the group comprising water, alcohol (e.g., an aliphatic or aromatic alcohol), a thiol (e.g., alkylthiols and arylthiols), and amine (or another nitrogen nucleophile, such as, but not limited to a sulfonamide or imide). The nucleophiles can be provided in a deprotonated form (e.g., as hydroxide, an alkoxide or a thiolate) or as salts, such as salts of alkali metal cations (e.g., sodium, lithium, potassium, or cesium salts of hydroxide, an alkoxide or a thiolate) or deprotonated in situ during a reaction. In some embodiments, the nucleophile is an alkylamine or arylamine, such as, but not limited to, ethylamine. In some embodiments, the nucleophile is an alcohol, an alkoxide, an alkoxide salt, or a mixture thereof, such as, but not limited to 2-propanol and/or sodium isopropoxide.

When the nucleophile is an amine, ring opening can provide a compound comprising an amide. When the nucleophile is an alcohol, alkoxide or aryloxide, ring opening can provide a compound comprising an ester. When the nucleophile is water or hydroxide, ring opening can provide a carboxylic acid, which can be further reacted, if desired, to provide an ester or other carboxylic acid derivative. Thus, in some embodiments, the lactone ring is opened via hydrolysis (e.g., acid-catalyzed hydrolysis), and the resulting carboxylic acid is esterified.

In some embodiments, reacting the lactone with a nucleophile is performed in an aprotic solvent, such as, but not limited to, tetrahydrofuran. In some embodiments, ring opening is performed in a protic solvent, such as an alcohol.

If desired, the ring-opened product (e.g., of the ring opening of a compound of Formula (VII)) can be further reacted to oxidize the hydroxyl group formed from opening the lactone (e.g., via Swern oxidation or using a Dess-Martin periodinane, pyridinium chlorochromate, Jones reagent or Collins reagent). In some embodiments, the ring-opened product can be further reacted to remove one or more hydroxyl protecting groups. In some embodiments, the ring-opened product can be further reacted with a reagent to remove or transform an alkene group into another group (e.g, to transform an alkene group to a carbon-carbon single bond via catalytic hydrogenation). In some embodiments, a carboxylic acid derivative formed during or after the opening of the lactone can be reduced with a suitable reducing agent (e.g. to provide a hydroxyl or aldehyde group).

Hydroxyl protecting groups or carbonyl protecting groups (e.g., cyclic ketals, such as ethylenedioxy), if used, can be removed either prior to or after lactone ring opening. In some embodiments, one or more protecting groups can be removed prior to ring opening (i.e., prior to contacting the lactone with a nucleophile). In some embodiments, the protecting group(s) can be removed prior to the ring-closing metathesis reaction. In some embodiments, for example when silyl ethers, such as but not limited to, TBDMS groups, are used as hydroxyl protecting groups, they can be removed by reacting the compound of Formula (VII), Formula (VIII) or the ring-opened compound with reagents, such as, but not limited to, $NH_4HF_2$, trifluoroacetic acid, tetrabutylammonium fluoride and tetrabutylammonium chloride, or any other suitable reagents known to remove the hydroxyl protecting group.

In some embodiments, the presently disclosed methods of providing the compounds of Formulae (IV), (V), (VI), (VII), (VIII), or (IX) or of providing any prostaglandin or prostaglandin analog, are free of a 1,4-addition to a compound of Formula (I). In some embodiments, the methods are free of a 1,4-addition to a compound of Formula (I) where $R_3$, $R_3'$, and $R_3''$ are all hydrogens or where both $R_3'$ and $R_3''$ are hydrogens.

TABLE 2

Reagents for 1,4-Addition Reactions.

| | |
|---|---|
| 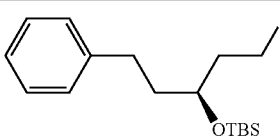 | 1I |
| 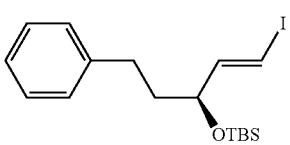 [SMILES: CC(C)(C)[Si](C)(C)O[C@H](/C=C/I)CCc1ccccc1] | 2I |

TABLE 2-continued

Reagents for 1,4-Addition Reactions.

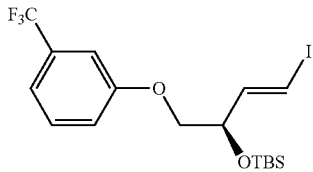 [SMILES: CC(C)(C)[Si](C)(C)O[C@H](/C=C/I)COc1cccc(C(F)(F)F)c1]
3I

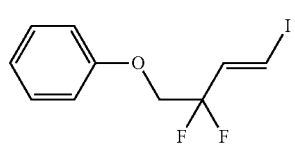
4I

CH$_3$NO$_2$ 5I

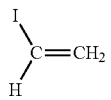
6I

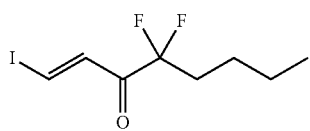
7I

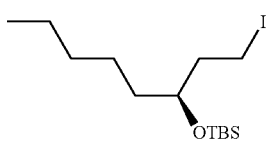 [SMILES: CCCCC[C@@H](CCI)O[Si](C)(C)C(C)(C)C]
8I

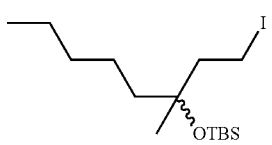 [SMILES: CCCCCC(C)(CCI)O[Si](C)(C)C(C)(C)C]
9I

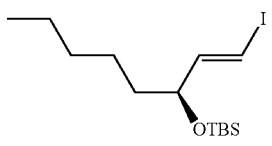
10I

TABLE 2-continued

Reagents for 1,4-Addition Reactions.

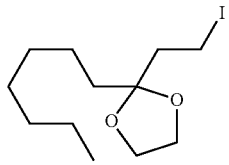
11I

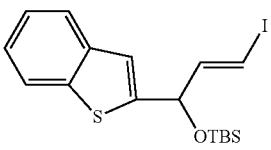 [SMILES: CC(C)(C)[Si](C)(C)OC(/C=C/I)c1cc2ccccc2s1]
12I

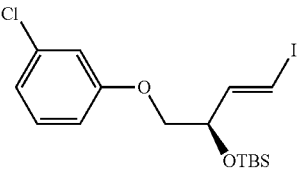 [SMILES: CC(C)(C)[Si](C)(C)O[C@H](/C=C/I)COc1cccc(Cl)c1]
13I

For example, in some embodiments where R is group (1) of Table 1 above, the above described reaction sequence (i.e., of Scheme 1A) leads to the production of the lactone VIII-1 and ultimately latanoprost as outlined in Scheme 15. Compound (IV-1) can be produced from compound (I') via two routes: (a) via 1,4-addition of the copperlithium reagent (1I) of Table 2 to compound (I') followed by a cross metathesis reaction using metal catalysis, such as using tricyclohexylphosphine[1,3-bis(2,4,6-trimethylphenyl)imidazol-2-ylidene][3-phenyl-1H-inden-1-ylidene]ruthenium (II) dichloride, or (b) first via a metal-catalyzed cross metathesis reaction of compound (I') using the same catalyst to produce compound (III') followed by a double 1,4-addition of the copperlithium reagent (1I). The carbonyl groups in compound (IV-1) may then be reduced enantioselectively to the diol (V-1) using an enantioselective reducing reagent, such as (R)-(+)-2-methyl-CBS-oxazaborolidine [(R)—CBS] and borane dimethylsulfide. Both hydroxyl groups of the resulting diol are then esterified with 5-heptenoic acid to produce compound (VI-1). This intermediate is subjected to an intra-molecular metathesis reaction using metal catalysis, such as tricyclohexylphosphine[1,3-bis(2,4,6-trimethylphenyl)imidazol-2-ylidene][3-phenyl-1H-inden-1-ylidene]ruthenium(II) dichloride, to produce the protected lactone (VII-1). Deprotection of this lactone with a suitable reagent, such as ammonium hydrogen difluoride, produces the lactone (VIII-1), the penultimate intermediate in the synthesis of latanoprost. Chemical process details for the synthesis of the lactone (VIII-1) are provided in Examples 1-6.

Opening of the lactone, which can be done under acidic or basic conditions, followed by esterification, or direct opening of the lactone with isopropoxide leads to the preparation of latanoprost as described in U.S. Pat. No. 8,476,471.

Scheme 15. Synthesis of Latanoprost.
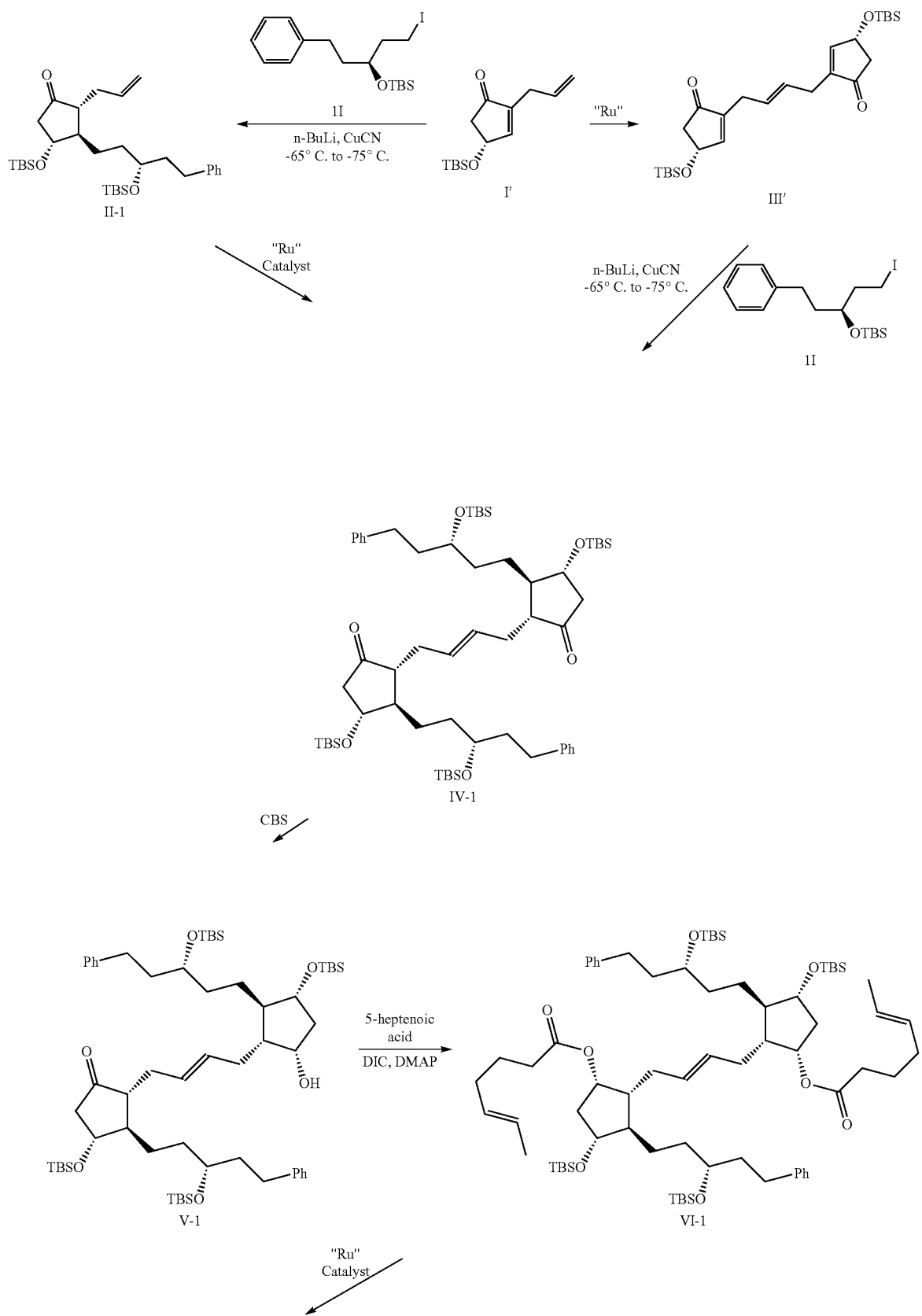

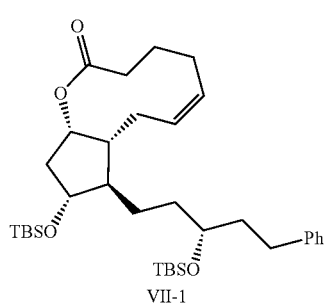
VII-1

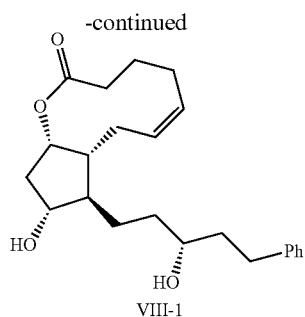
VIII-1

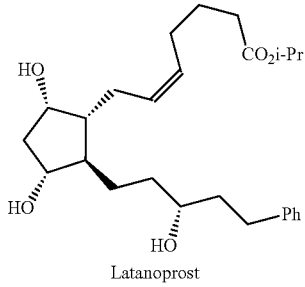
Latanoprost

In some embodiments, e.g., where R is group (2) from Table 1, the above described reaction sequence leads to the production of bimatoprost as outlined in Scheme 16. Compound (IV-2) can be produced from compound (I') via two routes; (a) via 1,4-addition of the copperlithium reagent (2I) from Table 2 to compound (I') followed by a cross metathesis reaction using metal catalysis, such as with tricyclohexyphosphine[1,3-bis(2,4,6-trimethylphenyl)imidazol-2-ylidene][3-phenyl-1H-inden-1-ylidene]ruthenium(II) dichloride, or (b) first via a metal-catalyzed cross metathesis reaction of compound (I') using the same catalyst to produce compound (III') followed by a double 1,4-addition of the copperlithium reagent (2I). The carbonyl groups in compound (IV-2) may then be reduced enantioselectively to provide the diol (V-2) using an enantioselective reducing reagent, such as (R)-(+)-2-methyl-CBS-oxazaborolidine [(R)—CBS] and borane dimethylsulfide. Both hydroxyl groups of the resulting diol are then esterified with 5-heptenoic acid to produce compound (VI-2). This intermediate is subjected to an intra-molecular metathesis reaction using metal catalysis, such as with tricyclohexylphosphine[1,3-bis (2,4,6-trimethylphenyl)imidazol-2-ylidene][3-phenyl-1H-inden-1-ylidene]ruthenium(II) dichloride, to produce the protected lactone (VII-2). Deprotection of this lactone with a suitable reagent, such as ammonium hydrogen difluoride, produces the lactone (VIII-2), the penultimate intermediate in the synthesis of bimatoprost. Chemical process details for the synthesis of the lactone (VIII-2) are provided in Examples 7-13. Direct opening of the lactone with ethylamine leads to the preparation of bimatoprost as described in U.S. Pat. No. 8,476,471.

Scheme 16. Synthesis of Bimatoprost.

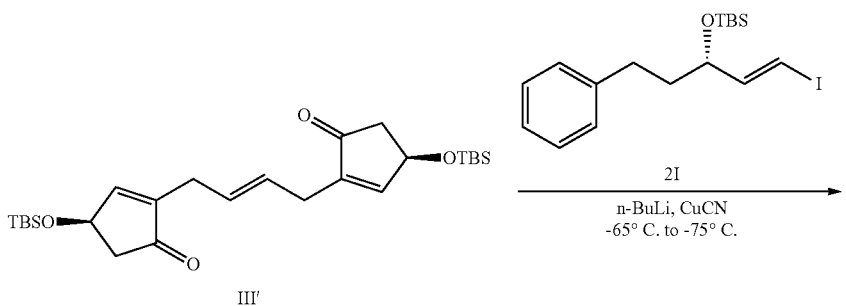

-continued
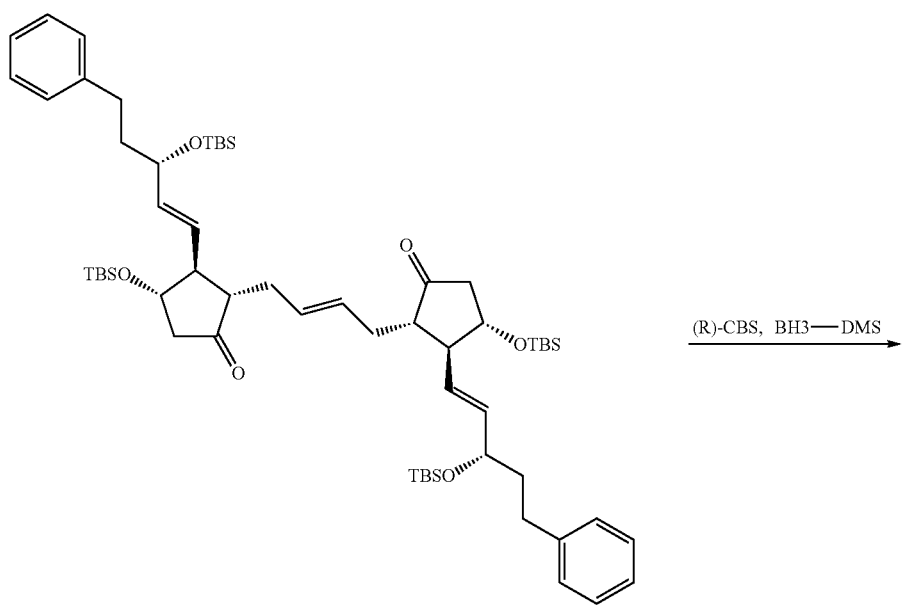
IV-2
(R)-CBS, BH3—DMS →
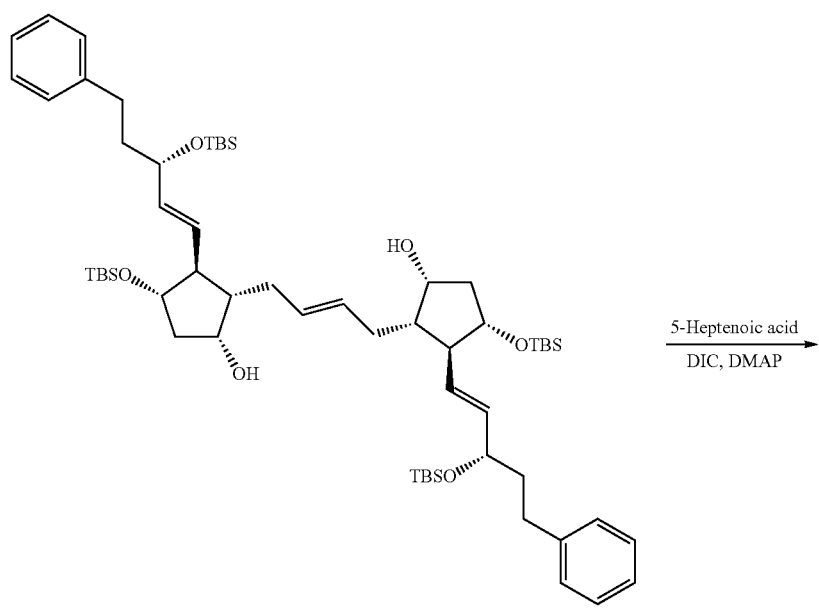
V-2
5-Heptenoic acid
DIC, DMAP →

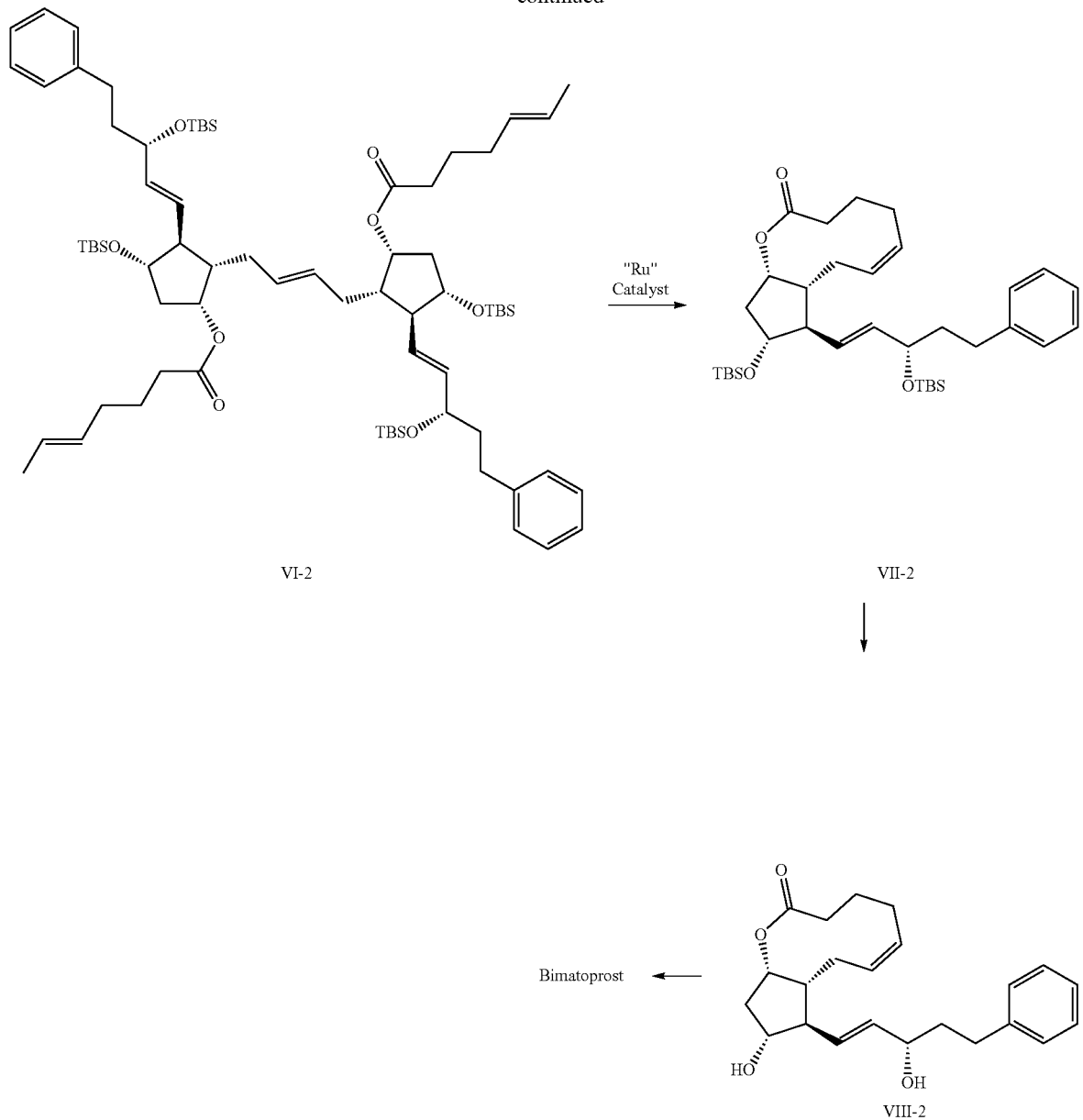

VI-2

VII-2

Bimatoprost ←

VIII-2

In yet some other embodiments, e.g., where R is group (3) of Table 1, the above described reaction sequence leads to the production of the lactone VIII-3 and ultimately travoprost as outlined in Scheme 17. Compound (IV-3) can be produced from compound (I') via two routes; (a) via 1,4-addition of the copperlithium reagent (3I) from Table 2 to compound (I') followed by a cross metathesis reaction using metal catalysis, such as with tricyclohexylphosphine[1,3-bis(2,4,6-trimethylphenyl)imidazol-2-ylidene][3-phenyl-1H-inden-1-ylidene]ruthenium(II) dichloride, or (b) first via a metal-catalyzed cross metathesis reaction of compound (I') using the same catalyst to produce compound (III') followed by a double 1,4-addition of the copperlithium reagent (3I). The carbonyl groups in compound (IV-3) may then be reduced enantioselectively to provide the diol (V-3) using an enantioselective reducing reagent, such as (R)-(+)-2-methyl-CBS-oxazaborolidine [(R)—CBS] and borane dimethylsulfide. Both hydroxyl groups of the resulting diol are then esterified with 5-heptenoic acid to produce compound (VI-3). This intermediate is subjected to an intra-molecular metathesis reaction using metal catalysis, such as with tricyclohexylphosphine[1,3-bis(2,4,6-trimethylphenyl)imidazol-2-ylidene][3-phenyl-1H-inden-1-ylidene]ruthenium (II) dichloride, to produce the protected lactone (VII-3). Deprotection of this lactone with a suitable reagent, such as ammonium hydrogen difluoride, produces the lactone (VIII-3), the penultimate intermediate in the synthesis of travoprost. Chemical process details are provided in Examples 14-15.

Opening of the lactone, which can be done under acidic or basic conditions, followed by esterification, or direct opening of the lactone with isopropoxide leads to the preparation of travoprost as described in U.S. Pat. No. 8,476,471.

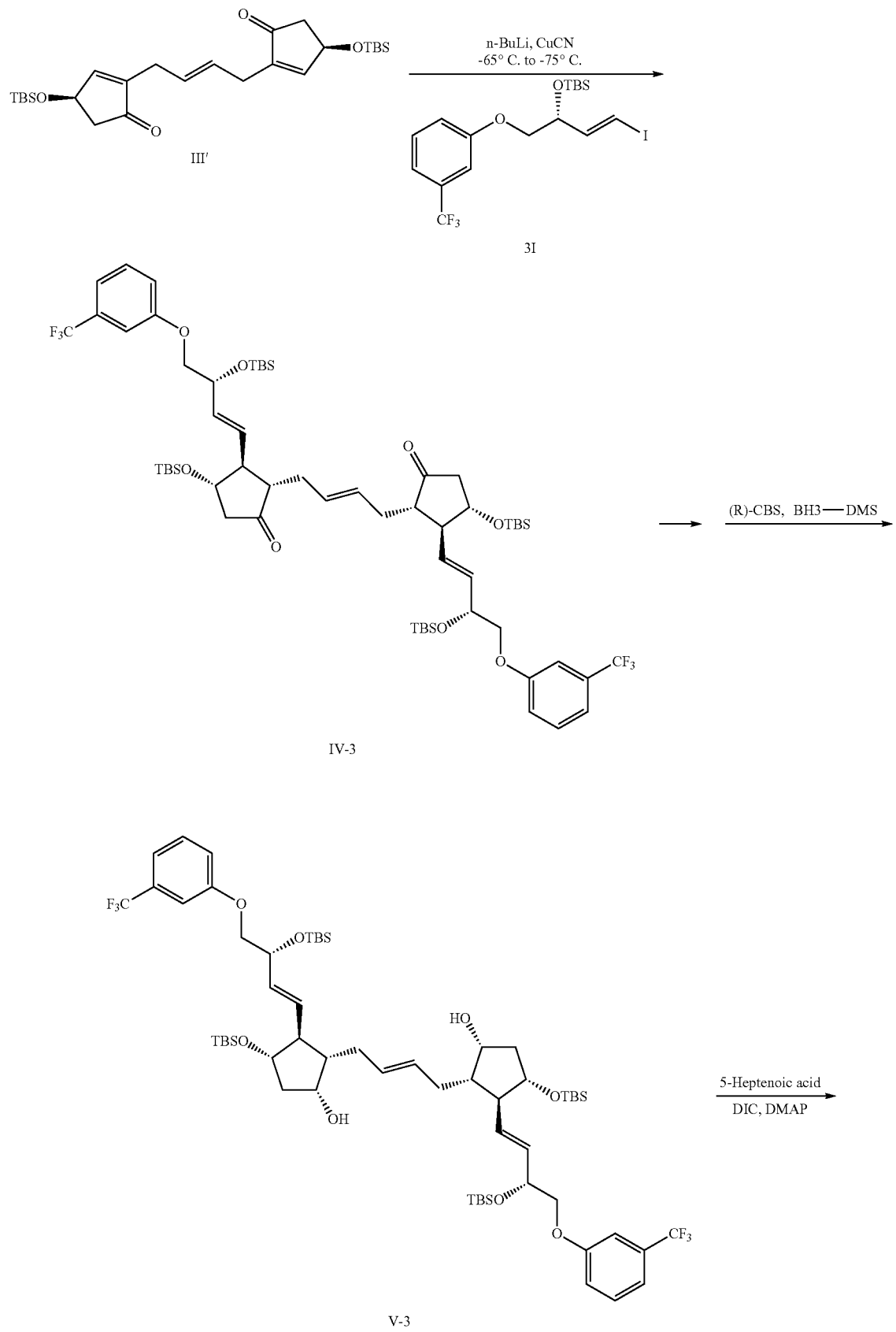

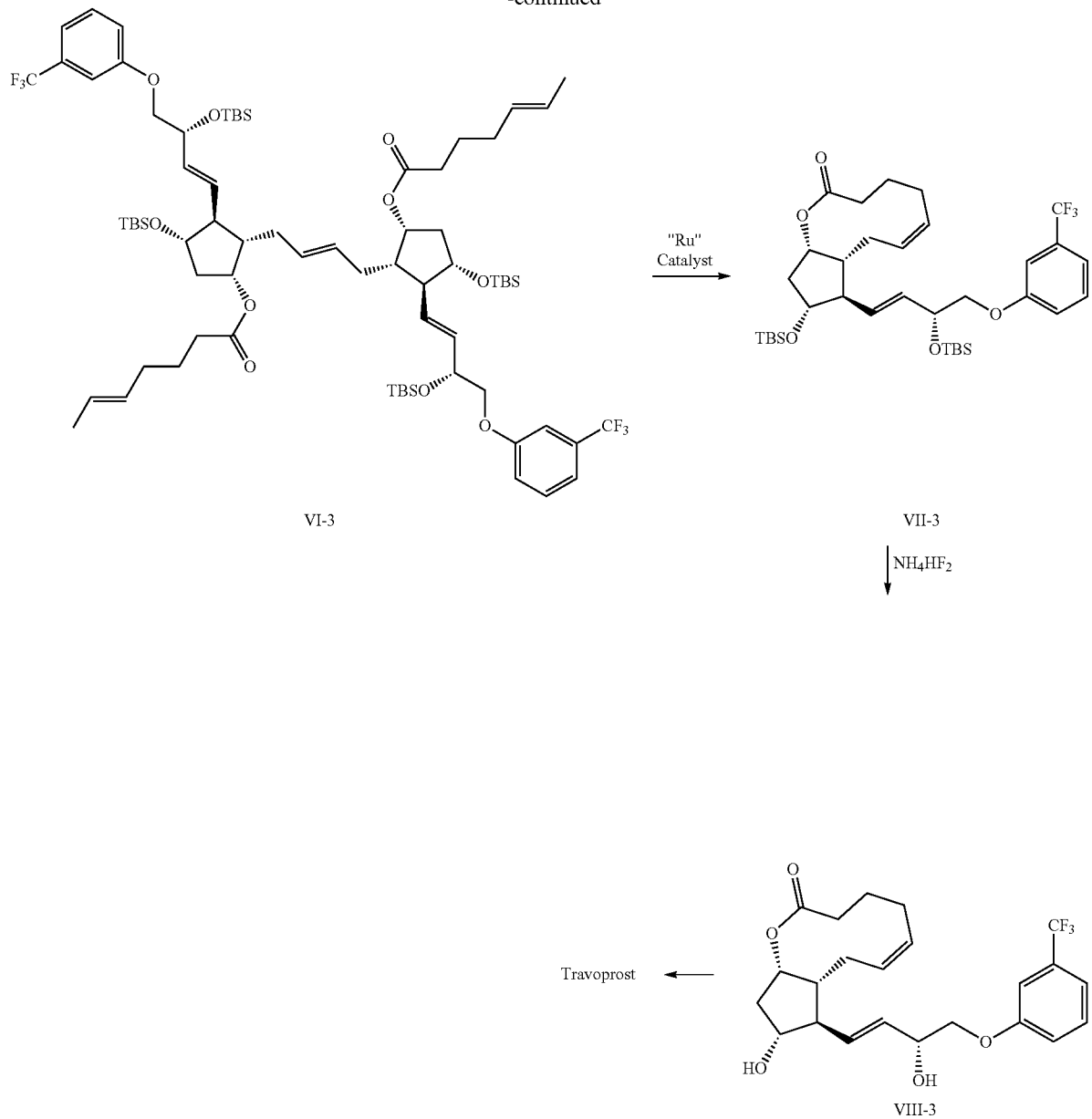

In yet some other embodiments, e.g., where R is group (4) of Table 1, the above described reaction sequence leads to the production of the lactone VIII-4 and ultimately tafluprost as outlined in Scheme 18. Compound (IV-4) can be produced from compound (I') via two routes; (a) via 1,4-addition of the copperlithium reagent (4I) from Table 2 to compound (I') followed by a cross metathesis reaction using metal catalysis, such as with tricyclohexylphosphine[1,3-bis(2,4,6-trimethylphenyl)imidazol-2-ylidene][3-phenyl-1H-inden-1-ylidene]ruthenium(II) dichloride, or (b) first via a metal-catalyzed cross metathesis reaction of compound (I') using the same catalyst to produce compound (III') followed by a double 1,4-addition of the copperlithium reagent (4I). The carbonyl groups in compound (IV-4) may then be reduced enantioselectively to provide the diol (V-4) using an enantioselective reducing reagent, such as (R)-(+)-2-methyl-CBS-oxazaborolidine [(R)—CBS] and borane dimethylsul- fide. Both hydroxyl groups of the resulting diol are then esterified with 5-heptenoic acid to produce compound (VI-4). This intermediate is subjected to an intra-molecular metathesis reaction using metal catalysis, such as tricyclohexylphosphine[1,3-bis(2,4,6-trimethylphenyl)imidazol-2-ylidene][3-phenyl-1H-inden-1-ylidene]ruthenium(II) dichloride, to produce the protected lactone (VII-4). Deprotection of this lactone with a suitable reagent, such as ammonium hydrogen difluoride, produces the lactone (VIII-4), the penultimate intermediate in the synthesis of tafluprost.

Opening of the lactone, which can be done under acidic or basic conditions, followed by esterification, or direct opening of the lactone with isopropoxide leads to the preparation of tafluprost.

Scheme 18. Synthesis of Tafluprost.
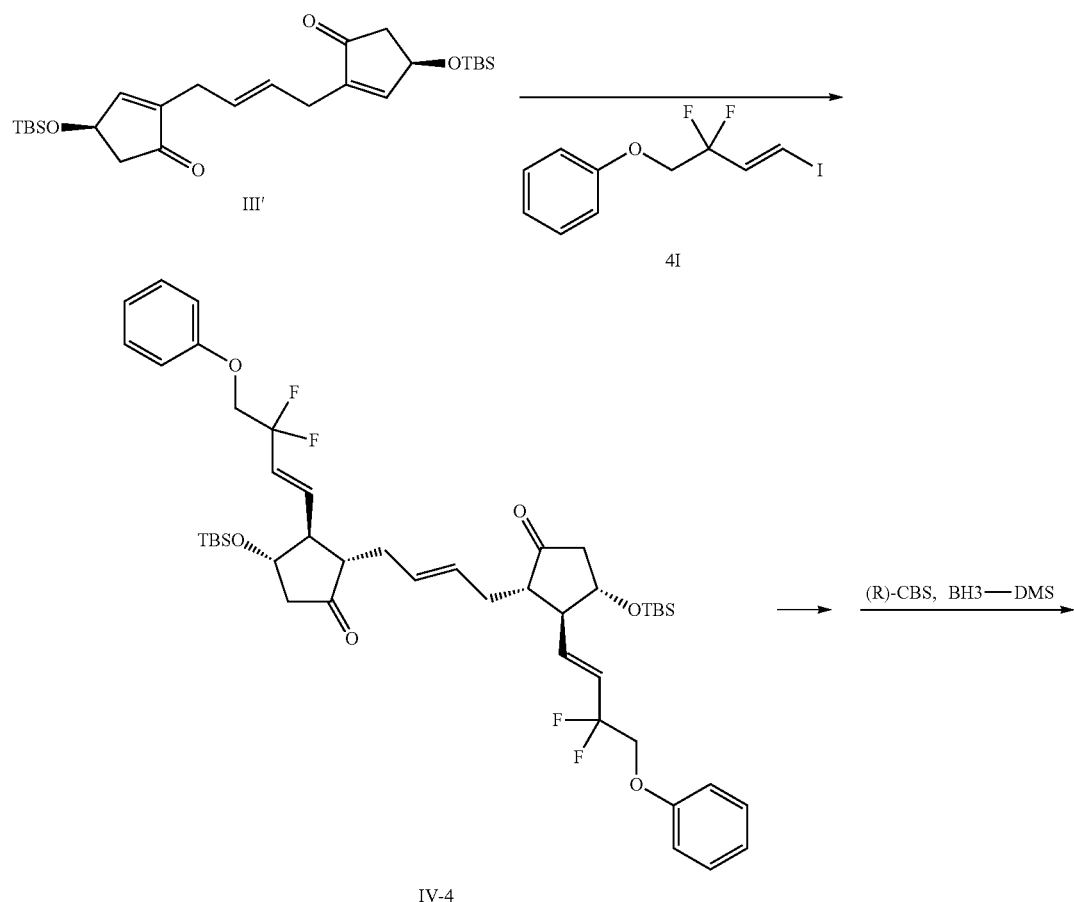
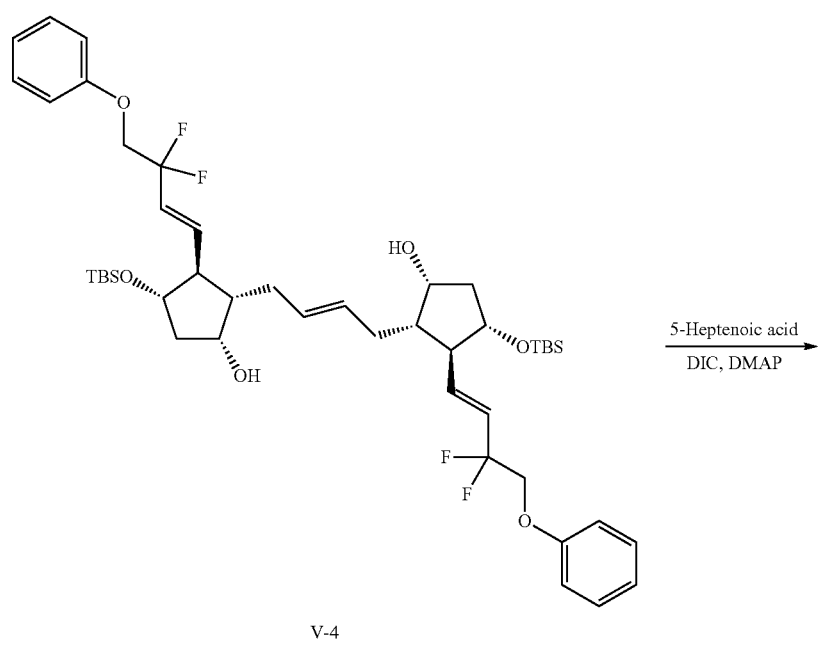

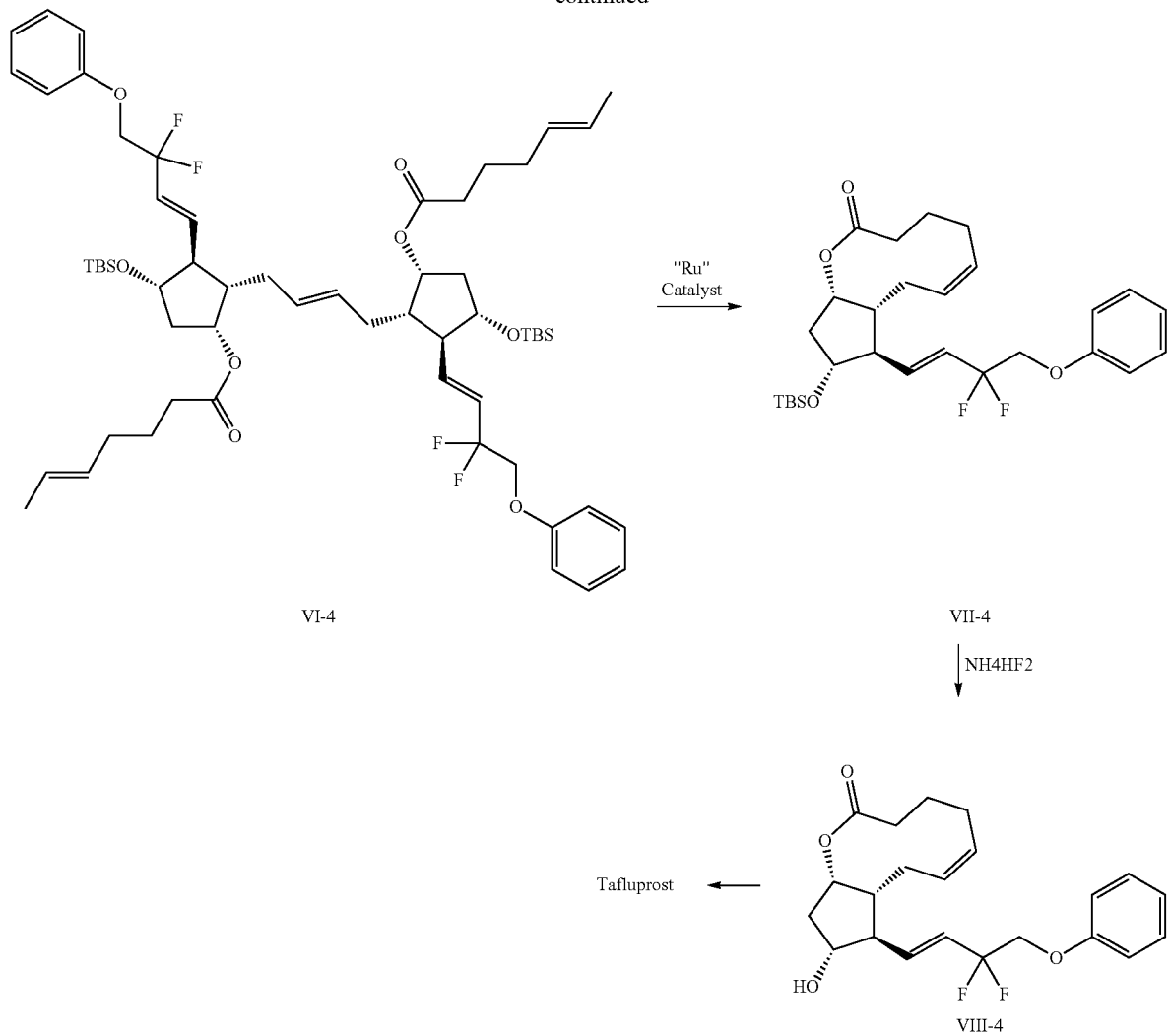

VI-4

VII-4

↓ NH4HF2

Tafluprost ←

VIII-4

In some other embodiments, e.g., where R is group (5) of Table 1, compounds such as compound VII-5, can be produced via the above described sequence of Scheme 1A. This compound can be used to prepare tafluprost via an alternative route, as outlined in Scheme 19. Compound VII-5 can be converted to compound VII-5A' by treating it with titanium trichloride in an aqueous ammonium acetate solution. The produced aldehyde VII-5A' is then reacted with diethyl-2-oxo-3-phenoxypropylphosphonate in the presence of a base. A variety of bases are suitable for this reaction ranging from mild, such as carbonate, to strong, such as sodium hydride. The carbonyl functionality may be converted to the corresponding difluoride via a variety of electrophilic fluorinating reagents such a $XeF_2$, DUST, and Deoxo-Fluor to provide difluorolactone VII-5C. Conversion of the difluorolactone intermediate VII-5C to tafluprost involves the removal of the TBDMS group and opening of the lactone to the isopropyl ester as described in other prostaglandin analogues above.

Scheme 19. Alternate synthesis of Tafluprost.

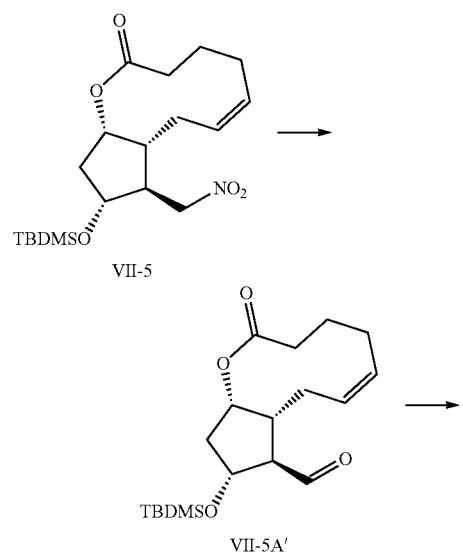

VII-5

VII-5A'

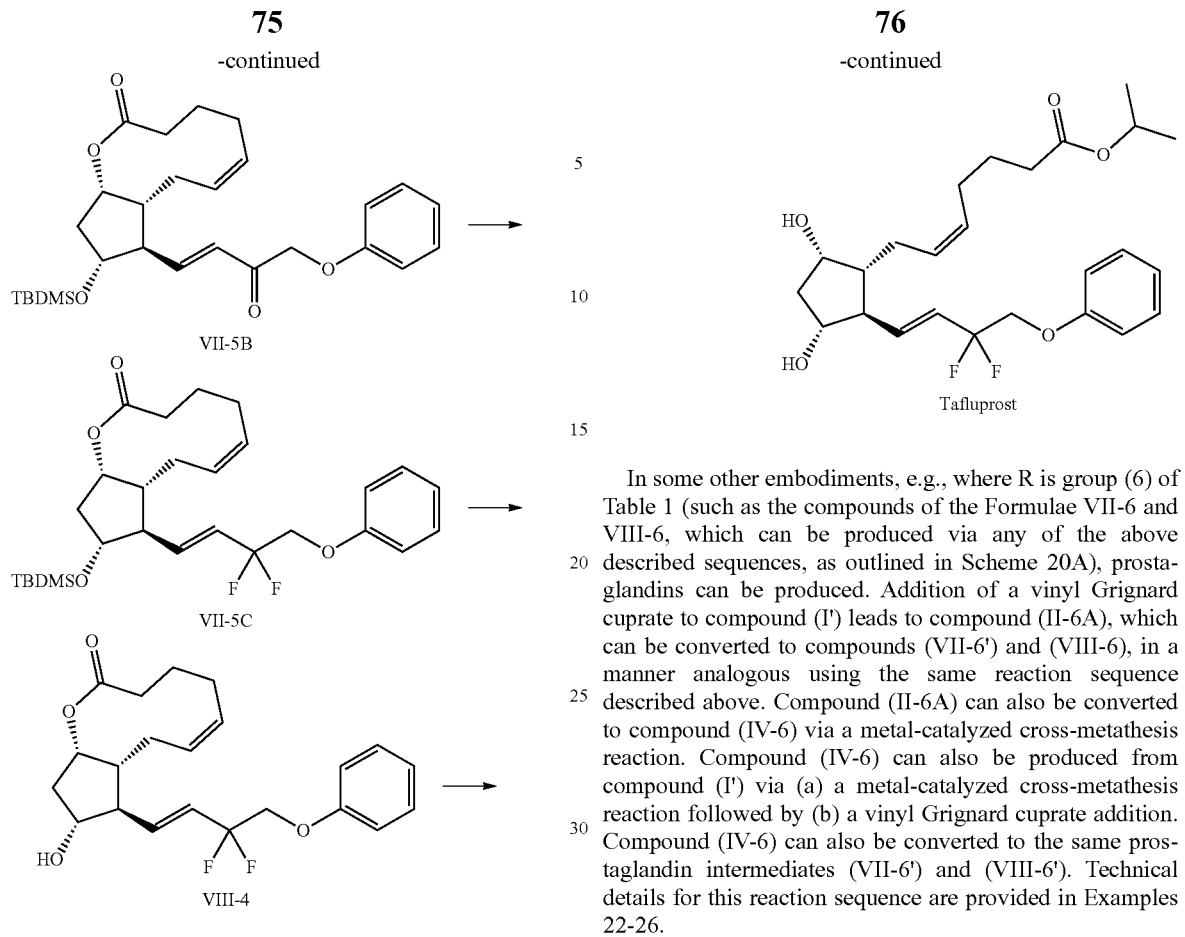

In some other embodiments, e.g., where R is group (6) of Table 1 (such as the compounds of the Formulae VII-6 and VIII-6, which can be produced via any of the above described sequences, as outlined in Scheme 20A), prostaglandins can be produced. Addition of a vinyl Grignard cuprate to compound (I') leads to compound (II-6A), which can be converted to compounds (VII-6') and (VIII-6), in a manner analogous using the same reaction sequence described above. Compound (II-6A) can also be converted to compound (IV-6) via a metal-catalyzed cross-metathesis reaction. Compound (IV-6) can also be produced from compound (I') via (a) a metal-catalyzed cross-metathesis reaction followed by (b) a vinyl Grignard cuprate addition. Compound (IV-6) can also be converted to the same prostaglandin intermediates (VII-6') and (VIII-6'). Technical details for this reaction sequence are provided in Examples 22-26.

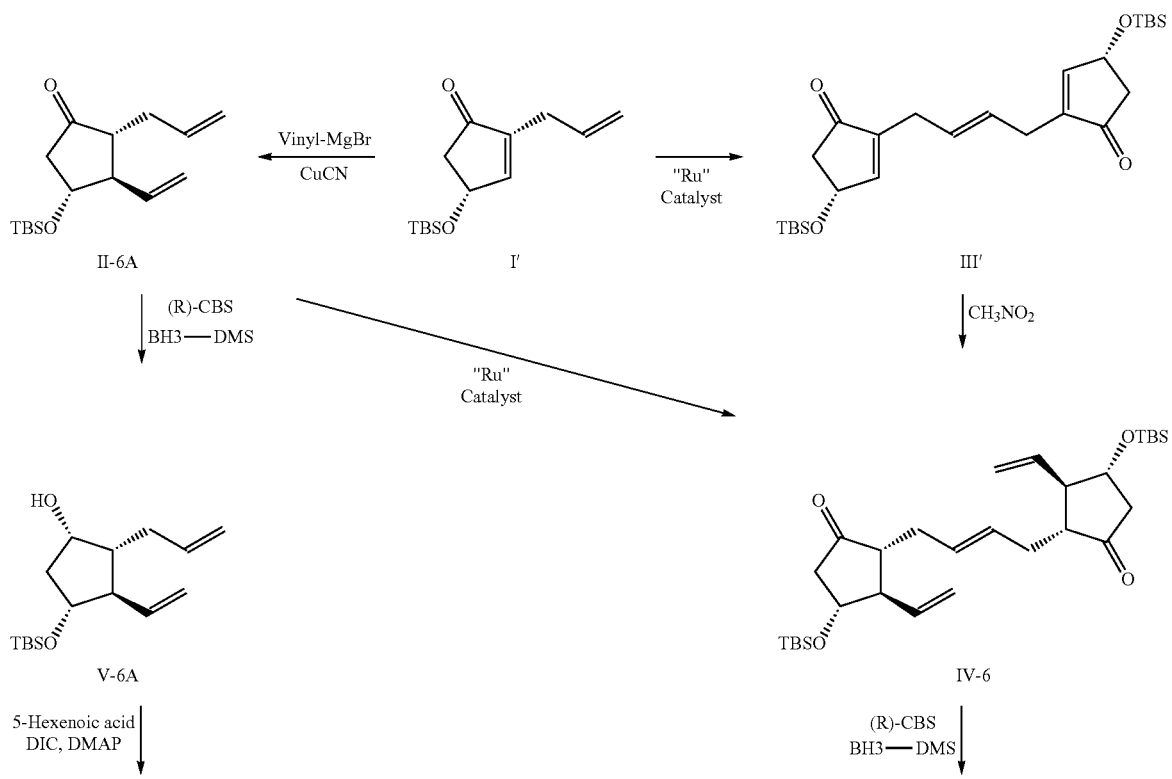

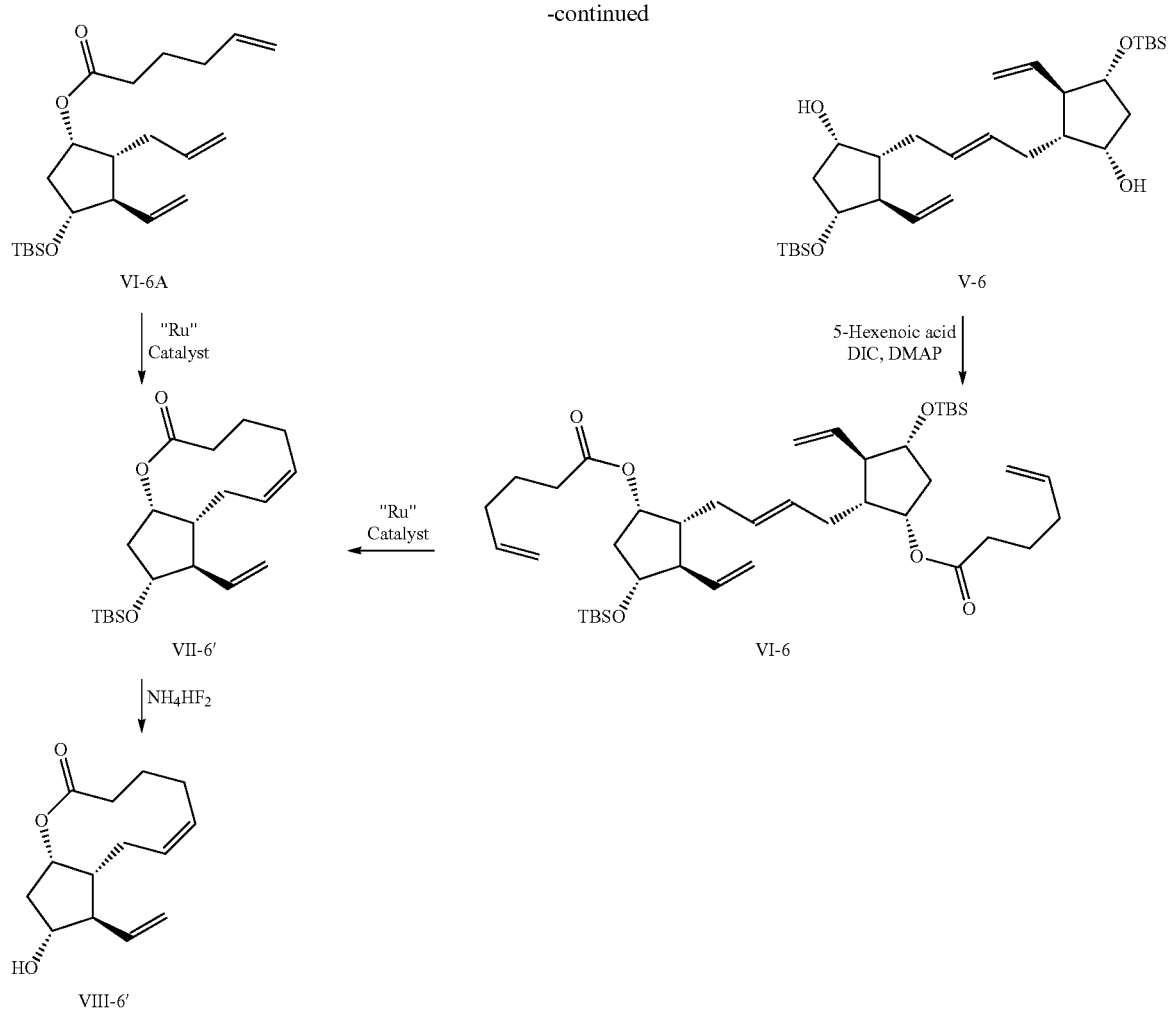
Yet in some other embodiments, suitable enones, such as the examples provided in Table 3 below, are used in a cross-metathesis reaction with compounds of the Formulas (VII-6) and (VIII-6) (e.g., compounds (VII-6') and (VIII-6')) to produce compounds of Formula (XI) as outlined in Scheme 20B below.
TABLE 3
Exemplary "Enone" Stuctures.
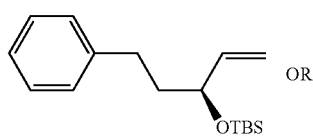 [SMILES: C=C[C@H](CCc1ccccc1)O[Si](C)(C)C(C)(C)C]
2K
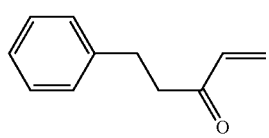
TABLE 3-continued
Exemplary "Enone" Stuctures.
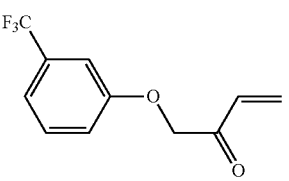 [SMILES: C=CC(=O)COc1cccc(C(F)(F)F)c1]
3K
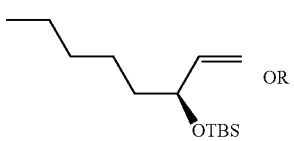 [SMILES: C=C[C@H](CCCCC)O[Si](C)(C)C(C)(C)C]
10K

TABLE 3-continued
Exemplary "Enone" Stuctures.
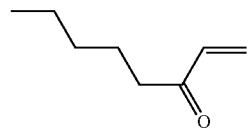
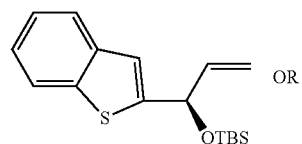 [SMILES: C=C[C@@H](O[Si](C)(C)C(C)(C)C)c1cc2ccccc2s1]
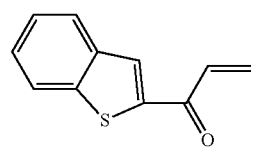
TABLE 3-continued
Exemplary "Enone" Stuctures.
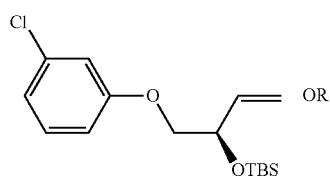 [SMILES: C=C[C@H](COc1cccc(Cl)c1)O[Si](C)(C)C(C)(C)C]  13K
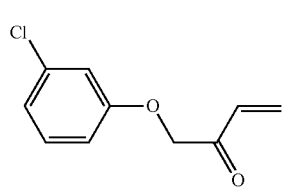  12K
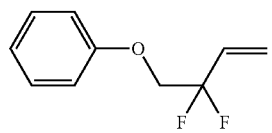  4K
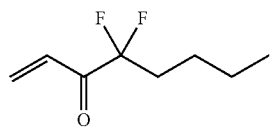  7K
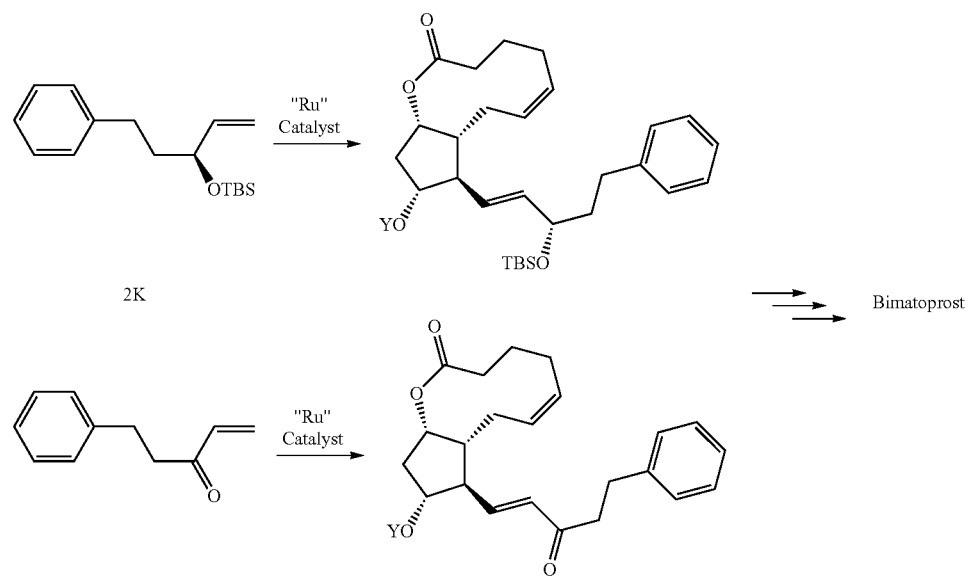
Scheme 20B. Synthesis of Compounds of Formula (XI).

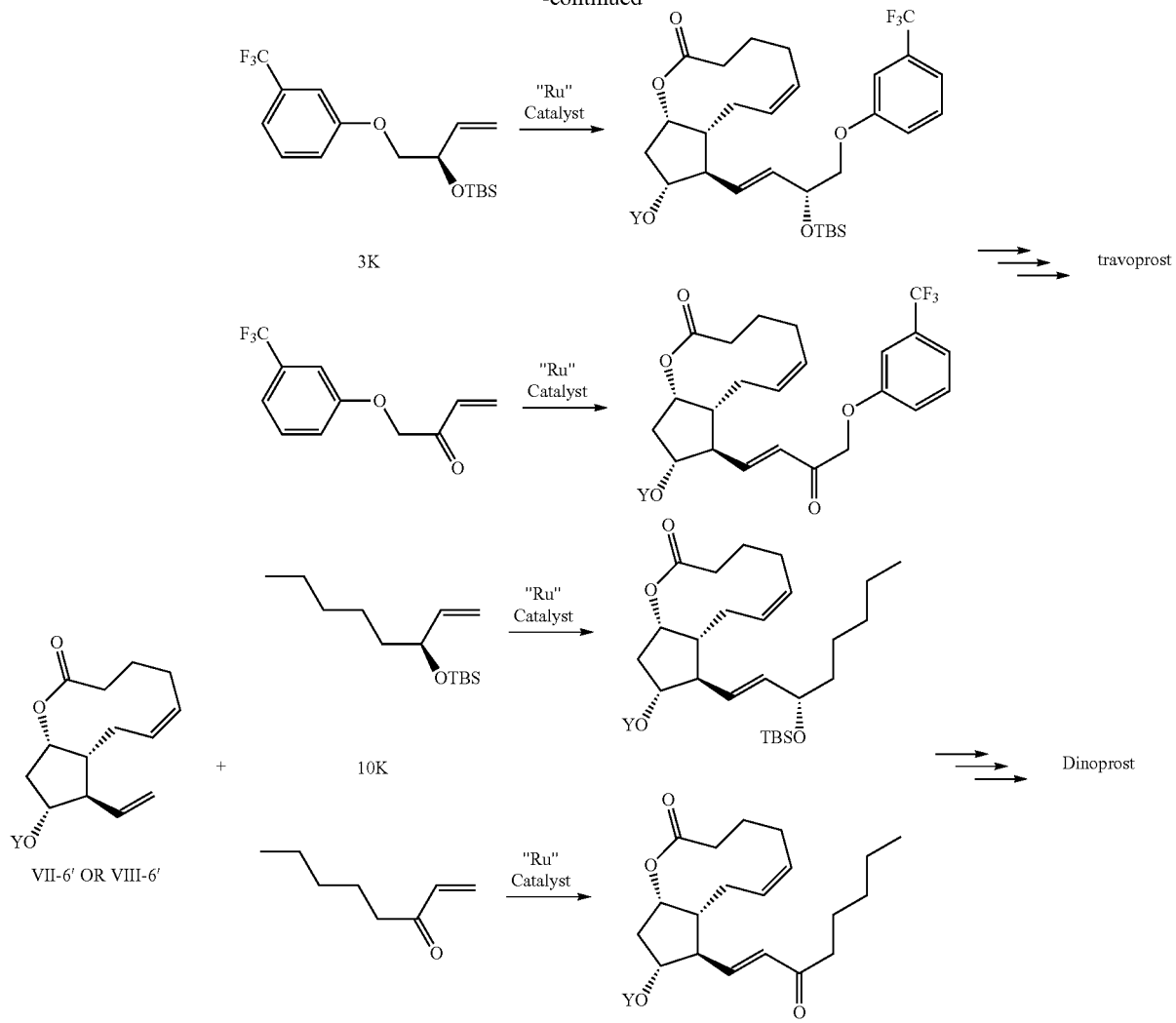
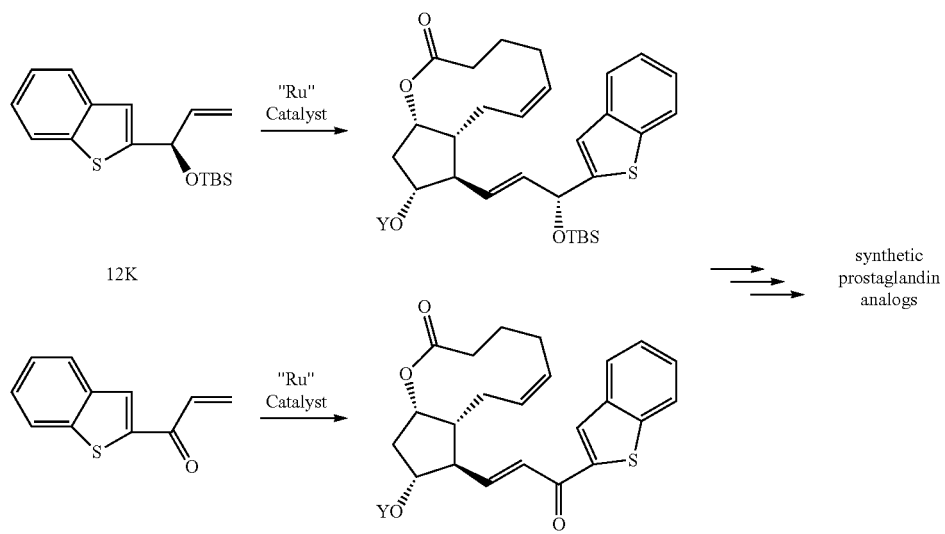

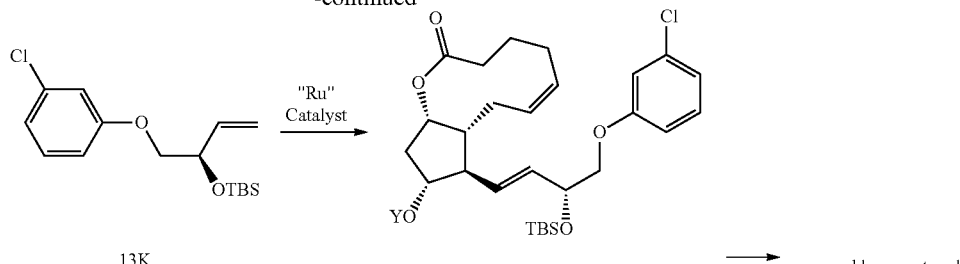

13K

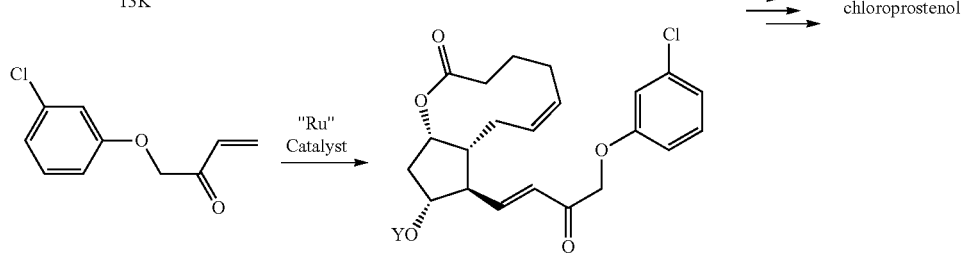

→→→ chloroprostenol

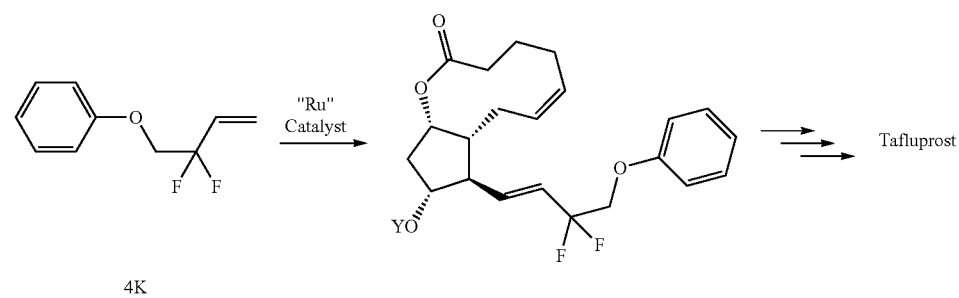

4K

→→ Tafluprost

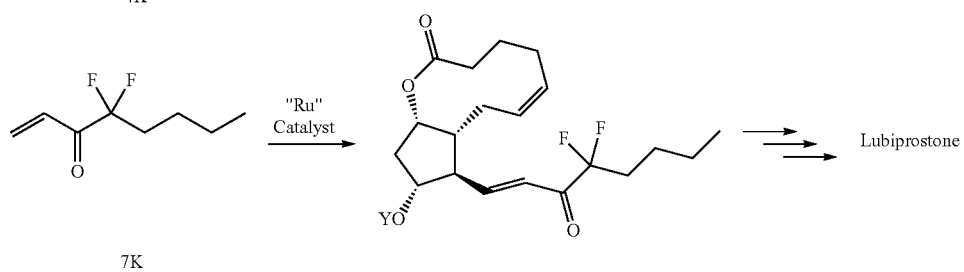

7K

→→→ Lubiprostone

In some other embodiments, e.g., where R is group (7) of Table 1, the above described reaction sequence leads to the production of the precursor lactone VII-7B for the synthesis of lubiprostone as outlined in Scheme 21. Compound (IV-7) can be produced from compound (I') via two routes; (a) via 1,4-addition of the copperlithium reagent (7I) of Table 2 to compound (I') followed by a cross metathesis reaction using metal catalysis, such as using tricyclohexylphosphine[1,3-bis(2,4,6-trimethylphenyl)imidazol-2-ylidene][3-phenyl-1H-inden-1-ylidene]ruthenium(II) dichloride, or (b) first via a metal-catalyzed cross metathesis reaction of compound (I') using the same catalyst to produce compound (III') followed by a double 1,4-addition of the copperlithium reagent (7I). The carbonyl groups in compound (IV-7) may then be reduced enantioselectively to produce the diol (V-7) using an enantioselective reducing reagent, such as (R)-(+)-2-methyl-CBS-oxazaborolidine [(R)—CBS] and borane dimethylsulfide. Both hydroxyl groups of the resulting diol are then esterified with 5-heptenoic acid to produce compound (VI-7). This intermediate is subjected to an intra-molecular metathesis reaction using metal catalysis, such as using tricyclohexylphosphine[1,3-bis(2,4,6-trimethylphenyl)imidazol-2-ylidene][3-phenyl-1H-inden-1-ylidene]ruthenium (II) dichloride, to produce the protected lactone (VII-7). Selective removal of the TBDMS group using t-butylammonium fluoride leads to compound (VIII-7A). Oxidation of the unprotected hydroxy group can be accomplished using a variety of oxidizing reagents, one being 2-iodobenzoic acid (IBX). The compound (VII-7B) is anintermediate in the synthesis of lubiprostone. Chemical process details for the synthesis of the lactone (VII-7B) are provided in Examples 16-28.

Scheme 21. Synthesis of Lubiprostone lactone precursor VII-7B

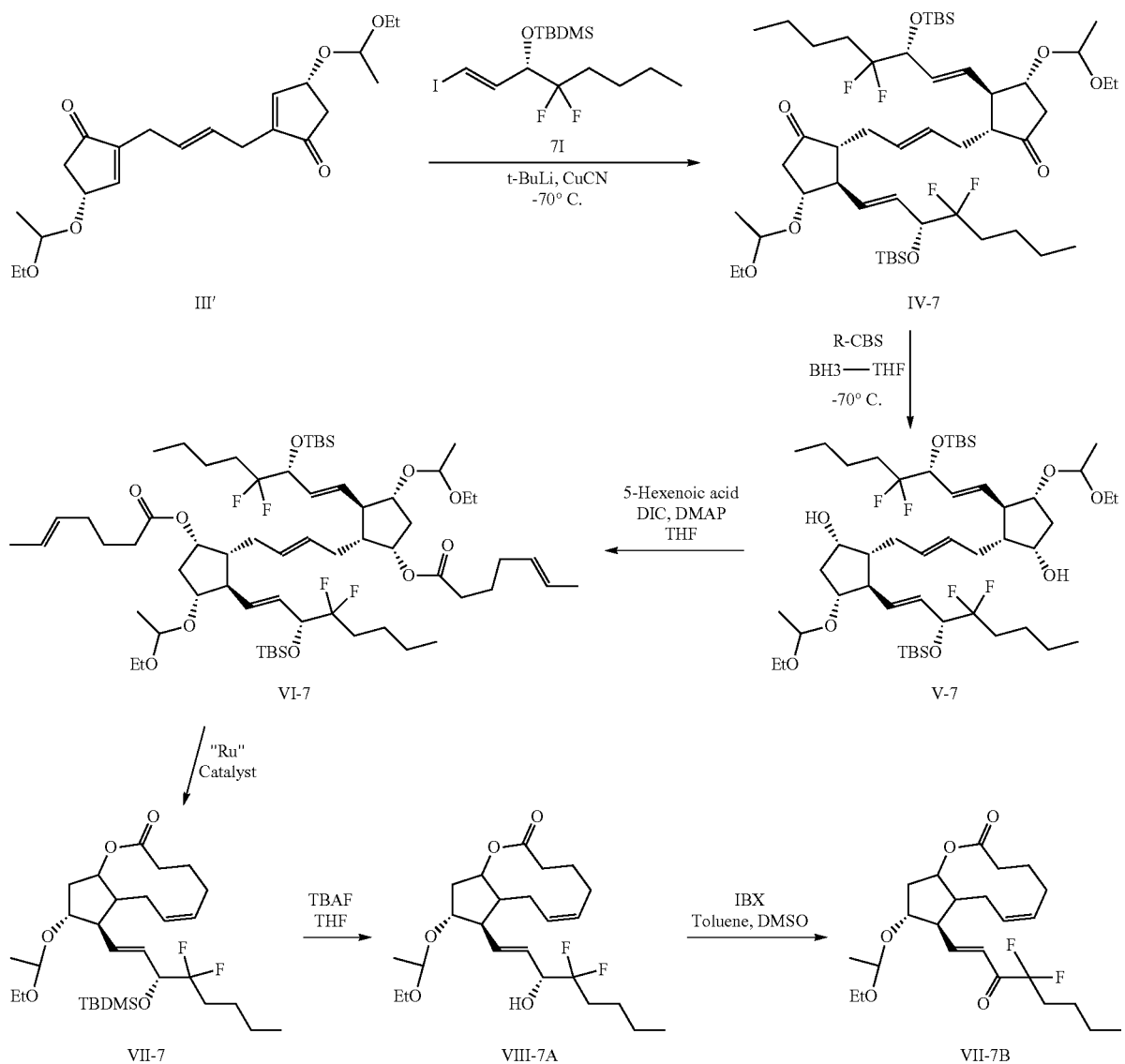

In yet some other embodiments, e.g., where R is group (5) of Table 1, the above described reaction sequence leads to the production of the precursor nitromethyl lactone (VIII-5), which also leads to the synthesis of the above precursor lactone (VII-7B) as outlined in Scheme 22. Reaction of compound (I') with nitromethane (5I) in the presence of a base, such a 1,1,3,3-tetramethylguanidine, leads to compound (II-5). Enantioselective reduction of the carbonyl group using an enantioselective reducing reagent, such as (R)-(+)-2-methyl-CBS-oxazaborolidine [(R)—CBS] and borane dimethylsulfide produces the alcohol (V-5A). Esterification using 5-hexenoic acid followed by an intra-molecular metathesis reaction using metal catalysis, such as with tricyclohexylphosphine[1,3-bis(2,4,6-trimethylphenyl)imidazol-2-ylidene][3-phenyl-1H-inden-1-ylidene]ruthenium (II) dichloride, produces the protected lactone (VII-5).

The same lactone (VII-5) is also accessible via the compound (IV-5), which can be produced from compound (I') via two routes; (a) via 1,4-addition of the nitromethane (5I) in the presence of a base, such a 1,1,3,3-tetramethylguanidine to compound (I') followed by a cross metathesis reaction using metal catalysis, such as using tricyclohexylphosphine[1,3-bis(2,4,6-trimethylphenyl)imidazol-2-ylidene][3-phenyl-1H-inden-1-ylidene]ruthenium(II) dichloride, or (b) first via a metal-catalyzed cross metathesis reaction of compound (I') using the same catalyst to produce compound (III') followed by a double 1,4-addition of nitromethane (5I) in the presence of a base, such a 1,1,3,3-tetramethylguanidine.

The carbonyl groups in compound (IV-5) may then be reduced enantioselectively to produce the diol (V-5) using an enantioselective reducing reagent, such as (R)-(+)-2-methyl-CBS-oxazaborolidine [(R)—CBS] and borane dimethylsulfide. Both hydroxyl groups of the resulting diol are then esterified with 5-heptenoic acid to produce compound (VI-5). This intermediate is subjected to an intra-molecular metathesis reaction using metal catalysis, such as using tricyclohexylphosphine[1,3-bis(2,4,6-trimethylphenyl)imidazol-2-ylidene][3-phenyl-1H-inden-1-ylidene]ruthenium (II) dichloride, to produce the protected lactone (VII-5). Removal of the TBDMS protecting group with ammonium dihydrogen fluoride leads to compound VIII-5, an intermediate in the synthesis of the lubiprostone precursor lactone (VII-7B).

The synthesis of the compound (VII-7B) from the above lactone (VIII-5) is accessible by (a) converting the nitromethyl functionality in the compound (VIII-5) to an aldehyde using titanium trichloride in an aqueous ammonium acetate solution, (b) reacting the aldehyde (VIII-5A) with diethyl 3,3-difluoro-2-oxohexylphosphonate in the presence of a base such as sodium hydride to produce compound (VIII-7), and (c) protecting the free hydroxy group with ethyl vinyl ether in the presence of catalytic amount of an acid, such as p-toluenesulfonic acid. Chemical process details for the synthesis of the lactone (VII-7B) are provided in Examples 16-28.

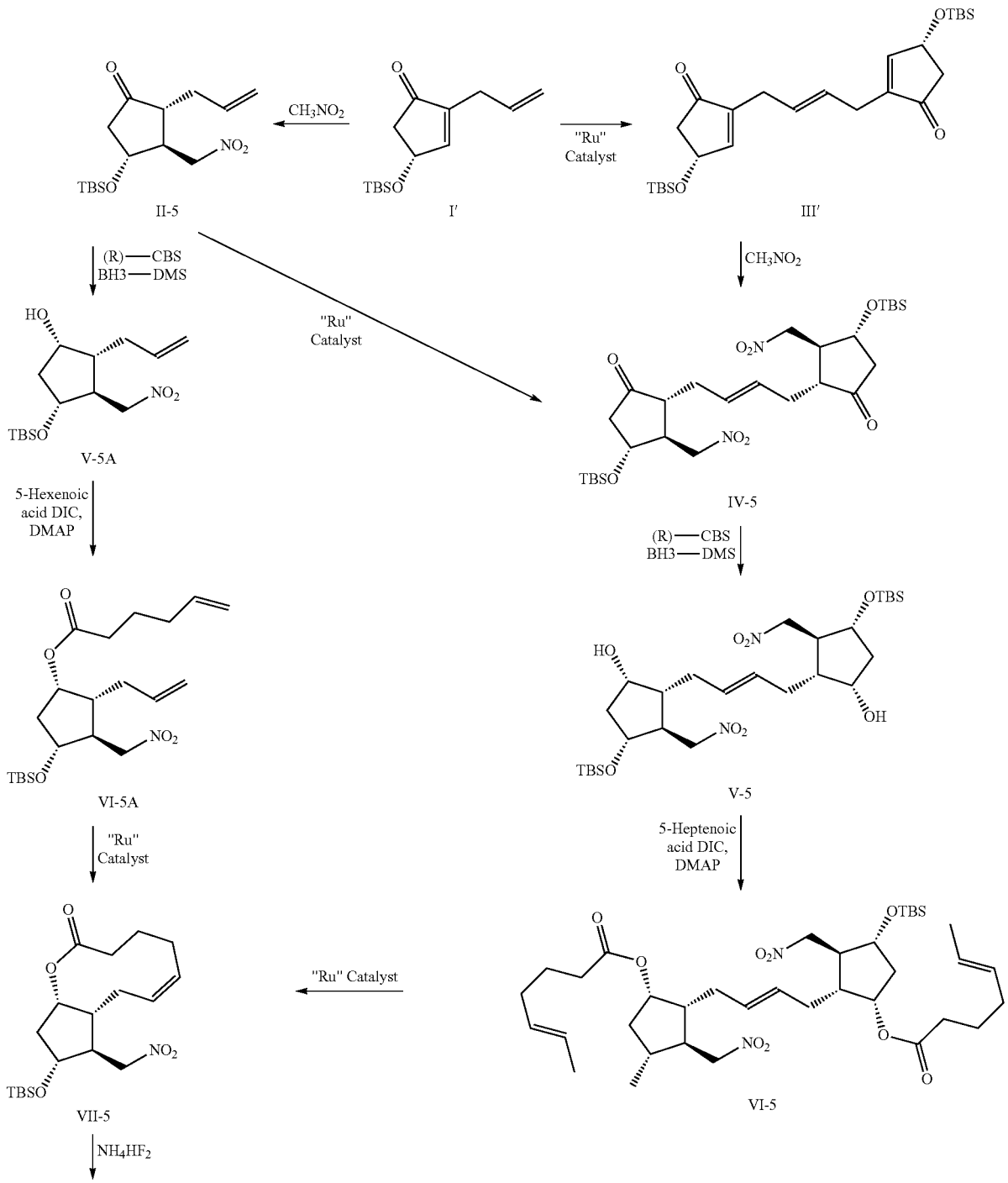

Scheme 22. Alternate synthesis of the Lubiprostone lactone precursor (VIII-7B)

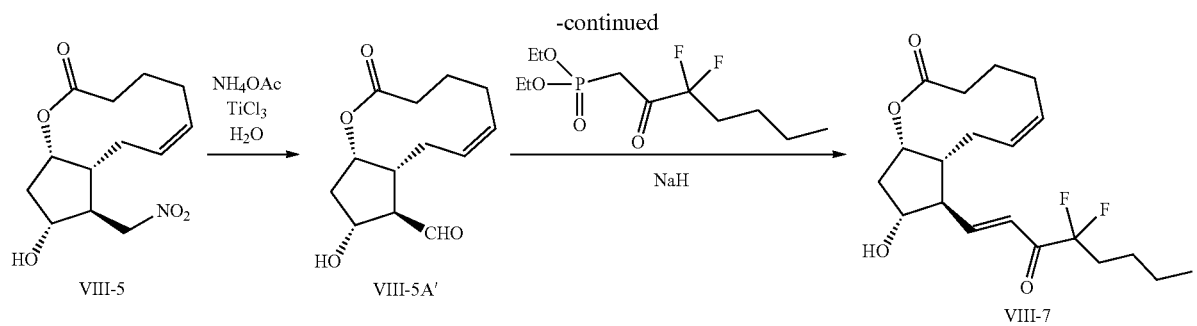

In some other embodiments, a process for producing lubiprostone from the precursor lactone compound (VII-7B), which can be produced via three different variations of the above described general sequence, is disclosed. This process, which is outlined in Scheme 23 proceeds as follows. The two double bonds of the precursor lactone (VII-7B) are hydrogenated using palladium on carbon as the catalyst to produce the compound (VII-7C). The carbonyl group is then reduced to the corresponding alcohol (VII-7D) and the lactone is hydrolyzed using lithium hydroxide to produce the acid (LUB-1). Chemical process details for the synthesis of lubiprostone are provided in Examples 29-34.

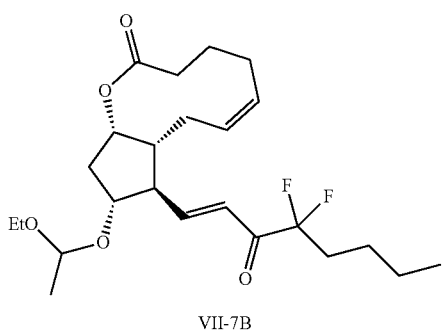 [SMILES: CCCCC(F)(F)C(=O)/C=C/[C@@H]1[C@H]2C/C=C\CCCC(=O)O[C@H]2C[C@H]1OC(C)OCC ; "VII-7B"]

Scheme 23. Synthesis of Lubiprostone from the lactone precursor (VII-7B)

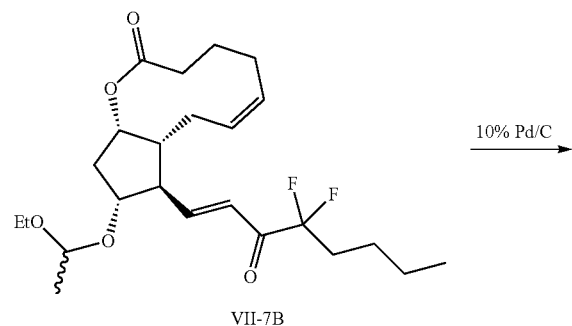

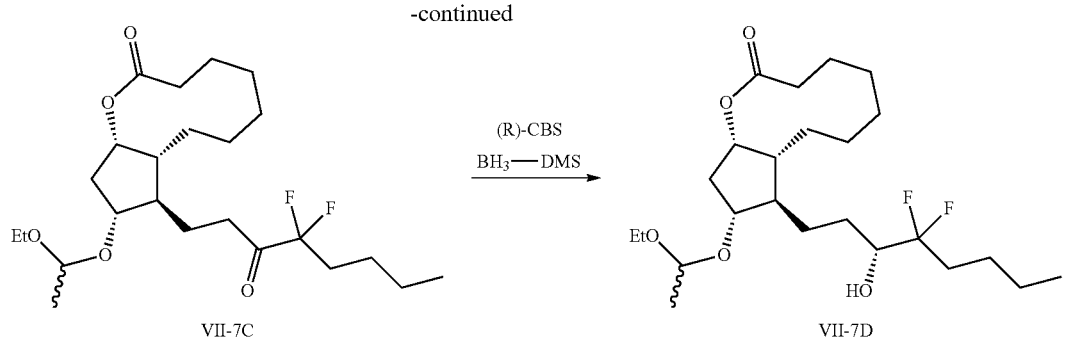

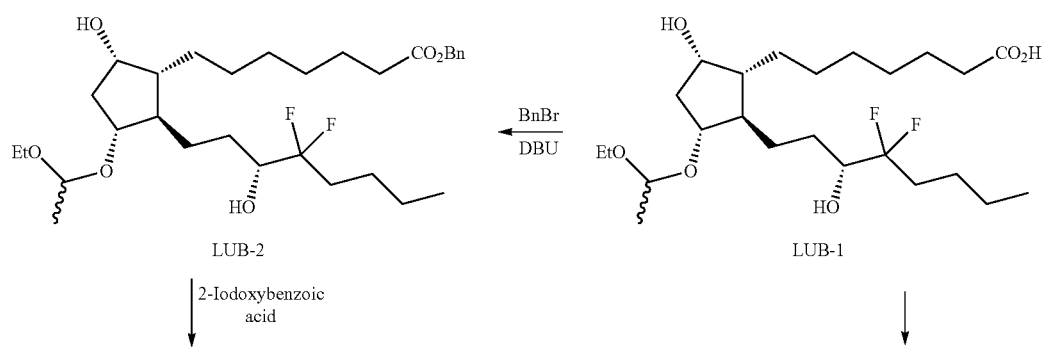

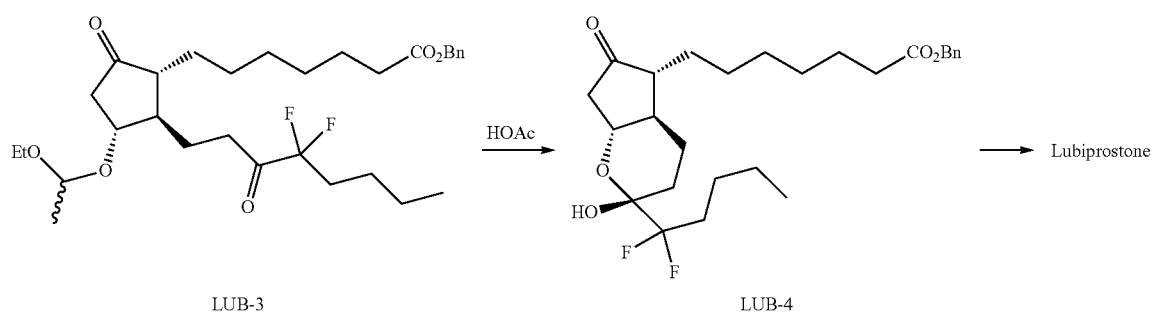

In yet some other embodiments, a process for producing lubiprostone as outlined in Scheme 24 is disclosed. It comprises converting compound (I') to compound (LUB-6) by (a) performing a cross metathesis reaction between compound (I') and an ester of hexenoic acid to produce compound (X'), and (b) performing a 1,4-addition to the cyclopentenone using a suitable organocuprate reagent to produce compound (LUB-5), which is then debenzylated to afford the intermediate (LUB-6). From this point, the lubiprostone process proceeds via two possible routes, as also shown in Scheme 24. The first entails an oxidation of the hydroxy group of the lower side chain to a ketone using IBX to provide compound (LUB-7) followed by deprotection of the cyclopentenone hydroxy group to afford lubiprostone. The second route proceeds via the lubiprostone benzyl ester (LUB-4), which is debenzylated in the final step of the process. The lubiprostone benzyl ester (LUB-4) is produced by (a) esterifying the compound (LUB-6), (b) oxidizing the lower side chain alcohol, and (c) deprotecting the protected hydroxy group of the cyclopentenone. Technical details are provided in Examples 35-40.

Scheme 24. Alternate synthesis of Lubiprostone
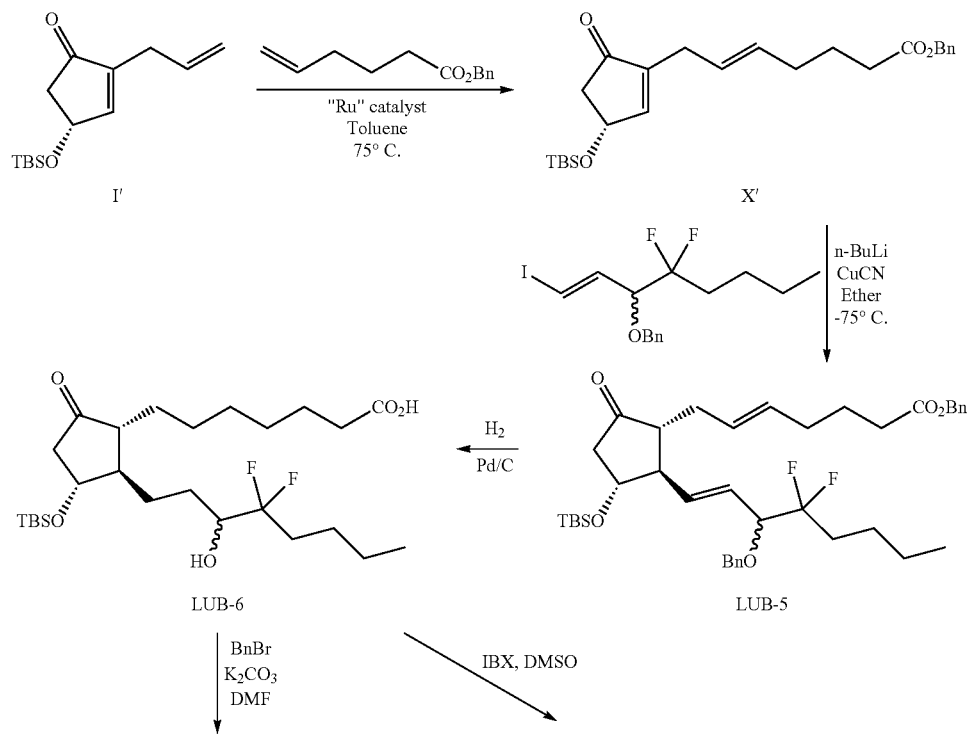
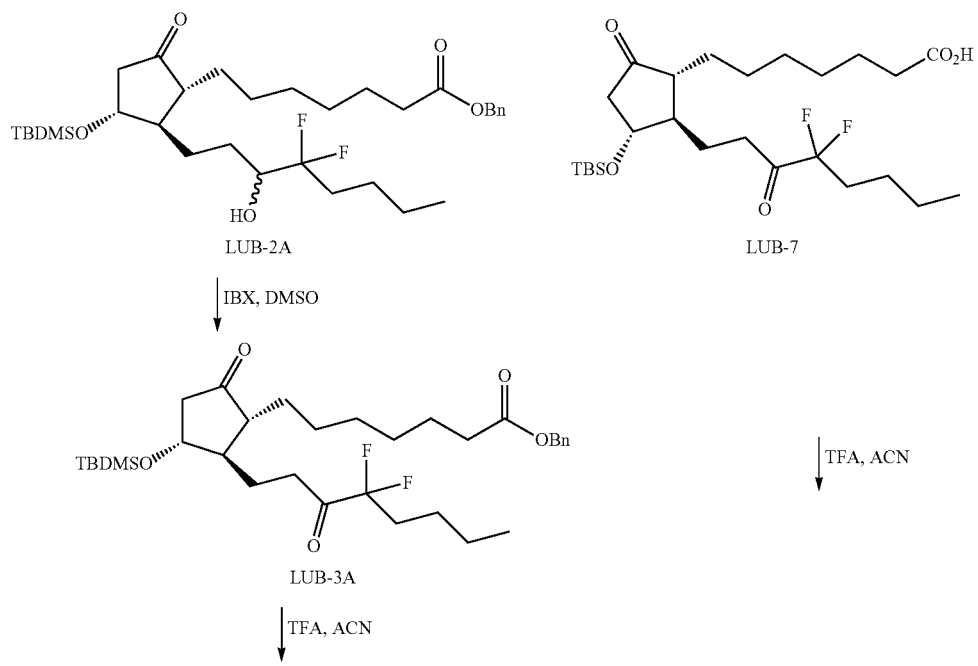

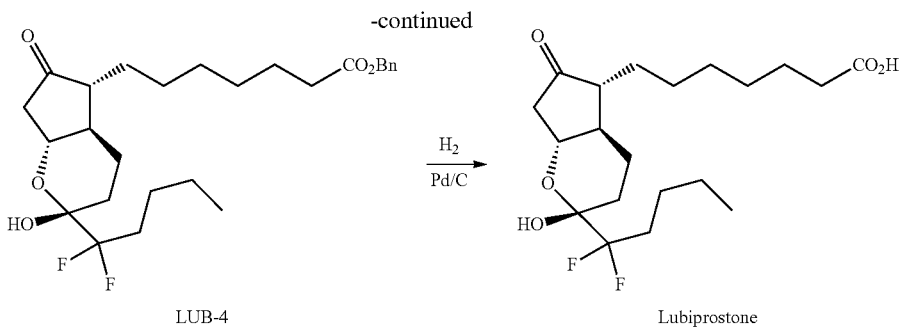

Also, in some other embodiments, a process for producing lubiprostone as outlined in Scheme 25 is disclosed. It comprises of (a) converting compound (VII-6″) to compound (XIV-6′) by treating it with a base, such as lithium hydroxide, in aqueous media, (b) esterifying the free acid with the appropriate chiral allylic alcohol to form compound (XV′), (c) subjecting compound (XV′) to a metathesis reaction using a ruthenium catalyst to produce the macrocyclic lactone (XVI′), (d) hydrogenating the two double bonds using a suitable catalyst, such a palladium-on-carbon catalyst, to afford the saturated macrocyclic lactone (XVI′-A), and (e) opening the macrocyclic lactone with a suitable base, such as lithium hydroxide, to produce the lubiprostone intermediate (LUB-1A). From this intermediate, lubiprostone may be produced via either of the routes described above, i.e. directly or via the benzyl ester. Technical details are provided in Examples 51-55.

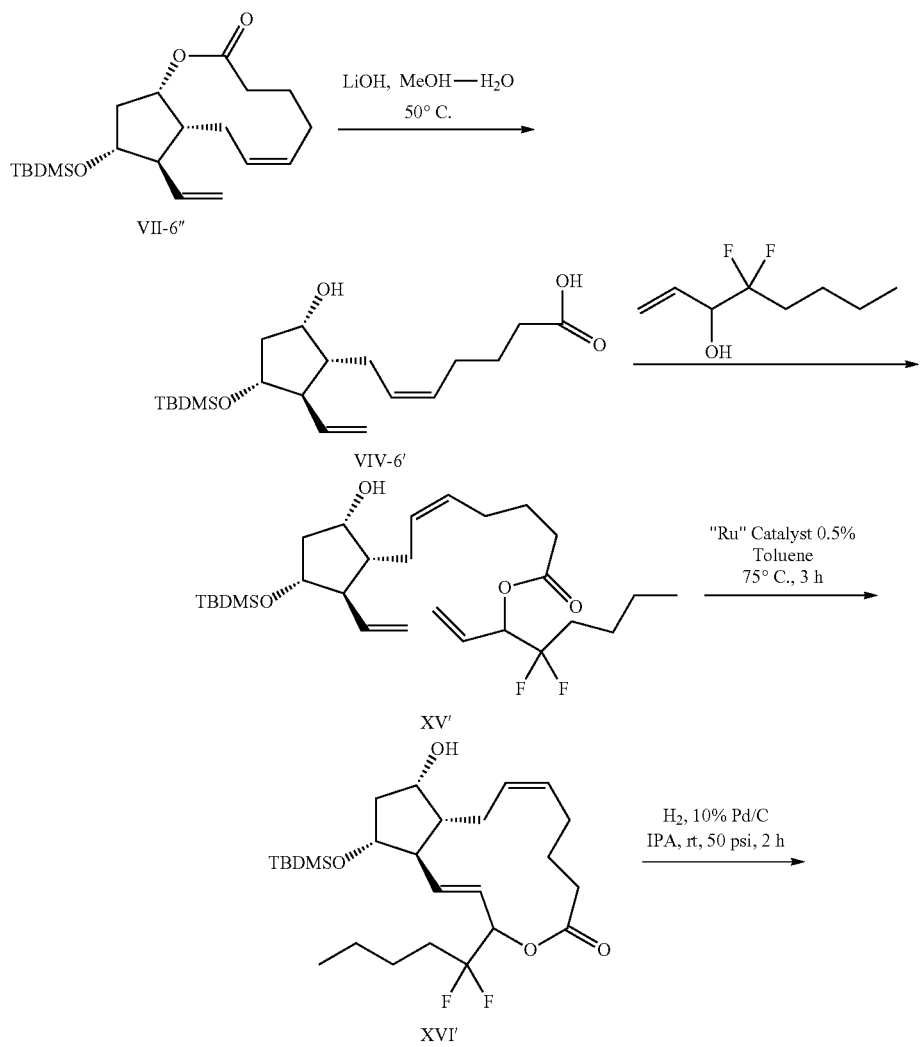

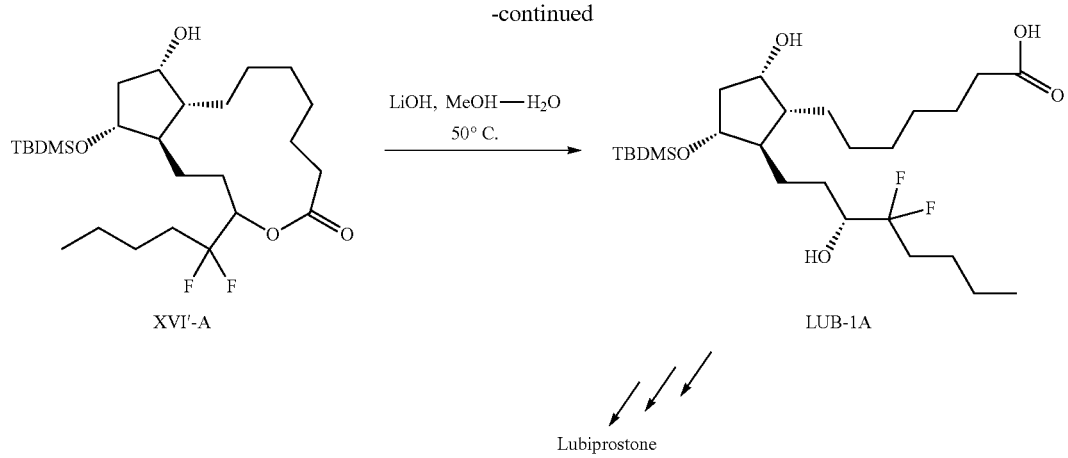

In some other embodiments, e.g., where R is group (8) of Table 1, the above described reaction sequence leads to the production of unoprostone as outlined in Scheme 26. Compound (IV-8) can be produced from compound (I') via two routes: (a) via 1,4-addition of the copperlithium reagent (8I) to compound (I') followed by a cross metathesis reaction using metal catalysis, such as with tricyclohexylphosphine [1,3-bis(2,4,6-trimethylphenyl)imidazol-2-ylidene][3-phenyl-1H-inden-1-ylidene]ruthenium(II) dichloride, or (b) first via a metal-catalyzed cross metathesis reaction of compound (I') using the same catalyst to produce compound (III') followed by a double 1,4-addition of the copperlithium reagent (8I). The carbonyl groups in compound (IV-8) may then be reduced enantioselectively to produce the diol (V-8) using an enantioselective reducing reagent, such as (R)-(+)-2-methyl-CBS-oxazaborolidine [(R)—CBS] and borane dimethylsulfide. Both hydroxyl groups of the resulting diol are then esterified with 5-heptenoic acid to produce compound (VI-8). This intermediate is subjected to an intramolecular metathesis reaction using metal catalysis, such as using tricyclohexylphosphine[1,3-bis(2,4,6-trimethylphenyl)imidazol-2-ylidene][3-phenyl-1H-inden-1-ylidene]ruthenium(II) dichloride, to produce the protected lactone (VII-8). Deprotection of this lactone with a suitable reagent, such as ammonium hydrogen difluoride, produces the lactone (VIII-8), the penultimate intermediate in the synthesis of unoprostone. Chemical process details for the synthesis of the lactone (VIII-8) are provided in Examples 41-47. Opening of the lactone, which can be done under acidic or basic conditions, followed by esterification or direct opening of the lactone with isopropoxide leads to the preparation of unoprostone.

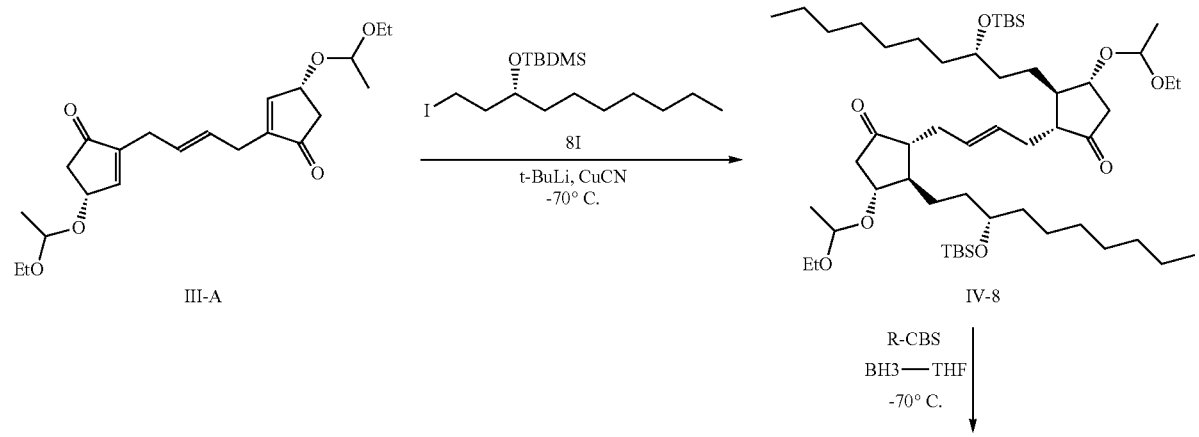

Scheme 26. Synthesis of Unoprostone isopropyl ester.

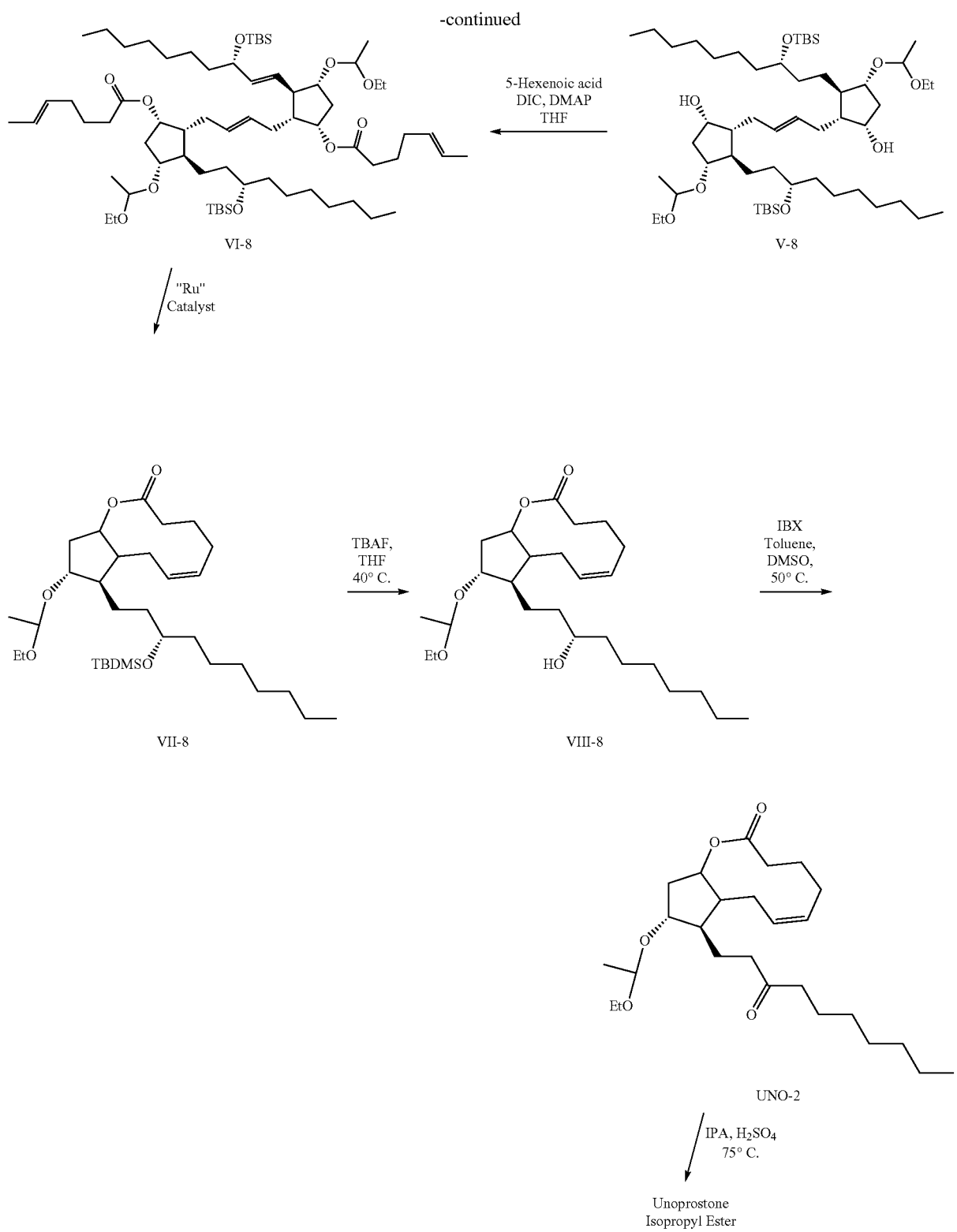

In some further embodiments, an alternate process for producing unoprostone isopropyl ester, which also is based on a cross-metathesis reaction, is disclosed as outlined in Scheme 27. This short process comprises: (a) hydrolyzing the lactone ring in compound (VIII-6') to form the acid (XIV-6), (b) esterifying the acid to form the isopropyl ester compound (XIV-6A), (c) performing a metal-catalyzed cross-metathesis reaction with heptyl vinyl ketone to produce compound (UNO-1), and (d) selectively hydrogenating the unsaturated double bond in the molecule to afford the unoprostone isopropyl ester. Technical details for this process are provided in Examples 48-50.

Scheme 27. Synthesis of Unoprostone from vinyl lactone (VIII-6)

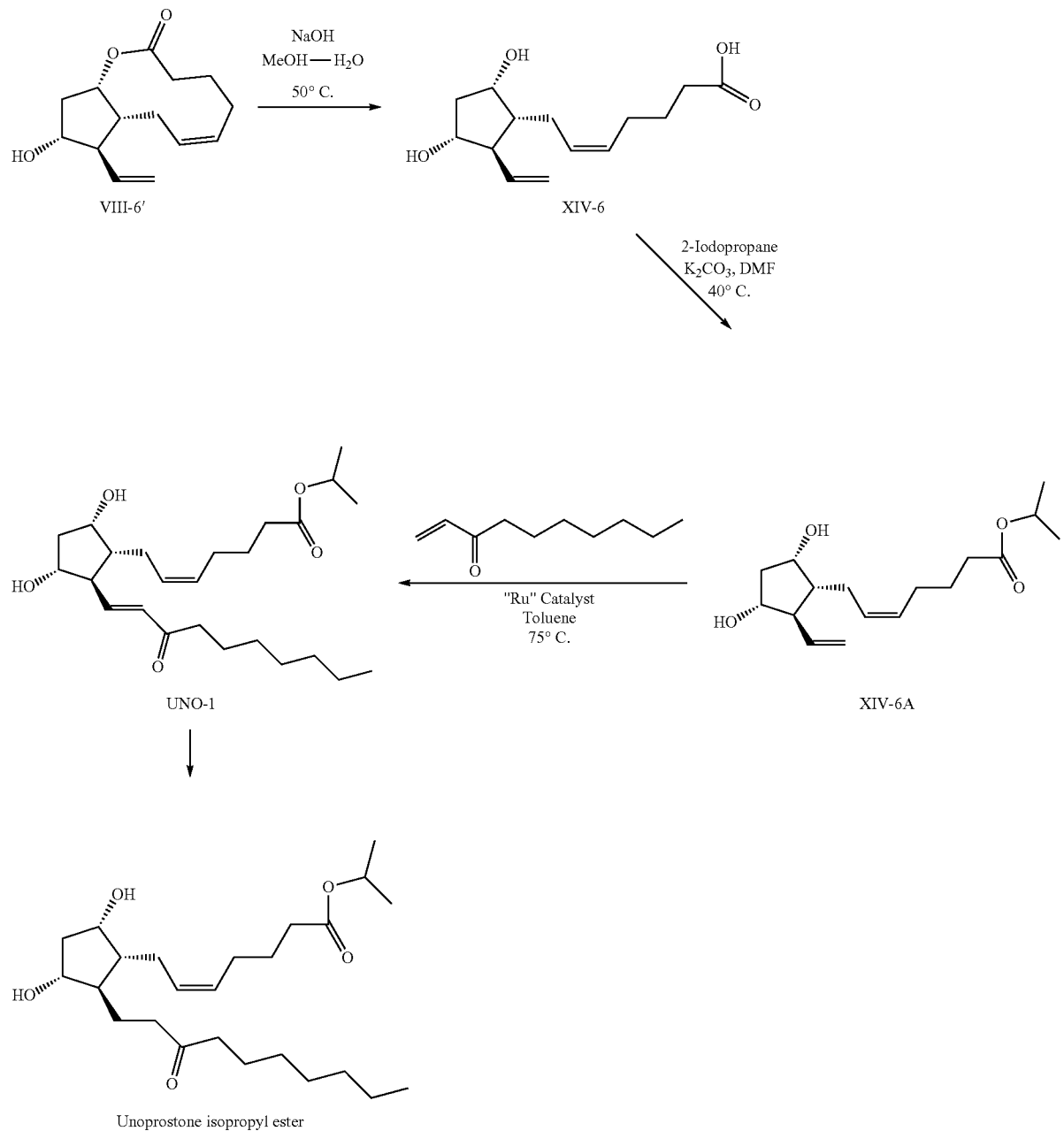

In some other embodiments, e.g., where R is group (10) of Table 1, the above described reaction sequence leads to the production of dinoprost as outlined in Scheme 28. Compound (IV-10) can be produced from compound (I') via two routes: (a) via 1,4-addition of the copperlithium reagent (10I) to compound (I') followed by a cross metathesis reaction using metal catalysis, such as tricyclohexylphosphine[1,3-bis(2,4,6-trimethylphenyl)imidazol-2-ylidene][3-phenyl-1H-inden-1-ylidene]ruthenium(II) dichloride, or (b) first via a metal-catalyzed cross metathesis reaction of compound (I') using the same catalyst to produce compound (III') followed by a double 1,4-addition of the copperlithium reagent (10I). The carbonyl groups in compound (IV-10) may then be reduced enantioselectively to produce the diol (V-10) using an enantioselective reducing reagent, such as (R)-(+)-2-methyl-CBS-oxazaborolidine [(R)—CBS] and borane dimethylsulfide. Both hydroxyl groups of the resulting diol are then esterified with 5-heptenoic acid to produce compound (VI-10). This intermediate is subjected to an intra-molecular metathesis reaction using metal catalysis, such as using tricyclohexylphosphine[1,3-bis(2,4,6-trimethylphenyl)imidazol-2-ylidene][3-phenyl-1H-inden-1-ylidene]ruthenium(II) dichloride, to produce the protected lactone (VII-10). Deprotection of this lactone with a suitable reagent, such as ammonium hydrogen difluoride, produces the lactone (VIII-10), the penultimate intermediate in the synthesis of dinoprost. Hydrolysis of the lactone using lithium hydroxide leads to the production of dinoprost.

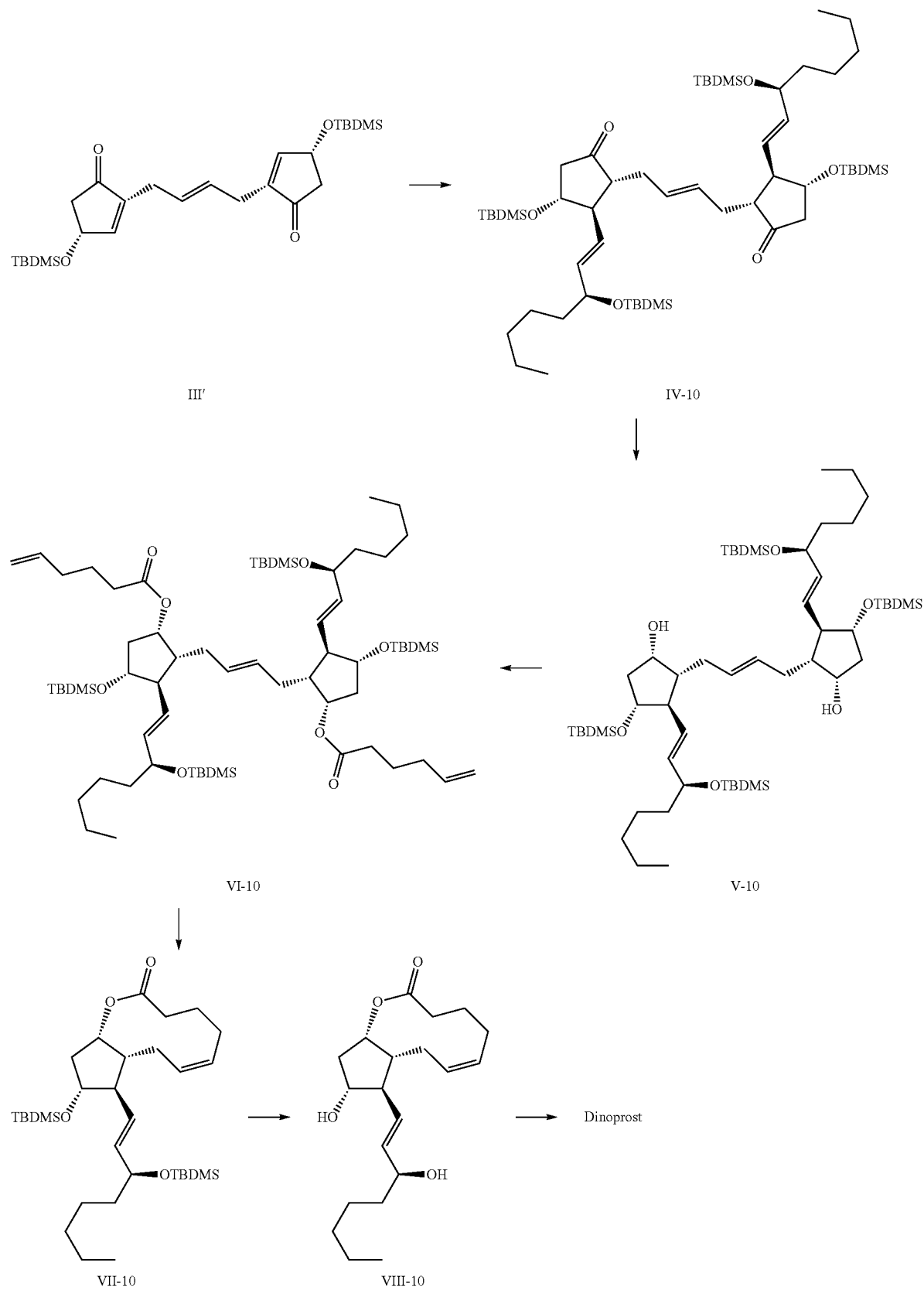
Scheme 28. Synthesis of Dinoprost.

In yet some other embodiments, e.g., where R is group (13) of Table 1, the above described reaction sequence leads to the production of chloprostenol in a manner analogous to the other prostaglandin analogues above as described in Scheme 29.
Scheme 29. Synthesis of Cloprostenol.
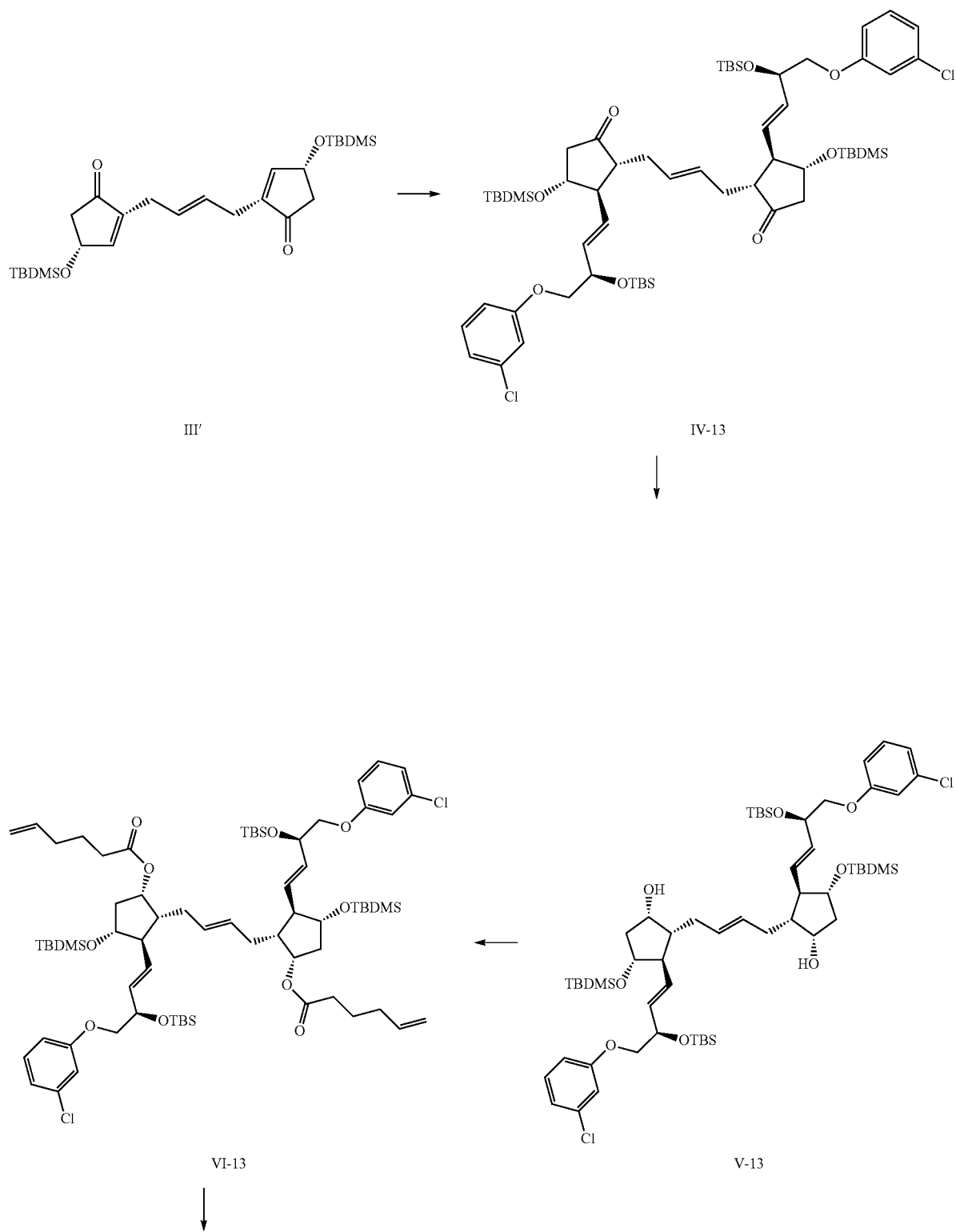

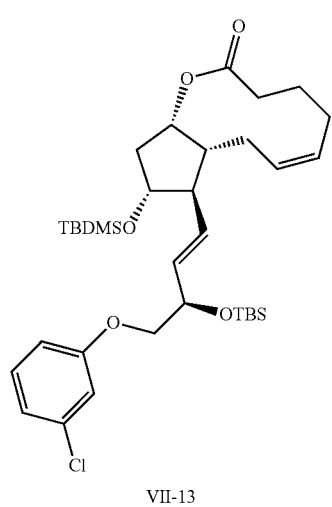

VII-13

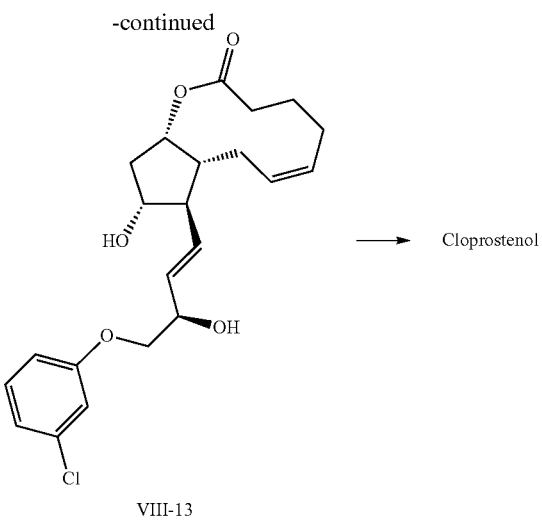

VIII-13 → Cloprostenol

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1. Preparation of Compound (III')

A round bottom flask was charged with 25 g of compound (I') and 100 ml of anhydrous toluene under argon. The reaction mixture was heated to 70° C. and 100 mg of tricyclohexylphosphine[1,3-bis(2,4,6-trimethylphenyl) imidazol-2-ylidene][3-phenyl-1H-inden-1-ylidene]ruthenium (II) dichloride (CAS #: 254972-49-1) was added to it. The reaction was stirred at 70° C. over 12 h. Ethyl vinyl ether (5 ml) was added and reaction was stirred for 30 minutes and concentrated under vacuum. The crude product was purified via column chromatography on Silica gel to yield 22 g of compound (III') as light yellow solid.

Example 2. Preparation of Compound (IV-1)

A reaction flask was charged with 1.0 g of the vinyl iodide derivative 1I and 5 mL of anhydrous ether. The reaction solution was cooled to −70° C. and 3.1 mL of 1.7 M solution of n-BuLi in hexanes was added slowly maintaining the temperature below −65° C. during the course of the addition. The reaction was stirred at −70° C. for 2.5 h. A separate flask was charged with 0.466 g of CuCN and 5 mL of anhydrous ethyl ether under a nitrogen atmosphere. The mixture was cooled to −70° C. and 2.5 mL of a 1.6 M solution of MeLi in ethyl ether was added to it slowly. The cooling bath was removed and the mixture was allowed to warm up to −15° C., at which temperature it was stirred for an additional 45 minutes. The mixture was then cooled down to −70° C. and combined with the first solution (vinyllithium reagent) under nitrogen. The resulting mixture was warmed up to −40° C. and stirred at this temperature for 45 minutes. It was then cooled down to −70° C. and a solution of 0.476 g of compound (III') in 5 mL of anhydrous ethyl ether was added dropwise. Reaction was stirred at −70° C. for 2 h. The cooling bath was removed and the reaction was quenched with a saturated NH$_4$Cl solution. It was then allowed to warm up to −10° C. at which temperature it was stirred for ~2 h. The reaction mixture was filtered through Celite and transferred to separatory funnel. The layers were separated, and the organic layer was dried over sodium sulfate, filtered and concentrated under vacuum. The crude product was purified via column chromatography on Silica gel to yield 0.75 g of compound (IV-1).

Example 3. Preparation of Compound (V-1)

A reaction flask was charged with 2 g of compound (II-1), 10 ml anhydrous toluene, and 50 mg tricyclohexylphosphine [1,3-bis(2,4,6-trimethylphenyl)imid-azol-2-ylidene][3-phenyl-1H-inden-1-ylidene]ruthenium(II) dichloride, and stirred at 75° C. under an atmosphere of argon for 4 h. The reaction mixture was cooled to room temperature. A different reaction flask was charged with 4.1 ml R—CBS 1M/toluene and 4.1 ml BH$_3$ THF 1M/THF. The mixture was cooled to −78° C. and the first reaction mixture was added to the flask at −70 C. The mixture was stirred for 1 h at −78° C. and quenched with 5 ml MeOH. The mixture was diluted with 50 ml 0.5M HCl and extracted with 2×50 ml MTBE. The combined organics were washed with 10 ml brine, dried over sodium sulfate and concentrated in vacuum to afford 2 g compound (V-1).

Example 4. Preparation of Compound (VI-1)

A reaction flask was charged with 2 g compound (V-1) in 8 ml anhydrous THF, 470 mg 5-heptenoic acid, 50 mg DMAP, and 520 mg DIC added. The mixture was stirred for 20 hours at ambient temperature. The solvent was removed under vacuum and the crude product was purified on silica gel to afford 1.8 g compound (VI-1).

Example 5. Preparation of Compound (VII-1)

A reaction flask was charged with 1.8 g compound 3 in 180 ml anhydrous toluene and 50 mg tricyclohexylphosphine[1,3-bis(2,4,6-trimethylphenyl)imidazol-2-ylidene][3-phenyl-1H-inden-1-ylidene]ruthenium(II) dichloride. The mixture was stirred for 4 h at 75° C. It was then cooled to ambient temperature and treated with 2 ml vinyl ethyl ether. The solvent was removed under vacuum. The crude product was purified on silica gel column to afford 600 mg of compound (VII-1).

Example 6. Preparation of Compound (VIII-1)

A reaction flask was charged with 600 mg LAT 4 and 230 mg of $NH_4HF_2$ in 5 ml THF/5 mlMeOH. The mixture was stirred at 40° C. for 20 h. It was the w diluted with 50 ml water and extracted with 2×20 ml MTBE. The organic layer were dried over sodium sulfate and concentrated in vacuum. The crude product was purified on silica gel column to afford 200 mg of compound (VIII-1).

Example 7. Preparation of Compound (II-2)

A reaction flask was charged with 86.5 g of the vinyl iodide derivative 21 and 400 mL of anhydrous ether. Reaction mixture was cooled to −70° C. and 107.5 mL of 2.5 M solution of n-BuLi in hexanes was added slowly maintaining the temperature below −65° C. during the course of the addition. The reaction was stirred at −70° C. for 2.5 h. A separate flask was charged with 19.3 g of CuCN and 540 mL of anhydrous ethyl ether under a nitrogen atmosphere. The mixture was cooled to −70° C. and 134 mL of a 1.6 M solution of MeLi in ethyl ether was added to it slowly. The cooling bath was removed and the mixture was allowed to warm up to −15° C., at which temperature it was stirred for an additional 45 minutes. The mixture was then cooled down to −70° C. and combined with the first solution (vinyllithium reagent) under nitrogen. The resulting mixture was warmed up to −40° C. and stirred at this temperature for 45 minutes. It was then cooled down to −70° C. and a solution of 46 g of compound (I') in 150 mL of anhydrous ethyl ether was added dropwise. Reaction was stirred at −70° C. for 2 h. The cooling bath was removed and the reaction was quenched with a saturated $NH_4Cl$ solution. It was then allowed to warm up to −10° C. at which temperature it was stirred for ~2 h. The reaction mixture was filtered through Celite and transferred to separatory funnel. The layers were separated, and the organic layer was dried over sodium sulfate, filtered and concentrated under vacuum. The crude product was purified via column chromatography on Silica gel to yield 80 g of compound (II-2) as a pale yellow solid.

Example 8. Preparation of Compound (IV-2) from Compound (II-2)

A reaction flask was charged with 10 g of compound (II-2) and 40 ml of anhydrous toluene. Argon was bubbled through the solution and reaction mixture was heated to 70° C. 50 mg of tricyclohexylphosphine[1,3-bis(2,4,6-trimethylphenyl) imidazol-2-ylidene][3-phenyl-1H-inden-1-ylidene]ruthenium(II) dichloride was added and reaction was stirred at 70° C. over 12 h. The reaction was treated with 1 mL of ethyl vinyl ether and stirred for 30 minutes. It was then concentrated and the crude product purified via column chromatography on Silica gel to yield 9 g of compound (IV-2) as an off-white solid.

Example 9. Preparation of Compound (V-2)

A reaction flask was charged with 23 mL of a 1M solution of $BH_3$-THF complex and 23 mL of a 1M solution of (R)—CBS in toluene. The mixture was stirred at ambient temperature for 10 minutes and cooled down to −70° C. A solution of 9 g of compound (IV-2) in 18 mL of anhydrous THF was added slowly to the reaction mixture maintaining the temperature below −70° C. during the course of the addition. The reaction was quenched with 10 ml of MeOH and allowed to warm up to −15° C. It was then treated with 30 ml of water and extracted with MTBE. The layers were separated and the organic phase was washed with 30 ml of 0.5N HCl, dried over sodium sulfate, filtered, and concentrated to afford 8.5 of compound (V-2).

Example 10. Preparation of Compound (IV-2) from Compound (III')

A reaction flask was charged with 40.5 g of 21 and 100 mL of anhydrous diethyl ether. It was then cooled to −78° C. and a solution of 2.5 M n-butyllithium in hexane (42.1 mL) was added to it. The mixture was stirred at −70° C. for 2 h. A separate flask was charged at room temperature with 18.5 mL of CuCN.2LiCl solution and 100 ml of ether. The suspension was cooled to −78° C. and 65.7 mL of 1.6 M methyllithium in THF was added slowly over 10 min, maintaining the temperature <−60° C. The mixture was allowed to warm to −15° C. while stirring for 30 min, giving a clear cuprate solution. The cuprate solution was then cooled to −78° C. and the vinyllithium solution, prepared above added via cannula. The resulting solution was allowed to warm to −40° C., stirred for 30 min at −40° C. and then cooled again to −78° C. To this solution was added 13.8 g of IRX-3 (i.e., compound (III')) slowly over 10-15 minutes. The resulting mixture was stirred at −70° C. for 2 h before it was quenched by a slow addition of 150 mL of saturated ammonium chloride. The cooling bath was removed and the reaction mixture warmed to room temperature and filtered through celite. The cake was washed with 30 ml MTBE and the layers were separated. The organic layer was washed with 100 mL of brine, dried over sodium sulfate, filtered and concentrated under reduced pressure. The crude product was purified by column chromatography (silica gel, 0-20% ethyl acetate/hexanes) to afford 16.7 g of compound (IV-2) as light yellow oil.

Example 11. Preparation of Compound (V-2)—(Alternative)

A reaction flask was purged with nitrogen and charged with 23 mL of $BH_3.SMe_2$ complex and 8.3 mL of R-methyl oxazaborolidine (1.0 M in toluene). The mixture were stirred at ambient temperature for at least 10 minutes then cooled to −70° C. A solution of 10.6 g of compound (IV-2) in 60 mL of anhydrous tetrahydrofuran was added to the mixture over at least 60 minutes, maintaining the temperature <−20° C. The mixture was stirred at −20° C. for at least 18 h. The mixture was cooled to −70° C. and quenched with 3 mL of MeOH. The mixture was diluted with 25 mL of hexanes and warmed to −20° C. Water (50 mL) was added to it slowly (exothermic with bubbling) and the mixture stirred at room temperature for 30 minutes. The organic phase was separated and washed with 50 mL of 0.5 N HCl followed by 50 mL of satd. aqueous sodium bicarbonate solution and brine (5 vol). The organic layer was dried over anhydrous $MgSO_4$, filtered and concentrated under reduced pressure. The crude was purified by column chromatography (silica gel, 0-20% ethyl acetate/hexanes) to afford 6.6 g of compound (V-2) as light yellow oil.

Example 12. Preparation of Compound (VI-2)

A reaction flask was purged with nitrogen and charged with 0.31 g of 4-dimethylaminopyridine, 2.06 g of 5-heptenoic acid, 2.4 mL of N,N'-diisopropylcarbodiimide (DIC), 6.6 g of compound (V-2) and 20 mL of anhydrous tetrahydrofuran. The mixture was heated to 40° C. and stirred for 21 hours. The reaction mixture was diluted with 66 mL of MTBE and washed with 50 mL of water. The aqueous layer was back-extracted with 30 mL of MTBE. The combined organic layer was washed with 30 mL of aqueous sodium bicarbonate followed by 30 mL of brine, dried over $MgSO_4$, and concentrated under reduced pressure. The crude product was purified by column chromatography (silica gel, 0-20% ethyl acetate/hexanes) to afford 5.9 g of compound (VI-2) as light yellow oil.

Example 13. Preparation of Compound (VII-2)

A reaction flask was charged with 0.5 g of compound (VI-2) and 30 ml of anhydrous DCM. Argon was bubbled through the solution and 50 mg of tricyclohexylphosphine [1,3-bis(2,4,6-trimethylphenyl)imidazol-2-ylidene][3-phenyl-1H-inden-1-ylidene]ruthenium(II) dichloride, was added and the reaction was stirred at 40° C. for 18 h. The reaction mixture was quenched with 2 mL of ethylamine (2M in THF) and stirred for 1 hour. The reaction mixture was diluted with MTBE and washed with aqueous sodium bicarbonate. The organic layer was separated and the aqueous layer back extracted with MTBE. The combined organic layers were washed with aqueous sodium bicarbonate, brine, dried over $MgSO_4$, filtered and concentrated under reduced pressure. The crude product was purified by column chromatography (silica gel, 0-10% ethyl acetate/hexanes) to afford 0.41 g of compound (VII-2) as light yellow oil.

Example 14. Preparation of Compound (IV-3)

A reaction flask was charged under nitrogen with 17.79 g of the vinyl iodide compound (3I) and 30 mL of anhydrous MTBE. The reaction flask was cooled to −78° C. and 15.12 mL of 2.5M n-butyl lithium in hexane was added to it. The mixture was allowed to stir at −70° C. for 2 h. A separate flask was charged at room temperature with CuCN.2LiCl solution (6.6 ml, 37.66 mmol) and 20 mL of MTBE. The suspension was cooled to −78° C. and 23.6 ml of 1.5M methyl lithium solution added slowly over 10 min maintaining temperature below −50° C. The mixture was allowed to warm to −15° C. and kept stirring at −5° C. to −10° C. for 30 min, giving a clear cuprate solution. The cuprate solution was then cooled to −78° C. and the vinyl lithium solution prepared earlier added slowly. The resulting yellow solution was allowed to warm to −40° C., stirred for 45 min at −40° C. to −30° C. and then cooled again to −78° C., followed by a slow addition of 6 g of compound (III'). The resulting mixture was stirred for 16 hours. The reaction was quenched by a slow addition of 100 mL of saturated $NH_4Cl$. Then cooling was removed, the reaction mixture warmed to RT and filtered through Celite. The cake was washed with 30 ml MTBE and 30 ml hexane and the layers were separated. The organic layer was washed with 30 mL of brine, dried over sodium sulfate, filtered and concentrated. The crude product was purified by column chromatography on silica using 0-5% EtOAc/hexane. The pure fractions were combined and concentrated to afford 24.5 g product IV-3 as pale yellow oil.

Example 15. Preparation of Compound (V-3)

A reaction flask was charged with borane-dimethyl sulfide complex ($BH_3.SMe_2$) in toluene (1.4 ml) and R-methyl oxazaborolidine in toluene (2.54 ml). The mixture was stirred at room temperature for 15 minutes then cooled to −70° C. In a separate flask compound (IV-3) (1.48 g) was dissolved in THF (15 ml) and added to the mixture containing the borane reagents over 60 minutes maintaining the temperature <−50° C. The mixture was stirred at −50° C. for 1 h, warmed to −20° C. slowly and kept at −20° C. for 48 hours. The reaction mixture was quenched with water (20 ml) keeping the temperature <10° C. The mixture was treated with 0.5 N HCl (15 ml) for 30 minute then extracted with a mixture MTBE (30 ml) and hexane (20 ml). The organic layer was washed with bicarbonate solution (15 ml), brine (15 mL), dried over magnesium sulfate and concentrated under reduced pressure. The crude product was purified by silica column chromatography using 10-30% EtOAc/hexanes to afford 1.2 g of compound (V-3) as clear oil.

Example 16. Preparation of Compound (II-5)

A reaction flask was charged at ambient temperature with 200 g of compound (I') in 700 mL of nitromethane. The reaction flask was cooled to −10° C. to 0° C. and while stirring 9.5 g of 1,1,3,3 tetramethyl guanidine was added. The mixture was allowed to stir at −10° C. to 0° C. for 6 hrs. The mixture was acidified to pH 4 with 10 ml of acetic acid and concentrated to remove nitromethane. Then, 1 L of MTBE and 1 L of 0.5 N HCl was added and the layers were separated. The organic layer was washed with a 500 mL of saturate sodium bicarbonate, 200 mL of brine, dried over sodium sulfate, filtered, concentrated, and purified by column chromatography to obtain 156 g of compound (11-5).

Example 17. Preparation of Compound (V-5A)

A reaction flask was charged with 535 mL of BH3-THF complex (1.0M in THF), 535 mL of R—CBS (1.0M in Toluene), and (R)-Methyl oxazaborolidine in toluene. The reaction mixture was stirred at ambient temperature for 10 minutes and then cooled to −75° C. A solution of 151 g of compound (11-5) in 300 mL of THF was added maintaining <−70° C. and the reaction was stirred for at least 1 h at −75° C. The reaction was quenched with methanol maintaining <−70° C. The contents were warmed up to −15° C. and diluted with 450 mL water and extracted with 600 mL of MTBE. The MTBE layer was separated and aqueous layer re-extracted with 600 mL of MTBE. The combined organic layers were washed sequentially with 500 mL of 0.5 N HCl and brine, dried over sodium sulfate, filtered, concentrated, and purified by column chromatography to afford 120 g of compound (V-5A).

Example 18. Preparation of Compound (VI-5A)

A reaction flask was charged at ambient temperature with 90 g of compound (V-5A), 51.2 mL of 5-hexenoic acid, 66.7 mL of 1, 3-diisopropyl carbodiimide and 7 g of DMAP. The mixture was stirred for 8 h at ambient temperature, The mixture was then filtered, and the filtrates were concentrated and purified by column chromatography to afford 89.2 g of compound (VI-5A).

Example 19. Preparation of Compound (VII-5)

A reaction flask was charged with 85 g of compound (VI-5A) and 8.5 L of toluene at ambient temperature under an atmosphere of argon. The mixture was purged with argon for 30 min and 425 mg of tricyclohexylphosphine[1,3-bis(2,4,6-trimethylphenyl)imidazol-2-ylidene][3-phenyl-1H- inden-1-ylidene]-ruthenium(II) dichloride, was added to it. It was then heated at 75° C. for 1.5 h. The mixture was quenched with ethyl vinyl ether, concentrated to dryness, and purified by column chromatography to afford 49.1 g of compound (VII-5).

Example 20. Preparation of Compound (VIII-5)

A reaction flask was charged with 48 g of compound (VII-5), 480 mL of methanol and 17.8 g of $NH_4HF_2$ at ambient temperature under an atmosphere of nitrogen. The reaction mixture was heated to reflux for 4 hours. The reaction mixture was cooled to ambient temperature and concentrated to dryness. The residue was triturated with DCM for 30 min and filtered. The filtrates were concentrated and purified by column chromatography to afford 25.2 g of compound (VIII-5).

Example 21. Preparation of Compound (VIII-5A')

A reaction flask was charged with 175 g of $NH_4OAc$ and 481 g of $TiCl_3$ (12%) in 850 mL of water. A solution of 25 g of compound (VIII-5) in 625 mL of THF was slowly added to the reaction mixture over one hour. The reaction mixture was stirred for 3 hours. It was then diluted with 1 L of water and extracted twice with 2 L of ethyl acetate. The organic layers were combined, dried, filtered, concentrated and purified by column chromatography to afford 141 g of compound (VIII-5A').

Example 22. Preparation of Compound (II-6A)

As reaction flask was charged with 778 mL of vinyl magnesium bromide (1 M in THF) and 560 mL of anhydrous THF under nitrogen and cooled to −25° C. The, 71 g (778 mmol) of CuCN was added in one portion into reaction mixture. The mixture was stirred at −25 to −20° C. over at least 1 hour. The reaction contents were cooled to −70 to −75° C. and 56 g (223 mmol) of cyclopentenone (I') was added slowly maintaining <−70° C. Removed cooling bath and allowed to warm to −50 to −55° C. and was stirred for 2.5 h, TLC indicated complete reaction. The reaction mixture was quenched with 300 mL of aqueous ammonium chloride maintaining <−30° C., warmed to 0-5° C. and filtered through Celite. The mixture was diluted with 1 L of MTBE layers were separated. The organics were washed with 100 mL of brine, dried over sodium sulfate filtered, concentrated and purified by column chromatography to afford 61 g of the vinyl cyclopentanone (II-6A).

Example 23. Preparation of Compound (V-6A)

A reaction flask was charged under nitrogen with 235 mL of BH3-THF complex (1.0M in THF) and 235 mL of R—CBS (1.0M in Toluene), and (R)-Methyl oxazaborolidine in toluene. The contents were stirred at ambient temperature for 10 minutes and then cooled to −75° C. A mixture of 60 g (214 mmol) of vinyl cyclopentanone (II-6A) and 120 mL of THF was added maintaining <−70° C. The mixture was stirred for at least 1 h at −75° C. The mixture was quenched with methanol maintaining <−70° C. The contents were warmed to −15° C. and diluted with 200 mL water, 400 mL of MTBE. The MTBE layer was separated and aqueous layer re-extracted with 600 mL of MTBE. The combined organics were washed with 100 mL of 0.5 N HCl, brine, dried over sodium sulfate, filtered, concentrated and purified by column chromatography to afford 46 g of compound (V-6A).

Example 24. Preparation of Compound (VI-6A)

A reaction flask was charged at room temperature under nitrogen with 45 g of alcohol (V-6A), 28.2 mL of 5-Hexenoic acid, 37 mL, of 1,3-diisopropyl carbodiimide and 3.9 g of DMAP. The mixture was stirred for 8 h at ambient temperature. The mixture was then filtered, and filtrates were concentrated and purified by column chromatography to afford 49.5 g compound (VI-6A).

Example 25. Preparation of Compound (VII-6')

A 12 L 3N RBF was equipped with mechanical agitation, condenser, TC control, heating mantle, and Argon blanket. At room temperature 49 g (129 mmol) of ester (VI-6A) and 5 L of toluene was added. The mixture was purged with argon for 30 min, 245 mg of tricyclohexylphosphine[1,3-bis(2,4,6-trimethylphenyl)imidazol-2-ylidene][3-phenyl-1H-inden-1-ylidene]ruthenium(II) dichloride was added and heated to 75° C. while maintaining argon purge. The mixture was stirred for at least 1.5 h at 75° C. The mixture was quenched with ethyl vinyl ether. The contents were concentrated to dryness and purified by column chromatography to afford 31.3 g of the protected lactone compound (VII-6').

Example 26. Preparation of Compound (VIII-6')

A reaction flask was charged at room temperature under nitrogen with 31 g of compound (VII-6'), 310 mL of methanol and 7.6 g of $NH_4HF_2$. The mixture was heated to reflux for at least 4 hours, cooled to ambient temperature, and concentrated to dryness. The residue was triturated with DCM for 30 min and filtered. The filtrates were concentrated and purified by column chromatography to afford 20 g of the lactone compound (VIII-6').

Example 27. Preparation of Compound (VIII-7)

A reaction flask was charged at ambient temperature with 4.7 g of NaH (60%) and 1 L of THF. To this mixture was added a solution of 33.6 g of diethyl 3,3-difluoro-2-oxohexylphosphonate in 200 mL of THF. The reaction mixture was stirred under nitrogen for a few minutes and a solution of 14 g of compound (VIII-5A') in 200 mL of THF was added slowly to it over a period of 30 minutes. The mixture was heated to 60° C. for 2 days until the starting material had been consumed. The mixture was cooled to ambient temperature and treated with a solution of 200 mL of saturated $NH_4Cl$ followed by 200 mL of water. The mixture was extracted twice with 400 mL of ethyl acetate. The organic layers were combined, dried, filtered, concentrated and purified by column chromatography to afford 10.4 g of compound (VIII-7).

Example 28. Preparation of Compound (VII-7B)

A reaction flask was charged at ambient temperature under nitrogen with 10 g of compound (VIII-7) and in 50 mL of THF. The solution was cooled to 0° C. and 3.9 mL of ethyl vinyl ether was added to it followed by 5 mg of pTSA. The mixture was stirred at 0° C. for 2 hours. The reaction was then treated with a solution of 200 mL of saturated $NH_4Cl$ followed by 200 mL of water. The organic phase was concentrated after adding 1 mL triethylamine to it and purified by column chromatography to afford 10.1 g of compound (VII-7B).

Example 29. Preparation of Compound (VII-7C)

A hydrogenation vessel was charged at ambient temperature under nitrogen with 4.8 g of compound (VII-7B), 250 mL of IPA, and 2.5 g of 10% Pd/C. The reactor was pressurized with hydrogen to 50 psi and the reaction mixture was stirred for 2 hours, It was then filtered through Celite, concentrated, and purified by column chromatography to afford 4.2 g of compound (VII-7C).

Example 30. Preparation of Compound (VII-7D)

A reaction flask was charged at ambient temperature under nitrogen with 10 mL of BH3-THF complex (1.0M in THF) and 10 mL of (R)-Methyl oxazaborolidine (R—CBS) (1.0M in Toluene). The reaction was stirred at ambient temperature for 10 minutes and then cooled to −75° C. A solution of 4 g of compound (VII-7C) in 8 mL of THF was added to it maintaining the temperature at <−70° C. The reaction was then stirred at −75° C. until completion (~1 hour). It was then quenched with methanol maintaining the temperature at <−70° C. The mixture was allowed to warm up to −15° C. and diluted with 10 mL water and 15 mL of MTBE. The MTBE layer was separated and the aqueous layer re-extracted with 15 mL of MTBE. The combined organic layers were washed with 10 mL of 0.5 N HCl, brine, dried over sodium sulfate, filtered, concentrated and purified by column chromatography to afford 3.4 g of compound (VII-7D).

Example 31. Preparation of Compound (LUB-1)

A reaction flask was charged at ambient temperature under nitrogen with 3.4 g of compound (VII-7D), 0.96 g of LiOH, 40 mL of THF, and 1 mL of water. The reaction was stirred at 55° C. for 24 hours. The reaction mixture was cooled to 0° C. and acidified to pH 6-7 with 1 N HCl. It was then extracted with 50 mL of MTBE. The MTBE layer was separated and the aqueous layer re-extracted with 15 mL of MTBE. The combined organic layers were washed with 20 mL of brine, dried over sodium sulfate, filtered, concentrated, and purified by column chromatography to afford 3.3 g compound (LUB-1).

Example 32. Preparation of Compound (LUB-2)

A reaction flask was charged at ambient temperature under nitrogen with 3.3 g of compound (LUB-1), 20 mL of THF, 2.1 g of DBU, and 1.7 mL of benzyl bromided. The reaction solution stirred at ambient temperature for 5 hours. It was then cooled to 0° C. and diluted with 50 mL of MTBE and 50 mL of saturated aqueous sodium bicarbonate. The MTBE layer was separated and the aqueous layer re-extracted with 15 mL of MTBE. The combined organic layers were washed with 20 mL of brine, dried over sodium sulfate, filtered, concentrated and purified by column chromatography to afford 3.2 g of compound (LUB-2).

Example 33. Preparation of Compound (LUB-3)

A reaction flask was charged at ambient temperature under nitrogen with 3 g of compound (LUB-2), 20 mL of toluene, 20 mL of DMSO, and 10 g 2-iodobenzoic acid (IBX). The reaction mixture was stirred for at least 4 h at 50° C. It was then cooled to ambient temperature, and filtered. The filter cake was washed with 40 mL MTBE. The combined organic layers were washed successively with 20 mL of aqueous sodium bicarbonate, 20 mL of aqueous sodium sulfite, and 20 mL of brine. They were then dried over sodium sulfate, filtered, and concentrated. The crude product was purified by column chromatography to afford 2.5 g of the compound (LUB-3).

Example 34. Preparation of Lubiprostone Benzyl Ester (LUB-4)

A reaction flask was charged at ambient temperature under nitrogen with 2.5 g of lubiprostone benzyl ester (LUB-3), 15 mL of THF, 15 mL of water, and 45 mL acetic acid. The mixture was heated at 40° C. until the starting material had been consumed (at least 4 hours). It was then cooled to ambient temperature and filtered. The filter was washed with 50 mL MTBE. The organic layer was washed successively with 20 mL of aqueous sodium bicarbonate and 20 mL of brine. It was dried over anhydrous sodium sulfate, filtered, concentrated, and purified by column chromatography to afford 1.8 g of lubiprostone benzyl ester (LUB-4).

Example 35. Preparation of Compound (X')

A reaction flask was charged at ambient temperature under nitrogen with 38 g of compound (I'), and 92.6 g of benzyl-5-hexonate and 300 mL of toluene was added. The mixture was purged with argon for 30 min, 500 mg of tricyclohexylphosphine[1,3-bis(2,4,6-trimethylphenyl)imidazol-2-ylidene][3-phenyl-1H-inden-1-ylidene]ruthenium (II) dichloride was added and heated to 75° C. while maintaining argon purge. The mixture was stirred for at least 10 h at 75° C. and quenched with ethyl vinyl ether. The contents were concentrated to dryness and purified by column chromatography to afford 40 g of compound (X').

Example 36. Preparation of Compound (LUB-5)

A reaction flask was charged under nitrogen with 26.6 g of compound (7I) and 100 mL of anhydrous ether. It was then cooled to −70 to −75° C. and 29 mL of n-BuLi (2.5M in hexane) was added slowly maintaining <−65° C. The reaction mixture was cooled to <−70° C. and stirred at −75 to −70° C. for at least 2.5 h. In a separate flask was added 6.7 g of CuCN, 150 mL anhydrous ether and cooled to −70 to −75° C. Then 45 mL of methyl lithium (1.6M in diethylether) was added slowly maintaining <−65° C. The mixture was allowed to warm to −15° C. while stirred for 30 min giving clear solution. The reaction mixture was cooled to <−70° C. and the previously prepared vinyl lithium reagent was added slowly via cannula maintaining <−65° C. The mixture was allowed to warm to −40° C., stirred for 45 min at −40° C. and then cooled again to −78° C. The reaction was allowed to stir at −60 to −65° C. for 2.5 hours. The reaction mixture was cooled to <−65° C. quenched with 29 mL of ammonium chloride maintaining <−30° C., warmed to 0-5° C., and filtered through Celite. The cake was washed with 29 mL of MTBE. The layers were separated and the organic layer was washed with 29 mL of brine, dried over sodium sulfate, filtered, concentrated and purified by column chromatography to afford 25.5 g of compound (LUB-5).

Example 37. Preparation of Compound (LUB-6)

At room temperature 5 g of (LUB-5) in 50 mL of THF was charged to a hydrogenation vessel and 1 g (1.0 mmol) of 10% Pd/C was added. The reactor was pressurized to 50 psi and mixture was stirred for 2 hours. The mixture was filtered through Celite, concentrated and purified by column chromatography to afford 3 g of compound (LUB-6).

Example 38. Preparation of Compound (LUB-2A)

A reaction flask was charged under nitrogen with 3 g compound (LUB-6), 15 mL of DMF, 2.5 g sodium bicarbonate, 0.8 g potassium carbonate and 1.4 mL of benzyl bromide. The contents were stirred at 30° C. room temperature for 3 hours. The mixture was cooled to room temperature and the solids were filtered. The filtrates were diluted with 100 mL of MTBE and extracted with 50 mL of brine. The organic layer was separated and the aqueous layer re-extracted with 15 mL of MTBE. The combined organic layers were dried over sodium sulfate, filtered, concentrated and purified by column chromatography to afford 2.7 g compound (LUB-2A).

Example 39. Preparation of Compound (LUB-3A)

A reaction flask was charged under nitrogen at ambient temperature with 2.7 g compound (LUB-2A), 20 mL of toluene, 20 mL of DMSO, and 10 g of SIBX. The mixture was heated to 50° C. and was stirred for at least 4 hours. The mixture was cooled to room temperature and filtered. The cake was washed with 40 mL MTBE. The mixture was washed with 20 mL of aqueous sodium bicarbonate and 20 mL of sodium sulfite, 20 mL of brine, dried over sodium sulfate, filtered, concentrated and purified by column chromatography to afford 2.3 g of compound (LUB-3A).

Example 40. Preparation of Compound (LUB-4) from (LUB-3A)

A reaction flask was charged under nitrogen at ambient temperature with 2.3 g of compound (LUB-3A), 23 mL of acetonitrile, and 2.3 g of trifluro acetic acid. The mixture was heated to 40° C. for at least 4 hours. The mixture was cooled to room temperature, diluted with 50 mL MTBE, and extracted with 25 mL of water. The organic layer was washed with 20 mL of aqueous sodium bicarbonate and 20 mL of brine, dried over sodium sulfate, filtered, concentrated, and purified by column chromatography to afford 1.3 g of compound (LUB-4).

Example 41. Preparation of Compound (IV-8)

A reaction flask was charged 60 mL of anhydrous ethyl ether and 26 mL of t-BuLi (1.6M in Pentane) at <−65° C. under nitrogen. The resulting solution was then cooled to <−70° C. and the alkyl iodide (8I) was charged slowly maintaining the temperature <−65° C. The reaction mixture was stirred at −75 to −70° C. for at least 2 h and 2 g of CuCN was added to it in one portion. The reaction was allowed to gradually warm up to −25 to −20° C. and stirred at this temperature for one hour. The reaction was cooled to −70 to −75° C. again and 2 g of compound (III-A) was added slowly maintaining the temperature <−70° C. When the addition was complete, the cooling bath was removed and the reaction allowed to warm up to −60 to −65° C. at which temperature it was stirred for 0.5 h. The mixture was then quenched with 40 mL of ammonium chloride maintaining the temperature <−30° C., allowed to warm up to 0-5° C., and was filtered through Celite. The mixture was diluted with 25 mL of MTBE, the layers were separated, and the organic layer washed with 20 mL of brine, dried over sodium sulfate, filtered, and concentrated under vacuum. The crude product was purified by column chromatography to afford 5.9 g of compound (IV-8).

Example 42. Preparation of Compound (V-8)

A reaction flask was charged with 11.6 mL of BH3-THF complex (1.0M in THF) and 11.6 mL of R—CBS (1.0M in Toluene). The contents were stirred at ambient temperature for 10 minutes and then cooled to −75° C. A solution of 2.6 g of compound (IV-8) in 10 mL of THF was added maintaining the temperature <−70° C. The mixture was stirred for at least 1 h at −75° C., quenched with methanol maintaining at <−70° C., and allowed to warm up to −15° C. It was then diluted with 15 mL of water, and extracted with 30 mL of MTBE. The MTBE layer was removed and the aqueous layer re-extracted with 30 mL of MTBE. The combined organic layers were successively washed with 25 mL of 0.5 N HCl and brine. They were then dried over sodium sulfate, filtered, and concentrated under vacuum. The crude product was purified by column chromatography to afford 4.3 g of compound (V-8).

Example 43. Preparation of Compound (VI-8)

A reaction flask was charged with 2.1 g of compound (V-8), 1.6 mL of 5-hexenoic acid, 2 mL of 1,3-diisopropylcarbodiimide, and 0.2 g of DMAP. The mixture was stirred at ambient temperature for 8 hours. The reaction mixture was filtered, and filtrates were concentrated under vacuum. The crude product was purified by column chromatography to afford 4.6 g compound (VI-8).

Example 44. Preparation of Compound (VII-8)

A reaction flask was charged under an atmosphere of argon with 4.5 g of compound (VI-8), 450 mL of toluene, and 22.5 mg of tricyclohexylphosphine[1,3-bis(2,4,6-trimethylphenyl)imidazol-2-ylidene][3-phenyl-1H-inden-1-ylidene]ruthenium(II) dichloride. The reaction was stirred at 75° C. for at least 1 hour. The reaction was quenched with ethyl vinyl ether and concentrated under vacuum. The crude product was purified by column chromatography to afford 3.1 g of compound (VII-8).

Example 45. Preparation of Compound (VIII-8)

A reaction flask was charged with 3 g of compound (VII-8), 25 mL of THF, and 6.5 mL of 1.0 M TBAF. The reaction was stirred at 40° C. for at least 4 hours, cooled to ambient temperature, diluted with 20 mL of MTBE, and extracted with 15 mL of aqueous sodium bicarbonate. The layers were separated and the organic phase was washed with 20 mL of brine, dried over sodium sulfate, filtered, and concentrated under vacuum. The crude product was purified by column chromatography to afford 1.9 g of compound (VIII-8).

Example 46. Preparation of Compound (UNO-2)

A reaction flask was charged with 1.3 g of compound (VIII-8), 8 mL of toluene, 8 mL of DMSO, and 1 g of 2-iodobenzoic acid (IBX). The reaction was stirred at 50° C. for at least 4 hours. The reaction mixture was cooled to ambient temperature and filtered. The filter cake was washed with 8 mL MTBE. The combined organic layers were washed successively with 6 mL of aqueous sodium bicarbonate, 6 mL of NaSO$_3$, 8 mL of brine. They were subsequently dried over sodium sulfate, filtered, and concentrated under vacuum. The crude product was purified by column chromatography to afford 1.2 g of compound (UNO-2).

Example 47. Preparation of Unoprostone Isopropyl Ester

A reaction flask was charged with 1.0 g of compound (UNO-2), 5 mL of IPA, and 2 drops of sulfuric acid. The reaction mixture was stirred at 75° C. for at least 24 hours. The reaction mixture was then cooled to ambient temperature, and diluted with 6 mL MTBE and 5 mL of aqueous sodium bicarbonate. The layers were separated and the organic layer was washed with brine, dried over sodium sulfate, filtered, and concentrated under vacuum. The crude product was purified by column chromatography to afford 0.6 g of Unoprostone isopropyl ester.

Example 48. Preparation of Compound (XIV-6)

A reaction flask was charged under nitrogen with 20 g of the lactone compound (VIII-6), 13.5 g of NaOH in 60 mL of water, and 200 mL of methanol. The contents were stirred at 50° for 7 hours, cooled to 30° C., and concentrated. The residue was diluted with 100 mL of MTBE, 100 mL water, and acidified with 12 N HCl to pH 2. The MTBE layer was separated and aqueous layer re-extracted with 40 mL of MTBE. The combined organic layers were washed with 20 mL of brine, dried over sodium sulfate, filtered, concentrated and purified by column chromatography to afford 17.6 g of compound (XIV-6).

Example 49. Preparation of Compound (XIV-6A)

A reaction flask was charged under nitrogen with 17 g of compound (XIV-6), 100 mL of DMF, 27.7 g of K$_2$CO$_3$, and 34 g of 2-iodo propane. The contents were stirred at 20° C. for 12 hours. The mixture was diluted with 100 mL of MTBE and 100 mL water. The MTBE layer was separated and aqueous layer re-extracted with 40 mL of MTBE. The combined organic layers were washed with 50 mL of brine, dried over sodium sulfate, filtered, concentrated and purified by column chromatography to afford 16.8 g compound (XIV-6A).

Example 50. Preparation of Compound (UNO-1)

A reaction flask was charged under nitrogen at ambient temperature with 16.8 g compound (XIV-6A), 17.4 g heptyl vinyl ketone, and 60 mL of toluene. The mixture was purged with argon for 30 minutes before 170 mg of tricyclohexylphosphine[1,3-bis(2,4,6-trimethylphenyl)imidazol-2-ylidene][3-phenyl-1H-inden-1-ylidene]ruthenium(II) dichloride was added to it. The reaction solution was heated to 75° C. for 10 hours under argon. It was then quenched with ethyl vinyl ether. The solution was concentrated to dryness and purified by column chromatography to afford 5.6 g compound (UNO-1).

Example 51. Preparation of Compound (XIV-6')

A reaction flask was charged at ambient temperature under nitrogen with 3 g of the lactone (VII-6"), 1.8 g of LiOH, 40 mL of THF, and 3 mL of water was added. The reaction was stirred at 55° for 24 hours. It was then cooled to 0° C. and acidified to pH 6-7 with 1 N HCl. The contents were extracted with 50 mL of MTBE. The MTBE layer was separated and aqueous layer re-extracted with 15 mL of MTBE. The combined organic layers were washed with 20 mL of brine, dried over Na$_2$SO$_4$, filtered, concentrated and purified by column chromatography to afford 2.6 g of the acid (XIV-6').

Example 52. Preparation of Compound (XV')

A reaction flask was charged at ambient temperature under nitrogen with 2.4 g of the acid (XIV-6'), 2.1 g of the 4,4-difluoro-oct-1-en-3-ol and 3.5 mL of N-methyl morpholine in 40 mL of THF. The mixture was cooled to 0° C. and 1.6 mL of pivaloyl chloride was added. The contents were stirred at 20° for 24 hours. The mixture was cooled to 0° C. and diluted with NH$_4$Cl and MTBE. The MTBE layer was separated and the aqueous layer re-extracted with 15 mL of MTBE. The combined organic layers were washed with 20 mL of brine, dried over Na$_2$SO$_4$, filtered, concentrated, and purified by column chromatography to afford 2.2 g of the ester (XV').

Example 53. Preparation of Compound (XVI')

A reaction flask was charged at ambient temperature under nitrogen with 2 g of the ester (XV') and 200 mL of toluene. It was then purged with argon for 30 min, and 20 mg of the "Ru" catalyst was added. The reaction was heated to 75° C. while maintaining argon purge and stirred at that temperature for at least 1.5 hours. It was then quenched with ethyl vinyl ether and concentrated to dryness. The crude product was purified by column chromatography to afford 1.2 g of the macrocyclic lactone (XVI').

Example 54. Preparation of Compound (XVI'-A)

A hydrogenation flask was charged at ambient temperature with 1.1 g of the macrocyclic lactone (XVI') in 20 mL of IPA and 0.6 g of 10% Pd/C. The reactor was pressurized to 50 psi and mixture was stirred for 2 hours. The mixture was filtered through Celite, concentrated, and purified by column chromatography to afford 0.9 g of the saturated macrocyclic lactone (XVI'-A).

Example 55. Preparation of Compound (LUB-1A)

A reaction flask was charged at ambient temperature under a nitrogen blanket with 0.9 g of the saturated macrocyclic lactone (XVI'-A), 0.4 g of LiOH, 10 mL of THF, and 1 mL of water. The reaction was stirred at 55° for 24 hours. It was then cooled to 0° C. and acidified to pH 6-7 with 1 N HCl. The contents were extracted with 20 mL of MTBE. The MTBE layer was separated and the aqueous layer re-extracted with 15 mL of MTBE. The combined organic layers were washed with 10 mL of brine, dried over Na$_2$SO$_4$, filtered, concentrated and purified by column chromatography to afford 0.8 g of the acid (LUB-1A).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for preparing a synthetic intermediate of a prostaglandin or prostaglandin analog, the method comprising:

providing a compound of Formula (VI):

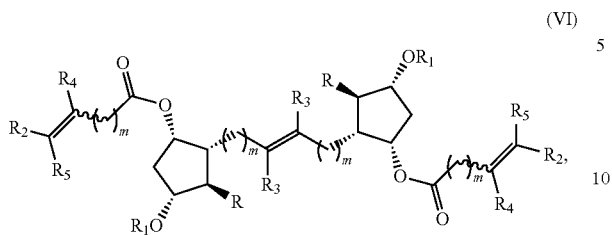

(VI)

wherein:
  each m and n are independently an integer between 0 and 10;
  each $R_1$ is independently H or a hydroxyl protecting group;
  each $R_2$, $R_3$, $R_4$, and $R_5$ is independently selected from the group consisting of H, alkyl, substituted alkyl, aralkyl, substituted aralkyl, aryl, and substituted aryl; and
  each R is selected from the group consisting of aldehyde, acyl, nitroalkyl, aminoalkyl, thioalkyl, vinyl, and alkyl or alkenyl of the formula:

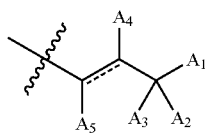

wherein:
  === represents a single or a double bond;
  $A_1$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino;
  $A_2$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, with the proviso that $A_2$ is not halogen or amino when $A_1$ or $A_3$ is hydroxyl or amino;
  $A_3$ is hydrogen, alkyl, substituted alkyl, cycloalkyl, substituted cycloalkyl, aryl, substituted aryl, aralkyl, substituted aralkyl, acyl, alkoxyl, aralkoxyl, substituted aralkoxyl, aryloxyl, thioalkyl, thioaralkyl, thioaryl, thiophenyl, benzothiophenyl, sulfonyl, sulfinyl, halogen, hydroxyl, protected hydroxyl, or amino, with the proviso that $A_3$ is not halogen or amino when $A_1$ or $A_2$ is hydroxyl or amino;
  or wherein two of $A_1$, $A_2$, and $A_3$ together form a ring or =O; and
  $A_4$ and $A_5$ are independently hydrogen, alkyl, substituted alkyl, cycloalkyl, substituted cycloalkyl, aryl, substituted aryl, aralkyl, substituted aralkyl, acyl, alkoxyl, or aralkoxyl; and
reacting the compound of Formula (VI) with a transition metal catalyst to perform a ring closing metathesis reaction to form a lactone, and optionally reducing a carbon-carbon double bond in the formed lactone via catalytic hydrogenation, thereby preparing a synthetic intermediate of a prostaglandin or prostaglandin analog, wherein the synthetic intermediate is a compound of Formula (VII):

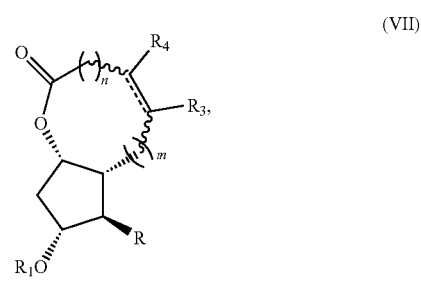

(VII)

wherein m, n, R, $R_1$, $R_3$, and $R_4$ are as defined for the compound of Formula (IV).

2. The method of claim 1, wherein the transition metal catalyst is a transition metal carbene complex catalyst.

3. The method of claim 1, wherein the transition metal catalyst is benzylidene-bis(tricyclohexylphosphine) dichlororuthenium.

4. The method of claim 1, wherein the lactone is a nine- or ten-membered lactone.

5. The method of claim 1, wherein $R_1$ is a hydroxyl protecting group.

6. The method of claim 1, further comprising opening the lactone ring of the compound of Formula (VII) via acid catalyzed hydrolysis and esterifying the resulting carboxylic acid, thereby converting the compound of Formula (VII) into a prostaglandin or prostaglandin analog of the formula:

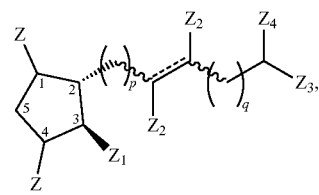

wherein:
  === represents a single or a double bond;
  each Z is independently hydroxyl or a protected hydroxyl;
  p and q are independently integers between 0 and 10;
  $Z_1$ is selected from the group consisting of aldehyde, ketone, nitroalkyl, aminoalkyl, thioalkyl, vinyl, and a substituted or unsubstituted alkyl or alkenyl;
  each $Z_2$ is independently selected from H and substituted or unsubstituted alkyl, aralkyl or aryl;
  $Z_3$ is selected from alkoxy, aryloxy, and aralkyloxy; and
  $Z_4$ is =O.

7. The method of claim 1, further comprising reacting the lactone ring of the compound of Formula (VII) with a nucleophile to form a ring-opened product, wherein the nucleophile is selected from the group consisting of water, an alcohol, a thiol, an amine, a sulfonamide, an imide, hydroxide, a hydroxide salt, an alkoxide, an alkoxide salt, a thiolate, and a thiolate salt, and wherein the ring-opened product is a prostaglandin or prostaglandin analog having a structure of the formula:

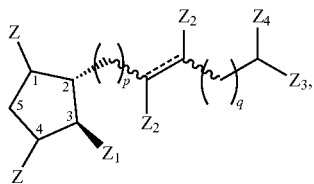

wherein:

=== represents a single or a double bond;
each Z is independently hydroxyl or a protected hydroxyl;
p and q are independently integers between 0 and 10;
$Z_1$ is aldehyde, ketone, nitroalkyl, aminoalkyl, thioalkyl, vinyl, or a substituted or unsubstituted alkyl or alkenyl;
each $Z_2$ is independently selected from H and substituted or unsubstituted alkyl, aralkyl or aryl;
$Z_3$ is selected from OH, SH, $NH_2$, alkoxy, aryloxy, aralkyloxy, thioalkyl, thioaralkyl, thioaryl, —NH-alkyl, —NH-aryl, —NH-aralkyl, —NH-sulfonyl-alkyl, —NH-sulfonyl-aryl, —N(alkyl)$_2$, —N(aryl)$_2$, and —N(alkyl)(aryl); and
$Z_4$ is =O.

8. The method of claim 7, wherein the nucleophile is selected from the group consisting of an amine, an alcohol, an alkoxide, an alkoxide salt, and hydroxide.

9. The method of claim 7, further comprising removing one or more hydroxyl protecting groups from the prostaglandin or prostaglandin analog.

10. The method of claim 1, wherein $R_1$ is a hydroxyl protecting group and the method further comprises removing one or more hydroxyl protecting groups from the compound of Formula (VII) to provide a compound of Formula (VIII):

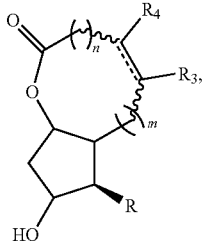

(VIII)

wherein n, m, R, $R_3$, and $R_4$ are as defined for the compounds of Formula (VII).

11. The method of claim 7, wherein Z at carbon 1 of the cyclopentane of the prostaglandin or prostaglandin analog is hydroxyl and Z at carbon 4 of the prostaglandin or prostaglandin analog is protected hydroxyl, and the method further comprises oxidizing the hydroxyl group at carbon 1 of the cyclopentane of the prostaglandin or prostaglandin analog to provide a prostaglandin or prostaglandin analog having a structure of the formula:

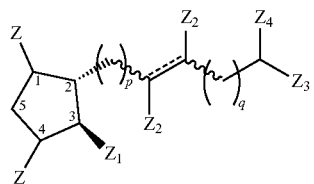

wherein:

=== represents a single or a double bond;
Z at carbon 1 of the cyclopentane ring is a =O;
Z at carbon 4 of the cyclopentane ring is protected hydroxyl;
p and q are independently integers between 0 and 10;
$Z_1$ is aldehyde, ketone, nitroalkyl, aminoalkyl, thioalkyl, vinyl, or a substituted or unsubstituted alkyl or alkenyl;
each $Z_2$ is independently selected from H and substituted or unsubstituted alkyl, aralkyl or aryl;
$Z_3$ is selected from OH, SH, $NH_2$, alkoxy, aryloxy, aralkyloxy, thioalkyl, thioaralkyl, thioaryl, —NH-alkyl, —NH-aryl, —NH-aralkyl, —NH-sulfonyl-alkyl, —NH-sulfonyl-aryl, —N(alkyl)$_2$, —N(aryl)$_2$, and —N(alkyl)(aryl); and
$Z_4$ is =O.

12. The method of claim 1, wherein the compound of Formula (VII) is a synthetic intermediate of a prostaglandin or prostaglandin analog selected from the group consisting of bimatoprost, latanoprost, travoprost, tafluprost, unoprostone, dinoprost, carboprost, fluprostenol, cloprostenol, 13,14-dihydro-15-(2-benzothienyl)-15-pentanor PGF1α, sulprostone, misoprostol, and limaprost.

13. The method of claim 1, wherein the compound of Formula (VI) is crystalline.

14. The method of claim 1, wherein the compound of Formula (VI) is provided by the esterification of a compound of Formula (V):

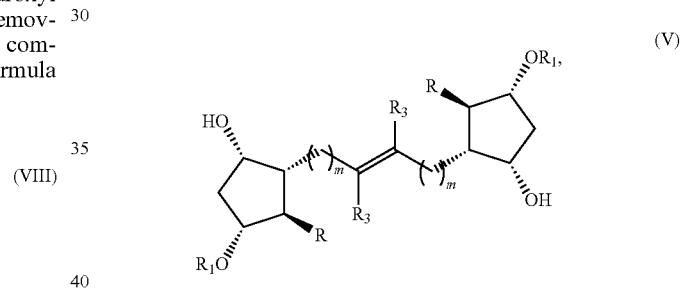

(V)

wherein m, R, $R_1$, and $R_3$ are as described for the compound of Formula (VI).

15. The method of claim 14, wherein the esterification is performed by contacting the compound of Formula (V) with an alkenoic acid or acid chloride, or a derivative thereof, wherein the derivative thereof is an alkenoic acid or acid chloride comprising one or more alkyl group substituents.

16. The method of claim 15, wherein the compound of Formula (V) is the product of the enantioselective reduction of carbonyl groups of a compound of Formula (IV):

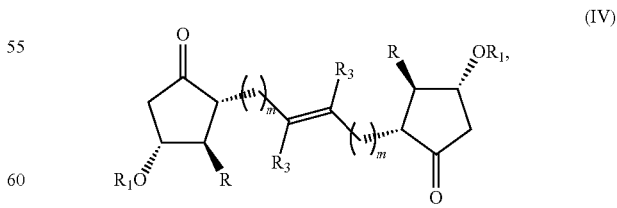

(IV)

wherein m, R, $R_1$, and $R_3$ are as described for the compound of Formula (VI).

17. The method of claim 16, wherein the compound of Formula (IV) is the product of a stereoselective 1,4-double addition of a nucleophile to a compound of Formula (III):

(III)

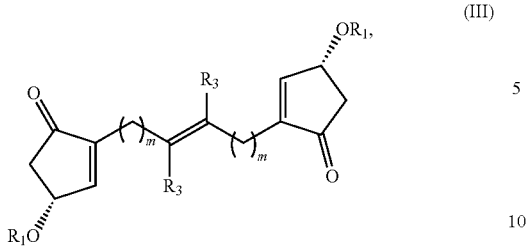

wherein m, $R_1$, and $R_3$ are as defined for the compound of Formula (VI).

18. The method of claim 17, wherein the nucleophile is selected from the group consisting of a nitroalkyl anion, an alkyl sulphone anion, an acyl anion equivalent, and an organocuprate produced from an alkyl halide, vinyl halide, or vinyl ether.

19. The method of claim 17, wherein the compound of Formula (III) is the product of an intermolecular metathesis reaction of a chiral allylcyclopentenone performed in the presence of a transition metal catalyst, wherein the allylcyclopentenone is a compound of Formula (I):

(I)

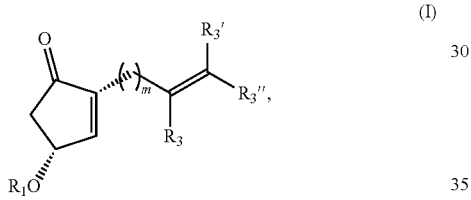

wherein m, $R_1$ and $R_3$ are as defined for the compound of Formula (III) and wherein $R_3'$ and $R_3''$ are each selected from the group consisting of H, alkyl, substituted alkyl, aralkyl, substituted aralkyl, aryl, substituted aryl, alkoxyl, aralkoxyl, and acyloxyl.

20. The method of claim 16, wherein the compound of Formula (IV) is the product of the intermolecular metathesis reaction of a compound of Formula (II):

(II)

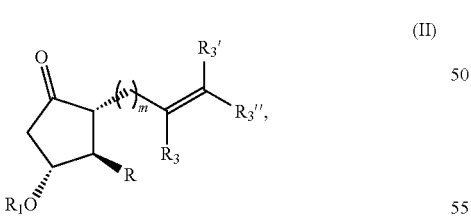

wherein m is an integer from 0 to 10, and R, $R_1$ and $R_3$ are as defined for the compound of Formula (VI) and wherein $R_3'$ and $R_3''$ are each selected from the group consisting of H, alkyl, substituted alkyl, aralkyl, substituted aralkyl, aryl, substituted aryl, alkoxyl, aralkoxyl, and acyloxyl, optionally wherein at least one of $R_3'$ and $R_3''$ is other than H, wherein the metathesis reaction is performed in the presence of a transition metal catalyst.

21. The method of claim 1, wherein the compound of Formula (VII) is a nitro group-containing compound of the formula:

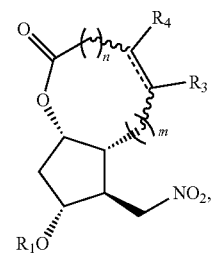

wherein:
≡ represents a single or a double bond;
n and m are each independently an integer between 0 and 10;
$R_1$ is H or a hydroxyl protecting group;
$R_3$ and $R_4$ are each independently selected from the group consisting of H, alkyl, substituted alkyl, aralkyl, substituted aralkyl, aryl, and substituted aryl; and
wherein the method further comprises contacting the nitro group-containing compound with titanium trichloride and sodium acetate to provide an aldehyde of the formula:

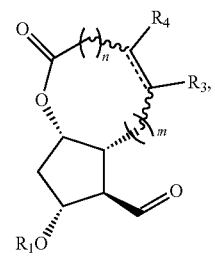

wherein n, m, $R_1$, $R_3$, and $R_4$ are as described for the nitro group-containing compound.

22. The method of claim 21, further comprising performing a Horner-Emmons reaction between the aldehyde and a phosphonate to provide a compound of Formula (XI):

XI

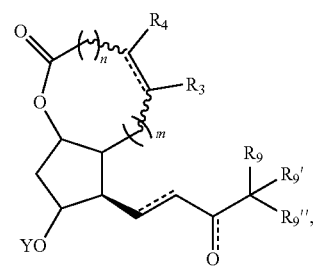

wherein:
≡ represents a single or a double bond;
Y is H or a hydroxyl protecting group;
n and m are independently integers between 0 and 10;
$R_3$ and $R_4$ are independently selected from the group consisting of H, alkyl, substituted alkyl, aralkyl, substituted aralkyl, aryl, and substituted aryl;
$R_9$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino;

$R_9'$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9'$ is not halogen or amino when $R_9$ or $R_9''$ is hydroxyl or amino;

$R_9''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9''$ is not halogen or amino when $R_9$ or $R_9'$ is hydroxyl or amino;

or two or more of $R_9$, $R_9'$, and $R_9''$ together form a ring.

23. The method of claim 1, wherein the compound of Formula (VII) is
a compound of the Formulae (VII-6) or (VIII-6):

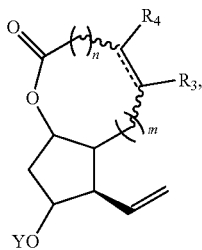

(VII-6, VIII-6)

wherein:
≡ represents a single or a double bond;
n and m are independently integers between 1 and 10 or 0 and 10;
Y is a hydroxyl protecting group for the compounds of Formula (VII-6) and H for the compounds of Formula (VIII-6); and
$R_3$ and $R_4$ are independently selected from the group consisting of H, alkyl, substituted alkyl, aralkyl, substituted aralkyl, aryl, and substituted aryl; and wherein the method further comprises performing one of the following steps:

(a) contacting the compound of Formula (VII-6) or (VIII-6) with a metal catalyst and a suitable enone to perform a cross-metathesis reaction, thereby providing a compound of Formula (XI):

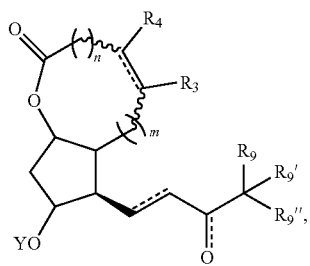

XI wherein:
≡ represents a single or a double bond;
Y is H or a hydroxyl protecting group;
n and m are independently integers between 0 and 10;
$R_3$ and $R_4$ are independently selected from the group consisting of H, alkyl, substituted alkyl, aralkyl, substituted aralkyl, aryl, and substituted aryl;
$R_9$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino;
$R_9'$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9'$ is not halogen or amino when $R_9$ or $R_9''$ is hydroxyl or amino;
$R_9''$ is hydrogen, alkyl, substituted alkyl, cycloalkyl, substituted cycloalkyl, vinyl, aryl, substituted aryl, aralkyl, substituted aralkyl, acyl, alkoxyl, aralkoxyl, substituted aralkoxyl, aryloxyl, thioalkyl, thioaralkyl, thioaryl, furyl, pyranyl, thiophenyl, benzothiophenyl, halogen, hydroxyl, protected hydroxyl, or amino, provided that $R_9''$ is not halogen or amino when $R_9$ or $R_9'$ is hydroxyl or amino;
or two or more of $R_9$, $R_9'$, and $R_9''$ together form a ring;

(b) hydrolyzing the compound of Formula (VII-6) or (VIII-6) to open the lactone and then reacting the resulting carboxylic acid with an alkoxide, thiol, or amine to provide a compound of Formula (XIV):

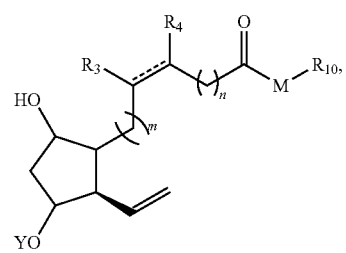

XIV wherein:
≡ represents a single or a double bond;
Y is H or a hydroxyl protecting group;
n and m are independently integers between 0 and 10;
$R_3$ and $R_4$ are independently selected from the group consisting of H, alkyl, substituted alkyl, aralkyl, substituted aralkyl, aryl, and substituted aryl;
M is nitrogen, oxygen or sulfur; and
$R_{10}$ is hydrogen, alkyl, substituted alkyl, cycloalkyl, substituted cycloalkyl, aryl, substituted aryl, aralkyl, substituted aralkyl, alkylacyl, hydroxyacyl, alkoxyacyl, aminoacyl, alkylaminoacyl, or alkylthioacyl; or (c) trans-esterifying the compound of Formula (VII-6) or (VIII-6) with a chiral allylic alcohol to provide a compound of Formula (XV):

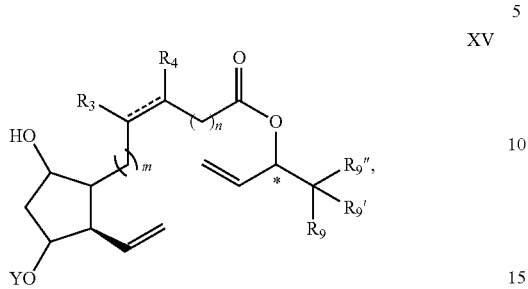

XV wherein ===, n, m, Y, $R_3$, $R_4$, $R_9$, $R_9'$, and $R_9''$ are as described for the compound of Formula (XI); and * represents a chiral center, which can be racemic or enatiomerically pure; optionally wherein the compound of Formula (XV) can be further reacted with a metal catalyst to undergo an intramolecular metathesis reaction to provide a compound of Formula (XVI):

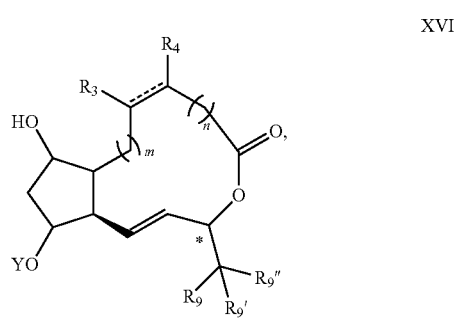

XVI wherein ===, n, m, Y, $R_3$, $R_4$, $R_9$, $R_9'$, and $R_9''$ are as described for the compound of Formula (XV).

* * * * *